(12) United States Patent
Lizardi et al.

(10) Patent No.: US 6,261,782 B1
(45) Date of Patent: Jul. 17, 2001

(54) FIXED ADDRESS ANALYSIS OF SEQUENCE TAGS

(75) Inventors: Paul M. Lizardi, Wallingford; Matthew E. Roth, Branford; Li Feng, Hamden; Cesar E. Guerra, Guilford; Shane C. Weber, Woodbridge; Joseph C. Kaufman, Hamden; Darin R. Latimer, East Haven, all of CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/544,713

(22) Filed: Apr. 6, 2000

Related U.S. Application Data

(60) Provisional application No. 60/127,932, filed on Apr. 6, 1999.

(51) Int. Cl.$^7$ .............................. C12Q 1/68; C07H 21/04; C12P 19/34

(52) U.S. Cl. ........................ 435/6; 435/91.2; 536/23.1; 536/24.2; 536/24.3

(58) Field of Search ..................... 435/6, 91.2; 536/23.1, 536/24.2, 24.3

(56) References Cited

U.S. PATENT DOCUMENTS

| | | |
|---|---|---|
| 5,429,807 | 7/1995 | Matson et al. . |
| 5,508,169 * | 4/1996 | Deugau et al. ........................ 435/6 |
| 5,599,695 | 2/1997 | Pease et al. . |
| 5,607,924 | 3/1997 | Magda et al. . |
| 5,654,413 | 8/1997 | Brenner . |
| 5,728,524 * | 3/1998 | Sibson ................................... 435/6 |
| 5,736,330 | 4/1998 | Fulton . |
| 5,854,033 | 12/1998 | Lizardi . |
| 5,858,656 * | 1/1999 | Deugau et al. ........................ 435/6 |
| 5,871,697 | 2/1999 | Rothberg et al. . |
| 5,871,918 | 2/1999 | Thorp et al. . |
| 5,871,928 | 2/1999 | Fodor et al. . |
| 5,968,745 | 10/1999 | Thorp et al. . |
| 5,985,153 | 11/1999 | Dolan et al. . |
| 5,993,665 | 11/1999 | Terstappen et al. . |
| 5,994,068 * | 11/1999 | Guilfoyle et al. ..................... 435/6 |
| 6,013,188 | 1/2000 | Terstappen et al. . |
| 6,023,540 | 2/2000 | Walt et al. . |

FOREIGN PATENT DOCUMENTS

| | | |
|---|---|---|
| WO 97/19193 A2 | 5/1997 | (WO) . |
| WO 98/50782 A2 | 5/1998 | (WO) . |
| WO 99/19515 A1 | 4/1999 | (WO) . |
| WO 99/28505 A1 | 6/1999 | (WO) . |
| WO 99/37814 A1 | 7/1999 | (WO) . |
| WO 99/64847 A1 | 12/1999 | (WO) . |
| WO 00/04036 A1 | 1/2000 | (WO) . |
| WO 00/08443 A1 | 2/2000 | (WO) . |

OTHER PUBLICATIONS

Adams, et al., "Complementary DNA sequencing: expressed sequence tags and human genome project,"0 *Science* 252(5013):1651–56 (1991).

Adams, et al., "Initial assessment of human gene diversity and expression patterns based upon 83 million nucleotides of cDNA sequence," *Nature* 377:3–174 (1995).

Airoldi, et al., "Carcinogen–DNA adducts as tools in risk assessment," *Adv. Exp. Med. Biol.* 472:231–40 (1999).

Alwine, et al., "Method for detection of specific RNAs in agarose gels by transfer to diazobenzyloxmethyl–paper and hybridization with DNA probes," *Proc. Natl. Acad. Sci. U. S. A.* 74(12):5350–4 (1977).

Bauer, et al., "Identification of differentially expressed mRNA species by an improved display technique (DDRT–PCR)," *Nucleic Acids Res.* 21(18):4272–80 (1993).

Baylin, et al., "Alterations in DNA methylation: a fundamental aspect of neoplasia," *Adv. Cancer Res.* 72:141–96 (1998).

Bird & Wolffe, "Methylation–induced repression—belts, braces, and chromatin" *Cell* 99(5):451–4 (1999).

Bird, "DNA methylation de novo," *Science* 286(5448):2287–8 (1999).

Birkenmeyer & Mushahwar, "DNA probe amplification methods," *J. Virol. Methods* 35(2):117–26 (1991).

Breaker & Joyce, "A DNA enzyme that cleaves RNA," *Chemistry & Biology* 1:223–229 (1994).

(List continued on next page.)

*Primary Examiner*—Kenneth R. Horlick
(74) *Attorney, Agent, or Firm*—Needle & Rosenberg, P.C.

(57) ABSTRACT

Disclosed is a method for the comprehensive analysis of nucleic acid samples and a detector composition for use in the method. The method, referred to as Fixed Address Analysis of Sequence Tags (FAAST), involves generation of a set of nucleic acid fragments having a variety of sticky end sequences; indexing of the fragments into sets based on the sequence of sticky ends; associating a detector sequence with the fragments; sequence-based capture of the indexed fragments on a detector array; and detection of the fragment labels. Generation of the multiple sticky end sequences is accomplished by incubating the nucleic acid sample with one or more nucleic acid cleaving reagents. The indexed fragments are captured by hybridization and coupling, preferably by ligation, to a probe. The method allows a complex sample of nucleic acid to be quickly and easily cataloged in a reproducible and sequence-specific manner. One form of the method allows determination of associations, in a nucleic acid molecule, of different combinations of known or potential sequences. Another form of the method assesses modification of sequences in nucleic acid molecules by basing cleavage of the molecules on the presence or absence of modification.

154 Claims, 5 Drawing Sheets

OTHER PUBLICATIONS

Breslauer, et al., "Predicting DNA duplex stability from the base sequence," *Proc. Natl. Acad. Sci. U. S. A.* 83(11):3746–50 (1986).

Carmi, et al., "Cleaving DNA with DNA," *Proc. Natl. Acad. Sci. U. S. A.* 95(5):2233–7 (1998).

Cartwright, et al., "Cleavage of chromatin with methidium-propyl–EDTA . iron(II)," *Proc. Natl. Acad. Sci. U. S. A.* 80(11):3213–7 (1983).

Chan & Nie, "Quantum dot bioconjugates for ultrasensitive nonisotopic detection," *Science* 281:2016–18 (1998).

Chee, et al., "Accesing genetic information with high–density DNA arrays," *Science* 274(5287):610–4 (1996).

Costello, et al., "Aberrant CpG–island methylation has non–random and tumour–type–specific patterns," *Nat. Genet.* 24(2):132–8 (2000).

Davis & Bjorkman, "T–cell antigen receptor genes and T–cell recognition," *Nature* 334:395–402 (1988).

Dayhoff, et al., "A model of evolutionary changes in proteins" in *Atlas of Protein Sequence and Structure*, M.O. Dayhoff, Editor. 1978, National Biomedical Research Foundation: Washington DC.

De Haas, et al., "Platinum porphyrins as phosphorescent label for time–resolved microscopy," *J. Histochem. Cytochem.* 45(9):1279–92 (1997).

Diatchenko, et al, "Suppression subtractive hybridization: a method for generating differentially regulated or tissue–specific cDNA probes and libraries," *Proc. Natl. Acad. Sci. U. S. A.* 93(12):6025–30 (1996).

Edman, et al., "Identification of ErbB3–stimulated genes using modified representational difference analysis," *Biochem. J.* 323 (Pt 1):113–8 (1997).

Ellis, et al., "Chemical cleavage of mismatch: a new look at an established method," *Hum. Mutat.* 11(5):345–53 (1998).

Finnegan, et al., "DNA Methylation in Plants," *Annual Rev. Physiol.* 49:223–247 (1998).

Fodor, et al., "Multiplexed biochemical assays with biological chips," *Nature* 364:555–556 (1993).

Freier, et al., "Improved free–energy parameters for predictions of RNA duplex stability," *Proc. Natl. Acad. Sci. U. S. A.* 83(24):9373–7 (1986).

Gamboa Da Costa, et al., "Characterization of the Major DNA Adduct Formed by Alpha–Hydroxy–N–desmethyltamoxifen in Vitro and in Vivo," *Chem. Res. Toxicol.* 13(3):200–207 (2000).

Gonzalgo & Jones, "Rapid quantitation of methylation differences at specific sites using methylation–sensitive single nucleotide primer extension (Ms–SNuPE)," *Nucl. Acids Res.* 25:2529–31 (1997).

Guo, et al., "Direct fluorescence analysis of genetic polymorphisms by hybridization with oligonucleotide arrays on glass supports," *Nucleic Acids Res.* 22(24):5456–5465 (1994).

Habraken, et al., "ATP–dependent assembly of a ternary complex consisting of a DNA mismatch and the yeast MSH2–MSH6 and MLH1–PMS1 protein complexes," *J. Biol. Chem.* 273(16):9837–41 (1998).

Habraken, et al., "Binding of insertion/deletion DNA mismatches by the heterodimer of yeast mismatch repair proteins MSH2 and MSH3," *Curr. Biol.* 6(9):1185–7 (1996).

Hanvey, et al., "Antisense and antigene properties of peptide nucleic acids," *Science* 258(5087):1481–5 (1992).

Hatada, et al., "A genomic scanning method for higher organisms using restriction sites as landmarks," *Proc. Natl. Acad. Sci. USA* 88:9523–27 (1991).

Hedrick, et al., "Isolation of cDNA clones encoding T cell–specific membrane–associated proteins," *Nature.* 308(5955):149–53 (1984).

Hermanson, et al., *Immobilized Affinity Ligands*. (Academic Press, New York, 1992).

Hoheisel, "Sequence–independent and linear variation of oligonucleotide DNA binding stabilities," *Nucleic Acids Res.* 24(3):430–2 (1996).

Hoy, et al., "Bromodeoxyuridine/DNA analysis of replication CHO cells after exposure to UV light," *Mutat. Res.* 290(2):217–30 (1993).

Hsu, "Mismatch cleavage detects base deletion in cystic fibrosis gene," *Biotechniques* 25:692–6 (1998).

Hubank & Schatz, "Identifying differences in mRNA expression by representational difference analysis of cDNA," *Nucleic Acids Res.* 22(25):5640–8 (1994).

Ito & Sakaki, "Fluorescent differential display," *Methods Mol. Biol.* 85:37–44 (1997).

Johnstone & Thorpe, *Immunochemistry In Practice* (Blackwell Scientific Publications, Oxford, England, 1987) pp. 209–216 and 241–242.

Karger, et al., "Digital chemiluminescence imaging of DNA sequencing blots using a charge–coupled device camera," *Nucleic Acids Res.* 20(24):6657–65 (1992).

Kerkhof, "A Comparison of Substrates for Quantifying the Signal from a Nonradiolabeled DNA Probe," *Analytical Biochemistry* 205:359–364 (1992).

Keyes, et al., "Overall and internal dynamics of DNA as monitored by five–atom–tethered spin labels," *Biophys. J.* 72(1):282–90 (1997).

Khrapko, et al., "Hybridization of DNA with oligonucleotides immobilized in a gel: a convenient method for recording single base replacements," *Mol. Biol. (Mosk).* 25(3):718–30 (1991).

Kirschstein, et al., "Detection of the DeltaF508 mutation in the CFTR gene by means of time– resolved fluorescence methods," *Bioelectrochem. Bioenerg.* 48(2):415–21 (1999).

Kortenkamp, et al., "Genotypic selection of mutated DNA sequences using mismatch cleavage analysis, a possible basis for novel mutation assays," *Mutagenesis* 12:335–8 (1997).

Kozian & Kirschbaum, "Comparative gene–expression analysis," *Trends Biotechnol.* 17(2):73–8 (1999).

Kricka, "Chemiluminescent and bioluminescent techniques," *Clin. Chem.* 37(9):1472–81 (1991).

Kricka, "Selected strategies for improving sensitivity and reliability of immunoassays," *Clin. Chem.* 40(3):347–57 (1994).

Kumke, et al., "Temperature and quenching studies of fluorescence polarization detection of DNA hybridization," *Anal. Chem.* 69(3):500–6 (1997).

Landgren, "Molecular mechanics of nucleic acid sequence amplification," *Trends Genetics* 9:199–202 (1993).

Langer, et al., "Enzymatic synthesis of biotin–labeled polynucleotides: Novel nucleic acid affinity probes", *Proc. Nat. Acad. Sci. USA* 78(11):6633–6637 (1981).

Lavery, et al., "Selective amplification via biotin– and restriction–mediated enrichment (SABRE), a novel selective amplification procedure for detection of differentially expressed mRNAs," *Proc. Natl. Acad. Sci. U. S. A.* 94(13):6831–6 (1997).

Lee, et al., "Comparative expressed–sequence–tag analysis of differential gene expression profiles in PC–12 cells before and after nerve growth factor treatment," *Proc. Natl. Acad. Sci. U. S. A.* 92(18):8303–7 (1995).

Liang & Pardee, "Differential display of eukaryotic messenger RNA by means of the polymerase chain reaction," *Science.* 57(5072):967–71 (1992).

Liagn & Pardee, "Recent advances in differential display," *Curr. Opin. Immunol.* 7(2):274–80 (1995).

Lipshutz, "Likelihood DNA sequencing by hybridization," *J. Biomol. Struct. Dyn.* 11(3):637–53 (1993).

Lisitsyn, et al., "Cloning the differences between two complex genomes," *Science* 259(5097):946–51 (1993).

Lizardi, et al., "Mutation detection and single–molecule counting using isothermal rolling–circle amplification," *Nat Genet.* 19(3):225–32 (1998).

Lodovici, et al., "Levels of 8–hydroxydeoxyguanosine as a marker of DNA damage in human leukocytes," *Free Radic. Biol. Med.* 28(1):13–7 (2000).

Lu & Hsu, "Detection of single DNA base mutations with mismatch repair enzymes," *Genomics* 14(2):249–55 (1992).

Maehira, et al., "Alterations of protein kinase C, 8–hydroxydeoxyguanosine, and K–ras oncogene in rat lungs exposed to passive smoking," *Clin. Chim. Acta.* 289(1–2):133–44 (1999).

Maniatis, et al., "The isolation of structural genes from libraries of eucaryotic DNA," *Cell* 15(2):687–701 (1978).

Mansfield, et al., "Nucleic acid detection using non–radioactive labeling methods," *Mol. Cell Probes* 9(3):145–56 (1995).

Mashal, "Detection of mutations by cleavage of DNA heteroduplexes with bacteriophage resolvases," *Nat. Genet.* 9:177–83 (1995).

McCreery, "Digoxigenin labeling," *Mol. Biotechnol.* 7(2):121–4 (1997).

Melki, et al., "Concurrent DNA hypermethylation of multiple genes in acute myeloid leukemia," *Cancer Res.* 59(15):3730–40 (1999).

Michael, et al., "Randomly ordered addressable high–density optical sensor arrays," *Anal. Chem.* 70(7):1242–8 (1998).

Napier, et al., "Probing biomolecule recognition with electron transfer: electrochemical sensors for DNA hybridization," *Bioconjug. Chem.* 8(6):906–13 (1997).

Neddermann & Jiricny, "Efficient removal of uracil from G.U mispairs by the mismatch–specific thymine DNA glycosylase from HeLa cells," *Proc. Natl. Acad. Sci. U. S. A.* 91(5):1642–6 (1994).

Nguyen, et al., "Modification of DNA duplexes to smooth their thermal stability independently of their base content for DNA sequencing by hybridization," *Nucleic Acids Res.* 25(15):3059–3065 (1997).

Nguyen, et al., "Smoothing of the thermal stability of DNA duplexes by using modified nucleosides and chaotropic agents," *Nucleic Acids Res.* 27(6):1492–1498 (1999).

Nikiforov, et al., "Genetic Bit Analysis: a solid phase method for typing single nucleotide polymorphisms," *Nucleic Acids Res.* 22(20):4167–75 (1994).

Nikiforov, et al., "The Use of Phosphorothioate Primers and Exonuclease Hydrolysis for the Preparation of Single–stranded PCR Products and their Detection by Solid–phase Hybridization," *PCR Method and Applications* 3:285–291 (1994).

Nurmi, et al., "A new label technology for the detection of specific polymerase chain reaction products in a closed tube," *Nucleic Acids Res.* 28(8):28 (2000).

O'Neill & Sinclair, "Isolation of rare transcripts by representational difference analysis," *Nucleic Acids Res.* 25:2681–2682 (1997).

Oetting, et al., "Multiplexed short tandem repeat polymorphisms of the Weber 8A set of markers using tailed primers and infrared fluorescence detection," *Electrophoresis* 19(18):3079–83 (1998).

Olejnik, et al., "Photocleavable affinity tags for isolation and detection of biomolecules," *Methods Enzymol.* 291:135–54 (1998).

Olejnik, et al., "Photocleavable aminotag phosphoramidites for 5'–termini DNA/RNA labeling," *Nucleic Acids Res.* 26(15):3572–6 (1998).

Olejnik, et al., "Photocleavable biotin derivatives: a versatile approach for the isolation of biomolecules," *Proc. Natl. Acad. Sci. U. S. A.* 92(16):7590–4 (1995).

Olejnik, et al., "Photocleavable biotin phosphoramidite for 5'–end–labeling, affinity purification and phosphorylation of synthetic oligonucleotides," *Nucleic Acids Res.* 24:361–66 (1996).

Olejnik, et al., "Photocleavable peptide–DNA conjugates: synthesis and applications to DNA analysis using MALDI–MS," *Nucleic Acids Res.* 27(23):4626–31 (1999).

Paciotti, et al., "Mec1p is essential for phosphorylation of the yeast DNA damage checkpoint protein Ddc1p, which physically interacts with Mec3p," *EMBO J.* 17(14):4199–209 (1998).

Pang, et al., "Functional domains of the *Saccharomyces cerevisiae* Mlh1p and Pms1p DNA mismatch repair proteins and their relevance to human hereditary nonpolyposis colorectal cancer–associated mutations," *Mol. Cell. Biol.* 17(8):4465–73 (1997).

Pease, et al., "Light–generated oligonucleotide arrays for rapid DNA sequence analysis," *Proc. Natl. Acad. Sci. USA* 91(11):5022–5026 (1994).

Phillips, et al., "Methods of DNA adduct determination and their application to testing compounds for genotoxicity," *Environ. Mol. Mutagen* 35(3):222–233 (2000).

Podhajska & Szybalski, "Conversion of the FokI endonuclease to a universal restriction enzyme: cleavage of phage M13mp7 DNA at predetermined sites," *Gene* 40(2–3):175–82 (1985)[published erratum appears in Gene 43(3):325 (1985)]).

Prashar & Weissman, "Analysis of differential gene expression by display of 3' end restriction fragments of cDNAs," *Proc. Natl. Acad. Sci. U.S.A.* 93:659–663 (1996).

Purewal, et al., "Association between acetylator genotype and 2–amino–1–methyl–6–phenylimidazo[4,5–b]pyridine (PhIP) DNA adduct formation in colon and prostate of inbred Fischer 344 and Wistar Kyoto rats," *Cancer Lett.* 149(1–2):53–60 (2000).

Rabinowicz, et al., "Differential methylation of genes and retrotransposons facilitates shotgun sequencing of the maize genome," *Nat. Genet.* 23:305–308 (1999).

Ren, et al., "Chemical mismatch cleavage combined with capillary electrophoresis: detection of mutations exon 8 of the cystathionine beta–synthase gene," *Clin. Chem.* 44:2108–14 (1998).

Roda, et al., "Chemiluminescent imaging of enzyme–labeled probes using an optical microscope–videocamera luminograph," *Anal. Biochem.* 257(1):53–62 (1998).

Santalucia, et al., "Improved nearest–neighbor parameters for predicting DNA duplex stability," *Biochemistry* 35:3555–3562 (1996).

Schena, et al., "Quantitative Monitoring of Gene Expression Patterns with a Complementary DNA Microarray," *Science* 270:467–470 (1995).

Schultz & Dervan, "Sequence–specific double–strand cleavage of DNA by penta–N– methylpyrrolecarboxamide–EDTA X Fe(II)," *Proc. Natl. Acad. Sci. U. S. A.* 80(22):6834–7 (1983).

Sewell, & Durbin, "Method for calculation of probability of matching a bounded regular expression in a random data string," *J. of Computational Biology* 2:25–31 (1995).

Siddiqi, et al., "Evaluation of electrochemiluminescence– and bioluminescence–based assays for quantitating specific DNA," *J. Clin. Lab. Anal.* 10(6):423–31 (1996).

Squire, et al., "Multiple frequencey fluorescence lifetime imaging microscopy," *J. Microscopy* 197(2):136–149 (2000).

Stevenson, et al., "Synchronous luminescence: a new detection technique for multiple fluorescent probes used for DNA sequencing," *Biotechniques* 16(6):1104–11 (1994).

Stimpson, et al., "Real–time detection of DNA hybridization and melting on oligonucleotide arrays by using optical wave guides," *Proc. Natl. Acad. Sci. USA* 92(14):6379–6383 (1995).

Swaroop, et al., "A simple and efficient cDNA library subtraction procedure: isolation of human retina–specific cDNA clones," *Nucleic Acids Res.* 19(8):1954 (1991).

Syvänen, et al., "Fast quantification of nucleic acid hybrids by affinity–based hybrid collection," *Nucleic Acids Res.* 14(12):5037–48 (1986).

Szybalski, "Universal restriction endonucleases: designing novel cleavage specificities by combining adapter oligodeoxynucleotide and enzyme moieties," *Gene* 40(2–3):169–73 (1985).

Taylor, *Protein immobilization: fundamentals and applications* (M. Dekker, New York, 1991).

Tibbe, et al., "Optical tracking and detection of immunomagnetically selected and aligned cells," *Nat. Biotechnol.* 17(12):1210–3 (1999).

Unrau & Deugau, "Non–cloning amplification of specific DNA fragments from whole genomic DNA digests using DNA 'indexers'" *Gene* 145:163–169 (1994).

Vasmatzis, et al., "Discovery of three genes specifically expressed in human prostate by expressed sequence tag database analysis," *Proc. Natl. Acad. Sci. U. S. A.* 95:300–304 (1998).

Velculescu, et al., "Serial analysis of gene expression," *Science,* 270(5235):484–7 (1995).

Venezia & O'Hara, "Rapid motif compliance scoring with match weight sets," *Comput. Appl. Biosci.* 9(1):65–9 (1993).

Vo–Dinh, et al., "Surface–enhanced Raman gene probes," *Anal. Chem.* 66(20):3379–83 (1994).

Volkers, et al., "Microwave label detection technique for DNA in situ hybridization," *Eur. J. Morphol.* 29(1):59–62 (1991).

Wada, et al., "Representational difference analysis of cDNA of genes expressed in embryonic kidney," *Kidney Int.* 51:1629–1638 (1997).

Walker, et al., "Strand displacement amplification—an isothermal, in vitro DNA amplification technique," *Nucleic Acids Res.* 20(7):1691–6 (1992).

Walt, "Techview: molecular biology. Bead–based fiber-optic arrays," *Science* 287(5452):451–2 (2000).

Wansink, et al., "Fluorescent Labeling of Nascent RNA Reveals Transcription by RNA Polymerase II in Domains Scattered Throughout the Nucleus," *Journal of Cell Biology* 122(2):283–293 (1993).

Whitney, et al., "A genome–wide functional assay of signal transduction in living mammalian cells," *Nat. Biotechnol.* 16(13):1329–33 (1998).

Wood, et al., "Base composition–independent hybridization in tetramethylammonium chloride: a method for oligonucleotide screening of highly complex gene libraries," *Proc. Natl. Acad. Sci. USA* 82(6):1585–1588 (1985).

Xiong & Laird, "Cobra: a sensitive and quantitative DNA methlyation assay," *Nuc. Acid Res.* 25(12):2532–2534 (1997).

Yao & Kow, "Further characterization of *Escherichia coli* endonuclease V. Mechanism of recognition for deoyinosine, deoxyuridine, and base mismatches in DNA," *J. Biol. Chem.* 272:30774–79 (1997).

Yeh, et al., "Mammalian topoisomerase I has base mismatch nicking activity," *J. Biol. Chem.* 269(22):15498–504 (1994).

Youil, et al., "Detection of 81 of 81 known mouse beta––globin promoter mutations with T4 endonuclease VII—the EMC method," *Genomics* 32:431–435 (1996).

Yu, et al., "Cyanine dye dUTP analogs for enzymatic labeling of DNA probes," *Nucleic Acids Research* 22(15):3226–3232 (1994).

Zlokarnik, et al., "Quantitation of transcription and clonal selection of single living cells with β–lactamase as reporter," *Science* 279:84–88 (1998).

* cited by examiner

Figure 1

Adaptor-indexer I

CATGCGGATCCTAAGGCTTACGCC
GCCTAGGATTCCGAATGCGG

Adaptor-indexer II

TAATGGAAGCTGGATTCGCG
GTTCATTACCTTCGACCTAAGCGC

Ligator-detectors

1. CATGCGGATCCTAAGGCTTACGCC
2. CATGCGGATCCTAAGGCTTACGC
3. CATGCGGATCCTAAGGCTTA
4. CATGCGGATCCTAAGGC
5. ATGCGGATCCTAAGGCTTACGCC
6. TGCGGATCCTAAGGCTTACGCC
7. GCGGATCCTAAGGCTTACGCC
8. ATGCGGATCCTAAGGCTTACGC
9. ATGCGGATCCTAAGGCTTACG
10. ATGCGGATCCTAAGGCTT
11. ATGCGGATCCTAAGGC
12. TGCGGATCCTAAGGCTTAC
13. GGCGTAAGCCTTAGGATCCGCATC
14. GCGTAAGCCTTAGGATCCGCATC
15. GTAAGCCTTAGGATCCGCATC
16. CCTTAGGATCCGCATC
17. GGCGTAAGCCTTAGGATCCGCAT
18. GGCGTAAGCCTTAGGATCCGCA
19. GGCGTAAGCCTTAGGATCCGC
20. GCATGCGGATCCTAAGGCTTACGCC

Ligator-detectors

21. CAAGTAATGGAAGCTGGATTCGCG
22. CAAGTAATGGAAGCTGGATTCGC
23. CAAGTAATGGAAGCTGGATTC
24. CAAGTAATGGAAGCT
25. AAGTAATGGAAGCTGGATTCGCG
26. AGTAATGGAAGCTGGATTCGCG
27. GTAATGGAAGCTGGATTCGCG
28. AAGTAATGGAAGCTGGATTCGC
29. AAGTAATGGAAGCTGGATTC
30. AAGTAATGGAAGCTGGAT
31. AAGTAATGGAAGCTG
32. AGTAATGGAAGCTGGATTCGCG
33. CGCGAATCCAGCTTCCATTACTTG
34. GCGAATCCAGCTTCCATTACTTG
35. GAATCCAGCTTCCATTACTTG
36. CAGCTTCCATTACTTG
37. CGCGAATCCAGCTTCCATTACTT
38. CGCGAATCCAGCTTCCATTACT
39. CGCGAATCCAGCTTCCATTAC
40. GAATCCAGCTTCCATTACTT

Figure 2

A  ...ATATGCTTTAGGC<u>GGATG</u>CTAAATCGTATGGACAACCAGCCATTCACGGGC...
   ...TATACGAAATCCGCCTACGATTTAGCATACCTGTTGGTCGGTAAGTGCCCG...

B  ...ATATGCTTTAGGC<u>GGATG</u>CTAAATCGT        ATGGACAACCAGCCATTCACGGGC...
   ...TATACGAAATCCGCCTACGATTTAGCATACC        TGTTGGTCGGTAAGTGCCCG...

C  ...ATATGCTTTAGGC<u>GGATG</u>CTAAATCGT        ATGGCGGATCCTAAGGCTTACGCC
   ...TATACGAAATCCGCCTACGATTTAGCATACC        GCCTAGGATTCCGAATGCGG

D  ...ATATGCTTTAGGC<u>GGATG</u>CTAAATCGTATGGCGGATCCTAAGGCTTACGCC
   ...TATACGAAATCCGCCTACGATTTAGCATACCGCCTAGGATTCCGAATGCGG

E  ...ATATGCTTTAGGC<u>GGATG</u>CTAAATCGTATGGCGGATCCTAAGGCTTACGCC
                                  TACCGCCTAGGATTCCGAATGCGG-label F  ...ATATGCTTTAGGC<u>GGATG</u>CTAAATCGTATGGCGGATCCTAAGGCTTACGCC
                                  TACCGCCTAGGATTCCGAATGCGG-label G  ...ATATGCTTTAGGC<u>GGATG</u>CTAAATCGTATGGCGGATCCTAAGGCTTACGCC
                                  TACCGCCTAGGATTCCGAATGCGG-label
                    TTAGCA
              support H  ...ATATGCTTTAGGC<u>GGATG</u>CTAAATCGTATGGCGGATCCTAAGGCTTACGCC
                       TTAGCATACCGCCTAGGATTCCGAATGCGG-label
                 support I                      TTAGCATACCGCCTAGGATTCCGAATGCGG-label
              support

Figure 3

A   ...ATATGCTTTAGGC<u>GGATG</u>CTAAATCGTATGGACAACCAGCCATTCACGGGC...
    ...TATACGAAATCCGCCTACGATTTAGCATACCTGTTGGTCGGTAAGTGCCCG...

B   ...ATATGCTTTAGGC<u>GGATG</u>CTAAATCGT     ATGGACAACCAGCCATTCACGGGC...
    ...TATACGAAATCCGCCTACGATTTAGCATACC     TGTTGGTCGGTAAGTGCCCG...

C   ...ATATGCTTTAGGC<u>GGATG</u>CTAAATCGT     ATGGCGGATCCTAAGGCTTACGCC
    ...TATACGAAATCCGCCTACGATTTAGCATACC     GCCTAGGATTCCGAATGCGG

D   ...ATATGCTTTAGGC<u>GGATG</u>CTAAATCGTATGGCGGATCCTAAGGCTTACGCC
    ...TATACGAAATCCGCCTACGATTTAGCATACCGCCTAGGATTCCGAATGCGG

E                                  ATGGCGGATCCTAAGGCTTACGCC-label
    ...TATACGAAATCCG<u>CCTAC</u>GATTTAGCATACCGCCTAGGATTCCGAATGCGG F.                                 ATGGCGGATCCTAAGGCTTACGCC-label
    ...TATACGAAATCCG<u>CCTAC</u>GATTTAGCATACCGCCTAGGATTCCGAATGCGG G              support
                    AATCGT

ATGGCGGATCCTAAGGCTTACGCC-label
    ...TATACGAAATCCG<u>CCTAC</u>GATTTAGCATACCGCCTAGGATTCCGAATGCGG H             support
                    AATCGTATGGCGGATCCTAAGGCTTACGCC-label
    ...TATACGAAATCCG<u>CCTAC</u>GATTTAGCATACCGCCTAGGATTCCGAATGCGG I             support
                    AATCGTATGGCGGATCCTAAGGCTTACGCC-label

Figure 4

```
A    ...TCCCTGATCAGAATC...ATATGCTTTAGGCGGATGCTAAATCGTATGGACAACCAGCCATTCACGGG...
     ...AGGGACTAGTCTTAG...TATACGAAATCCGCCTACGATTTAGCATACCTGTTGGTCGGTAAGTGCCC...

D    ...TCCCTGATCAGAATC...ATATGCTTTAGGCGGATGCTAAATCGTATGGCGGATCCTAAGGCTTACGCC
     ...AGGGACTAGTCTTAG...TATACGAAATCCGCCTACGATTTAGCATACCGCCTAGGATTCCGAATGCGG

D1   ...TCCCT       GATCAGAATC...ATATGCTTTAGGCGGATGCTAAATCGTATGGCGGATCCTAAGGCTTACGCC
     ...AGGGACTAG       TCTTAG...TATACGAAATCCGCCTACGATTTAGCATACCGCCTAGGATTCCGAATGCGG

D2   GCAACTTCAAAGCCTTTAGC       GATCAGAATC...ATATGCTTTAGGCGGATGCTAAATCGTATGGCGGATCCTAAGGCTTACGCC
     CGTTGAAGTTTCGGAAATCGCTAG       TCTTAG...TATACGAAATCCGCCTACGATTTAGCATACCGCCTAGGATTCCGAATGCGG

D3   GCAACTTCAAAGCCTTTAGCGATCAGAATC...ATATGCTTTAGGCGGATGCTAAATCGTATGGCGGATCCTAAGGCTTACGCC
     CGTTGAAGTTTCGGAAATCGCTAGTCTTAG...TATACGAAATCCGCCTACGATTTAGCATACCGCCTAGGATTCCGAATGCGG

F    GCAACTTCAAAGCCTTTAGCGATCAGAATC...ATATGCTTTAGGCGGATGCTAAATCGTATGGCGGATCCTAAGGCTTACGCC
                                                                    TACCGCCTAGGATTCCGAATGCGG-label H    GCAACTTCAAAGCCTTTAGCGATCAGAATC...ATATGCTTTAGGCGGATGCTAAATCGTATGGCGGATCCTAAGGCTTACGCC
                                        support          TTAGCATACCGCCTAGGATTCCGAATGCGG-label I                                        support          TTAGCATACCGCCTAGGATTCCGAATGCGG-label
```

Figure 5

A  ...ATATGCTTTAGGCGGATGCTAAATCGTATGGACAACCAGCCATTCACGGGC...
   ...TATACGAAATCCGCCTACGATTTAGCATACCTGTTGGTCGGTAAGTGCCCG...

B  ...ATATGCTTTAGGCGGATGCTAAATCGT    ATGGACAACCAGCCATTCACGGGC...
   ...TATACGAAATCCGCCTACGATTTAGCATACC    TGTTGGTCGGTAAGTGCCCG...

C  ...ATATGCTTTAGGCGGATGCTAAATCGT    ATGGCGGATCCTAAGGCTTACGCC-tag
   ...TATACGAAATCCGCCTACGATTTAGCATACC    GCCTAGGATTCCGAATGCGG D  ...ATATGCTTTAGGCGGATGCTAAATCGTATGGCGGATCCTAAGGCTTACGCC-tag
   ..TATACGAAATCCGCCTACGATTTAGCATACCGCCTAGGATTCCGAATGCGG E  ...ATATGCTTTAGGCGGATGCTAAATCGTATGGCGGATCCTAAGGCTTACGCC-tag
                                   TACCGCCTAGGATTCCGAATGCGG-label F  ...ATATGCTTTAGGCGGATGCTAAATCGTATGGCGGATCCTAAGGCTTACGCC-tag
                                   TACCGCCTAGGATTCCGAATGCGG-label G  ...ATATGCTTTAGGCGGATGCTAAATCGTATGGCGGATCCTAAGGCTTACGCC-tag
                                   TACCGCCTAGGATTCCGAATGCGG-label
                       TTAGCA
             support H  ...ATATGCTTTAGGCGGATGCTAAATCGTATGGCGGATCCTAAGGCTTACGCC-tag
                       TTAGCATACCGCCTAGGATTCCGAATGCGG-label
             support I                      TTAGCATACCGCCTAGGATTCCGAATGCGG-label
             support

SEQUENCE LISTING

<160> NUMBER OF SEQ ID NOS: 79

<210> SEQ ID NO: 1
<211> LENGTH: 28
<212> TYPE: DNA
<213> ORGANISM: Artificial Sequence
<220> FEATURE:
<223> OTHER INFORMATION: Description of Artificial Sequence: Nucleic
      Acid Fragment

<400> SEQUENCE: 1
cggtggatga cttgaagcta tgcttagg                                          28

<210> SEQ ID NO: 2
<211> LENGTH: 30
<212> TYPE: DNA
<213> ORGANISM: Artificial Sequence
<220> FEATURE:
<223> OTHER INFORMATION: Description of Artificial Sequence: Probe and
      Ligator-detector

<400> SEQUENCE: 2
tgaagctatg cggtattaca gcctattggg                                        30

<210> SEQ ID NO: 3
<211> LENGTH: 18
<212> TYPE: DNA
<213> ORGANISM: Artificial Sequence
<220> FEATURE:
<223> OTHER INFORMATION: Description of Artificial Sequence: Nucleic
      Acid Fragment
<221> NAME/KEY: misc_feature
<222> LOCATION: (6)..(8)
<223> OTHER INFORMATION: N is either A, G, C, or T

<400> SEQUENCE: 3
cctacnnnac ttcgatac                                                     18

<210> SEQ ID NO: 4
<211> LENGTH: 8
<212> TYPE: DNA
<213> ORGANISM: Artificial Sequence
<220> FEATURE:
<223> OTHER INFORMATION: Description of Artificial Sequence: Nucleic
      Acid Fragment

<400> SEQUENCE: 4 cgcatggg                                                                 8

<210> SEQ ID NO: 5
<211> LENGTH: 8
<212> TYPE: DNA
<213> ORGANISM: Artificial Sequence
<220> FEATURE:
<223> OTHER INFORMATION: Description of Artificial Sequence: Nucleic
      Acid Fragment

<400> SEQUENCE: 5 atagcttg                                                                 8

<210> SEQ ID NO: 6
<211> LENGTH: 16
<212> TYPE: DNA
<213> ORGANISM: Artificial Sequence
<220> FEATURE:
<223> OTHER INFORMATION: Description of Artificial Sequence: Nucleic Acid Fragment

<400> SEQUENCE: 6
caagctatgg atccga                                                  16

<210> SEQ ID NO: 7
<211> LENGTH: 31
<212> TYPE: DNA
<213> ORGANISM: Artificial Sequence
<220> FEATURE:
<223> OTHER INFORMATION: Description of Artificial Sequence: Nucleic
      Acid Fragment

<400> SEQUENCE: 7 caag ctatgg atctggtatt acagcctatt g                                31

<210> SEQ ID NO: 8
<211> LENGTH: 21
<212> TYPE: DNA
<213> ORGANISM: Artificial Sequence
<220> FEATURE:
<223> OTHER INFORMATION: Description of Artificial Sequence: Nucleic
      Acid Fragment

<400> SEQUENCE: 8 ccca tgtgag agatccatgg c                                           21

<210> SEQ ID NO: 9
<211> LENGTH: 6
<212> TYPE: DNA
<213> ORGANISM: Artificial Sequence
<220> FEATURE:
<223> OTHER INFORMATION: Description of Artificial Sequence: Hex

<400> SEQUENCE: 9 agctat                                                              6

<210> SEQ ID NO: 10
<211> LENGTH:: 4
<212> TYPE: DNA
<213> ORGANISM: Artificial Sequence
<220> FEATURE:
<223> OTHER INFORMATION: Description of Artificial Sequence: Recognition

<400> SEQUENCE: 10 tcga                                                                4

<210> SEQ ID NO: 11
<211> LENGTH: 4
<212> TYPE: DNA
<213> ORGANISM: Artificial Sequence
<220> FEATURE:
<223> OTHER INFORMATION: Description of Artificial Sequence: Recognition
      Site

<400> SEQUENCE: 11 gtac                                                                4

<210> SEQ ID NO: 12
<211> LENGTH: 12
<212> TYPE: DNA
<213> ORGANISM: Artificial Sequence
<220> FEATURE:
<223> OTHER INFORMATION: Description of Artificial Sequence: Nucleic
      Acid Fragment

```
<400> SEQUENCE: 12
tcgataccta gg                                                              12

<210> SEQ ID NO: 13
<211> LENGTH: 30
<212> TYPE: DNA
<213> ORGANISM: Artificial Sequence
<220> FEATURE:
<223> OTHER INFORMATION: Description of Artificial Sequence:
      adaptor-indexer
<221> NAME/KEY: misc_feature
<222> LOCATION: (1)..(10)
<223> OTHER INFORMATION: N is either A, G, C, or T
<221> NAME/KEY: misc_feature
<222> LOCATION: (16)..(30)
<223> OTHER INFORMATION: N is either A, G, C, or T

<400> SEQUENCE: 13
nnnnnnnnnn ggatgnnnnn nnnnnnnnnn                                           30

<210> SEQ ID NO: 14
<211> LENGTH: 16
<212> TYPE: DNA
<213> ORGANISM: Artificial Sequence
<220> FEATURE:
<223> OTHER INFORMATION: Description of Artificial Sequence:
      Adaptor-indexer
<221> NAME/KEY: misc_feature
<222> LOCATION: (1)..(3)
<223> OTHER INFORMATION: N is either A, G, C, or T
<221> NAME/KEY: misc_feature
<222> LOCATION: (8)..(16)
<223> OTHER INFORMATION: N is either A, G, C, or T

<400> SEQUENCE: 14
nnngcgcnnn nnnnnn                                                          16

<210> SEQ ID NO: 15
<211> LENGTH: 16
<212> TYPE: DNA
<213> ORGANISM: Artificial Sequence
<220> FEATURE:
<223> OTHER INFORMATION: Description of Artificial Sequence:
      Adaptor-indexer
<221> NAME/KEY: modified_base
<222> LOCATION: (5)
<223> OTHER INFORMATION: Methylated cytosine
<221> NAME/KEY: misc_feature
<222> LOCATION: (1)..(3)
<223> OTHER INFORMATION: N is either A, G, C, or T
<221> NAME/KEY: misc_feature
<222> LOCATION: (8)..(16)
<223> OTHER INFORMATION: N is either A, G, C, or T

<400> SEQUENCE: 15
nnngcgcnnn nnnnnn                                                          16

<210> SEQ ID NO: 16
<211> LENGTH: 20
<212> TYPE: DNA
<213> ORGANISM: Artificial Sequence
<220> FEATURE:
<223> OTHER INFORMATION: Description of Artificial Sequence:
      Adaptor-indexer
<221> NAME/KEY: misc_feature
<222> LOCATION: (1)..(14)
<223> OTHER INFORMATION: N is either A, G, C, or T
<221> NAME/KEY: misc_feature
<222> LOCATION: (19)..(20)
<223> OTHER INFORMATION: N is either A, G, C, or T
```

```
<400> SEQUENCE: 16
nnnnnnnnnn nnnctaccnn                                              20

<210> SEQ ID NO: 17
<211> LENGTH: 28
<212> TYPE: DNA
<213> ORGANISM: Artificial Sequence
<220> FEATURE:
<223> OTHER INFORMATION: Description of Artificial Sequence: cDNA target
<221> NAME/KEY: misc_feature
<222> LOCATION: (14)..(19)
<223> OTHER INFORMATION: N is either A, G, C, or T

<400> SEQUENCE: 17
gatctagatc agtnnnnnnt gaccatgt                                     28

<210> SEQ ID NO: 18
<211> LENGTH: 11
<212> TYPE: DNA
<213> ORGANISM: Artificial Sequence
<220> FEATURE:
<223> OTHER INFORMATION: Description of Artificial Sequence: Primer

<400> SEQUENCE: 18
cgtgaatcat g                                                       11

<210> SEQ ID NO: 19
<211> LENGTH: 28
<212> TYPE: DNA
<213> ORGANISM: Artificial Sequence
<220> FEATURE:
<223> OTHER INFORMATION: Description of Artificial Sequence: cDNA
      Amplicon
<221> NAME/KEY: misc_feature
<222> LOCATION: (14)..(19)
<223> OTHER INFORMATION: N is either A, G, C, or T

<400> SEQUENCE: 19
gatctggatg agtnnnnnnt gaccatgt                                     28

<210> SEQ ID NO: 20
<211> LENGTH: 34
<212> TYPE: DNA
<213> ORGANISM: Artificial Sequence
<220> FEATURE:
<223> OTHER INFORMATION: Description of Artificial Sequence: amplicon
<221> NAME/KEY: misc_feature
<222> LOCATION: (14)..(19)
<223> OTHER INFORMATION: N is either A, G, C, or T
<221> NAME/KEY: misc_feature
<222> LOCATION: (24)..(34)
<223> OTHER INFORMATION: N is either A, G, C, or T

<400> SEQUENCE: 20
gatctggatg agtnnnnnnt gacnnnnnnn nnnn                              34

<210> SEQ ID NO: 21
<211> LENGTH: 28
<212> TYPE: DNA
<213> ORGANISM: Artificial Sequence
<220> FEATURE:
<221> NAME/KEY: misc_feature
<222> LOCATION: (14)..(19)
<223> OTHER INFORMATION: N is either A, G, C, or T
<223> OTHER INFORMATION: Description of Artificial Sequence: amplicon

<400> SEQUENCE: 21
gatctagatc agtnnnnnnt gaccatgt                                     28
```

<210> SEQ ID NO: 22
<211> LENGTH: 28
<212> TYPE: DNA
<213> ORGANISM: Artificial Sequence
<220> FEATURE:
<223> OTHER INFORMATION: Description of Artificial Sequence: amplicon
<221> NAME/KEY: misc_feature
<222> LOCATION: (14)..(19)
<223> OTHER INFORMATION: N is either A, G, C, or T

<400> SEQUENCE: 22
gatctagatc agtnnnnnna ctgatcgg                28

<210> SEQ ID NO: 23
<211> LENGTH: 28
<212> TYPE: DNA
<213> ORGANISM: Artificial Sequence
<220> FEATURE:
<223> OTHER INFORMATION: Description of Artificial Sequence: amplicon
<221> NAME/KEY: misc_feature
<222> LOCATION: (14)..(19)
<223> OTHER INFORMATION: N is either A, G, C, or T

<400> SEQUENCE: 23
gttatactgc aacnnnnnnt gaccatgt                28

<210> SEQ ID NO: 24
<211> LENGTH: 28
<212> TYPE: DNA
<213> ORGANISM: Artificial Sequence
<220> FEATURE:
<223> OTHER INFORMATION: Description of Artificial Sequence: amplicon
<221> NAME/KEY: misc_feature
<222> LOCATION: (14)..(19)
<223> OTHER INFORMATION: N is either A, G, C, or T

<400> SEQUENCE: 24
gatctagatc agtnnnnnnt gaccatgt                28

<210> SEQ ID NO: 25
<211> LENGTH: 6
<212> TYPE: DNA
<213> ORGANISM: Artificial Sequence
<220> FEATURE:
<223> OTHER INFORMATION: Description of Artificial Sequence: BamHI

<400> SEQUENCE: 25 ggatcc                                         6

<210> SEQ ID NO: 26
<211> LENGTH: 6
<212> TYPE: DNA
<213> ORGANISM: Artificial Sequence
<220> FEATURE:
<223> OTHER INFORMATION: Description of Artificial Sequence: BclI

<400> SEQUENCE: 26 tgatca                                         6

<210> SEQ ID NO: 27
<211> LENGTH: 6
<212> TYPE: DNA
<213> ORGANISM: Artificial Sequence
<220> FEATURE:
<223> OTHER INFORMATION: Description of Artificial Sequence: BglII

<400> SEQUENCE: 27 agatct                                                          6

<210> SEQ ID NO: 28
<211> LENGTH: 6
<212> TYPE: DNA
<213> ORGANISM: Artificial Sequence
<220> FEATURE:
<223> OTHER INFORMATION: Description of Artificial Sequence: BsiWI

<400> SEQUENCE: 28 cgtacg                                                          6

<210> SEQ ID NO: 29
<211> LENGTH: 6
<212> TYPE: DNA
<213> ORGANISM: Artificial Sequence
<220> FEATURE:
<223> OTHER INFORMATION: Description of Artificial Sequence: BspHI

<400> SEQUENCE: 29 tcatga                                                          6

<210> SEQ ID NO: 30
<211> LENGTH: 6
<212> TYPE: DNA
<213> ORGANISM: Artificial Sequence
<220> FEATURE:
<223> OTHER INFORMATION: Description of Artificial Sequence: EcoRI

<400> SEQUENCE: 30 gaattc                                                          6

<210> SEQ ID NO: 31
<211> LENGTH: 4
<212> TYPE: DNA
<213> ORGANISM: Artificial Sequence
<220> FEATURE:
<223> OTHER INFORMATION: Description of Artificial Sequence: AciI

<400> SEQUENCE: 31 ccgc                                                            4

<210> SEQ ID NO: 32
<211> LENGTH: 4
<212> TYPE: DNA
<213> ORGANISM: Artificial Sequence
<220> FEATURE:
<223> OTHER INFORMATION: Description of Artificial Sequence: Hha I

<400> SEQUENCE: 32 gcgc                                                            4

<210> SEQ ID NO: 33
<211> LENGTH: 4
<212> TYPE: DNA
<213> ORGANISM: Artificial Sequence
<220> FEATURE:
<223> OTHER INFORMATION: Description of Artificial Sequence: Sau3AI

<400> SEQUENCE: 33 gatc                                                            4

<210> SEQ ID NO: 34
<211> LENGTH: 4
<212> TYPE: DNA

```
<213> ORGANISM: Artificial Sequence
<220> FEATURE:
<223> OTHER INFORMATION: Description of Artificial Sequence: Tsp509I

<400> SEQUENCE: 34 aatt                                                                      4

<210> SEQ ID NO: 35
<211> LENGTH: 4
<212> TYPE: DNA
<213> ORGANISM: Artificial Sequence
<220> FEATURE:
<223> OTHER INFORMATION: Description of Artificial Sequence: TaiI

<400> SEQUENCE: 35 acgt                                                                      4

<210> SEQ ID NO: 36
<211> LENGTH: 24
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 36
catgcggatc ctaaggctta cgcc                                               24

<210> SEQ ID NO: 37
<211> LENGTH: 23
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 37
catgcggatc ctaaggctta cgc                                                23

<210> SEQ ID NO: 38
<211> LENGTH: 20
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 38
catgcggatc ctaaggctta                                                    20

<210> SEQ ID NO: 39
<211> LENGTH: 17
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 39
catgcggatc ctaaggc                                                       17

<210> SEQ ID NO: 40
<211> LENGTH: 23
<212> TYPE: DNA
<213> ORGANISM: Artificial Sequence
<220> FEATURE:
<223> OTHER INFORMATION: Description of Artificial Sequence:
```

Ligator-detector

<400> SEQUENCE: 40
atgcggatcc taaggcttac gcc                                              23

<210> SEQ ID NO: 41
<211> LENGTH: 22
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 41
tgcggatcct aaggcttacg cc                                               22

<210> SEQ ID NO: 42
<211> LENGTH: 21
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 42
gcggatccta aggcttacgc c                                                21

<210> SEQ ID NO: 43
<211> LENGTH: 22
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 43
atgcggatcc taaggcttac gc                                               22

<210> SEQ ID NO: 44
<211> LENGTH: 21
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 44
atgcggatcc taaggcttac g                                                21

<210> SEQ ID NO: 45
<211> LENGTH: 18
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 45
atgcggatcc taaggctt                                                    18

<210> SEQ ID NO: 46
<211> LENGTH: 16
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 46
atgcggatcc taaggc 16

<210> SEQ ID NO: 47
<211> LENGTH: 19
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 47
tgcggatcct aaggcttac 19

<210> SEQ ID NO: 48
<211> LENGTH: 24
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 48
ggcgtaagcc ttaggatccg catc 24

<210> SEQ ID NO: 49
<211> LENGTH: 23
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 49
gcgtaagcct taggatccgc atc 23

<210> SEQ ID NO: 50
<211> LENGTH: 21
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 50
gtaagcctta ggatccgcat c 21

<210> SEQ ID NO: 51
<211> LENGTH: 16
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 51
ccttaggatc cgcatc 16

<210> SEQ ID NO: 52
<211> LENGTH: 23
<212> TYPE: DNA
<213> ORGANISM: Artificial Sequence
<220> FEATURE:
<223> OTHER INFORMATION: Description of Artificial Sequence:
      Ligator-detector

```
<400> SEQUENCE: 52
ggcgtaagcc ttaggatccg cat                                              23

<210> SEQ ID NO: 53
<211> LENGTH: 22
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 53
ggcgtaagcc ttaggatccg ca                                               22

<210> SEQ ID NO: 54
<211> LENGTH: 21
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 54
ggcgtaagcc ttaggatccg c                                                21

<210> SEQ ID NO: 55
<211> LENGTH: 25
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 55
gcatgcggat cctaaggctt acgcc                                            25

<210> SEQ ID NO: 56
<211> LENGTH: 24
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 56
caagtaatgg aagctggatt cgcg                                             24

<210> SEQ ID NO: 57
<211> LENGTH: 23
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 57
caagtaatgg aagctggatt cgc                                              23

<210> SEQ ID NO: 58
<211> LENGTH: 21
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 58
```
caagtaatgg aagctggatt c                                    21

<210> SEQ ID NO: 59
<211> LENGTH: 15
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 59
caagtaatgg aagct                                           15

<210> SEQ ID NO: 60
<211> LENGTH: 23
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 60
aagtaatgga agctggattc gcg                                  23

<210> SEQ ID NO: 61
<211> LENGTH: 22
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 61
agtaatggaa gctggattcg cg                                   22

<210> SEQ ID NO: 62
<211> LENGTH: 21
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 62
gtaatggaag ctggattcgc g                                    21

<210> SEQ ID NO: 63
<211> LENGTH: 22
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 63
aagtaatgga agctggattc gc                                   22

<210> SEQ ID NO: 64
<211> LENGTH: 20
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 64
aagtaatgga agctggattc                                              20

<210> SEQ ID NO: 65
<211> LENGTH: 18
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 65
aagtaatgga agctggat                                                18

<210> SEQ ID NO: 66
<211> LENGTH: 15
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 66
aagtaatgga agctg                                                   15

<210> SEQ ID NO: 67
<211> LENGTH: 22
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 67
agtaatggaa gctggattcg cg                                           22

<210> SEQ ID NO: 68
<211> LENGTH: 24
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 68
cgcgaatcca gcttccatta cttg                                         24

<210> SEQ ID NO: 69
<211> LENGTH: 23
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 69
gcgaatccag cttccattac ttg                                          23

<210> SEQ ID NO: 70
<211> LENGTH: 21
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 70
gaatccagct tccattactt g                                            21

<210> SEQ ID NO: 71
<211> LENGTH: 16
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 71
cagcttccat tacttg                                                         16

<210> SEQ ID NO: 72
<211> LENGTH: 23
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 72
cgcgaatcca gcttccatta ctt                                                 23

<210> SEQ ID NO: 73
<211> LENGTH: 22
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 73
cgcgaatcca gcttccatta ct                                                  22

<210> SEQ ID NO: 74
<211> LENGTH: 21
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 74
cgcgaatcca gcttccatta c                                                   21

<210> SEQ ID NO: 75
<211> LENGTH: 20
<212> TYPE: DNA
<213> ORGANISM: Artificial Sequence
<220> FEATURE:
<223> OTHER INFORMATION: Description of Artificial Sequence:
      Ligator-detector

<400> SEQUENCE: 75
gaatccagct tccattactt                                                     20

<210> SEQ ID NO: 76
<211> LENGTH: 51
<212> TYPE: DNA
<213> ORGANISM: Artificial Sequence
<220> FEATURE:
<223> OTHER INFORMATION: Description of Artificial Sequence: Nucleic
      Acid Fragment

<400> SEQUENCE: 76
atatgcttta ggcggatgct aaatcgtatg gacaaccagc cattcacggg c                  51

```
<210> SEQ ID NO: 77
<211> LENGTH: 51
<212> TYPE: DNA
<213> ORGANISM: Artificial Sequence
<220> FEATURE:
<223> OTHER INFORMATION: Description of Artificial Sequence: Nucleic
      Acid Fragment

<400> SEQUENCE: 77
atatgcttta ggcggatgct aaatcgtatg gcggatccta aggcttacgc c            51

<210> SEQ ID NO: 78
<211> LENGTH: 15
<212> TYPE: DNA
<213> ORGANISM: Artificial Sequence
<220> FEATURE:
<223> OTHER INFORMATION: Description of Artificial Sequence: Nucleic
      Acid Fragment

<400> SEQUENCE: 78
tccctgatca gaatc                                                    15

<210> SEQ ID NO: 79
<211> LENGTH: 30
<212> TYPE: DNA
<213> ORGANISM: Artificial Sequence
<220> FEATURE:
<223> OTHER INFORMATION: Description of Artificial Sequence: Nucleic
      Acid Fragment

<400> SEQUENCE: 79
gcaacttcaa agcctttagc gatcagaatc                                    30
```

FIXED ADDRESS ANALYSIS OF SEQUENCE TAGS

CROSS-REFERENCE TO RELATED APPLICATIONS

This application claims benefit of U.S. Provisional Application No. 60/127,932, filed Apr. 6, 1999. Application Ser. No. 60/127,932, filed Apr. 6, 1999, is hereby incorporated herein by reference.

BACKGROUND OF THE INVENTION

The disclosed invention is generally in the field of nucleic acid characterization and analysis, and specifically in the area of analysis and comparison of gene expression patterns and genomes.

The study of differences in gene-expression patterns is one of the most promising approaches for understanding mechanisms of differentiation and development. In addition, the identification of disease-related target molecules opens new avenues for rational pharmaceutical intervention. Currently, there are two main approaches to the analysis of molecular expression patterns: (1) the generation of mRNA-expression maps and (2) examination of the 'proteome', in which the expression profile of proteins is analyzed by techniques such as two-dimensional gel electrophoresis, mass spectrometry [matrix-assisted-desorption-ionization-time-of-flight (MALDI-TOF) or electrospray] and by the ability to sequence sub-picomole amounts of protein. Classical approaches to transcript imaging, such as northern blotting or plaque hybridization, are time-consuming and material-intensive ways to analyze mRNA-expression patterns. For these reasons, other methods for high-throughput screening in industrial and clinical research have been developed.

A breakthrough in the analysis of gene expression was the development of the northern-blot technique in 1977 (Alwine et al., *Proc. Natl. Acad. Sci. U.S.A.* 74:5350–5354 (1977)). With this technique, labeled cDNA or RNA probes are hybridized to RNA blots to study the expression patterns of mRNA transcripts. Alternatively, RNase-protection assays can detect the expression of specific RNAs. These assays allow the expression of mRNA subsets to be determined in a parallel manner. For RNase-protection assays, the sequence of the analyzed mRNA has to be known in order to synthesize a labeled cDNA that forms a hybrid with the selected mRNA; such hybrids resist RNA degradation by a single-strand-specific nuclease and can be detected by gel electrophoresis. As a third approach, differential plaque-filter hybridization allows the identification of specific differences in the expression of cloned cDNAs (Maniatis et al. *Cell* 15:687–701 (1978)). Although all of these techniques are excellent tools for studying differences in gene expression, the limiting factor of these classical methods is that expression patterns can be analyzed only for known genes.

The analysis of gene-expression patterns made a significant advance with the development of subtractive cDNA libraries, which are generated by hybridizing an mRNA pool of one origin to an mRNA pool of a different origin. Transcripts that do not find a complementary strand in the hybridization step are then used for the construction of a cDNA library (Hedrick et al., *Nature* 308:149–153 (1984)). A variety of refinements to this method have been developed to identify specific mRNAs (Swaroop et al., *Nucleic Acids Res.* 25:1954 (1991); Diatchenko et al, *Proc. Natl. Acad. Sci. U.S.A* 93:6025–6030 (1996)). One of these is the selective amplification of differentially expressed mRNAs via biotin- and restriction-mediated enrichment (SABRE; Lavery et al., *Proc. Natl. Acad. Sci. U.S.A.* 94:6831–6836 (1997)), cDNAs derived from a tester population are hybridized against the cDNAs of a driver (control) population. After a purification step specific for tester-cDNA-containing hybrids, tester—tester homohybrids are specifically amplified using an added linker, thus allowing the isolation of previously unknown genes.

The technique of differential display of eukaryotic mRNA was the first one-tube method to analyze and compare transcribed genes systematically in a bi-directional fashion; subtractive and differential hybridization techniques have only been adapted for the unidirectional identification of differentially expressed genes (Liang and Pardee, *Science* 257:967–971 (1992)). Refinements have been proposed to strengthen reproducibility, efficiency, and performance of differential display (Bauer et al., *Nucleic Acids Res.* 11:4272–4280 (1993); Liang and Pardee, *Curr. Opin. Immunol* 7:274–280 (1995); Ito and Sakaki, *Methods Mol. Biol.* 85:37–44 (1997); Praschar and Weissman, *Proc. Natl. Acad. Sci U.S.A.* 93;659–663 (1996)). Although these approaches are more reproducible and precise than traditional PCR-based differential display, they still require the use of gel electrophoresis, and often implies the exclusion of certain DNA fragments from analysis.

Originally developed to identify differences between two complex genomes, representational difference analysis (RDA) was adapted to analyze differential gene expression by taking advantage of both subtractive hybridization and PCR (Lisitsyn et al., *Science* 259:946–951 (1993); Hubank and Schatz, *Nucleic Acids Res.* 22:5640–5648 (1994)). In the first step, mRNA derived from two different populations, the tester and the driver (control), is reverse transcribed; the tester cDNA represents the cDNA population in which differential gene expression is expected to occur. Following digestion with a frequently cutting restriction endonuclease, linkers are ligated to both ends of the cDNA. A PCR step then generates the initial representation of the different gene pools. The linkers of the tester and driver cDNA are digested and a new linker is ligated to the ends of the tester cDNA. The tester and driver cDNAs are then mixed in a 1:100 ratio with an excess of driver cDNA in order to promote hybridization between single-stranded cDNAs common in both tester and driver cDNA pools. Following hybridization of the cDNAs, a PCR exponentially amplifies only those homoduplexes generated by the tester cDNA, via the priming sites on both ends of the double-stranded cDNA (O'Neill and Sinclair, *Nucleic Acids Res.* 25:2681–2682 (1997); Wada et al., *Kidney Int.* 51:1629–1638 (1997); Edman et al., *J.* 323:113–118 (1997)).

The gene-expression pattern of a cell or organism determines its basic biological characteristics. In order to accelerate the discovery and characterization of mRNA-encoding sequences, the idea emerged to sequence fragments of cDNA randomly, direct from a variety of tissues (Adams et al., *Science* 252:1651–1656 (1991); Adams et al., *Nature* 377:3–16 (1995)). These expressed sequence tags (ESTs) allow the identification of coding regions in genome-derived sequences. Publicly available EST databases allow the comparative analysis of gene expression by computer. Differentially expressed genes can be identified by comparing the databases of expressed sequence tags of a given organ or cell type with sequence information from a different origin (Lee et al., *Proc. Natl. Acad. Sci. U.S.A.* 92:8303–8307 (1995); Vasmatzis et al., *Proc. Natl. Acad. Sci. U.S.A.* 95:300–304 (1998)). A drawback to sequencing of ESTs is the requirement for large-scale sequencing facilities.

Serial analysis of gene expression (SAGE) is a sequence-based approach to the identification of differentially expressed genes through comparative analyses (Velculescu et al., *Science* 270:484–487 (1995)). It allows the simultaneous analysis of sequences that derive from different cell population or tissues. Three steps form the molecular basis for SAGE: (1) generation of a sequence tag (10–14 bp) to identify expressed transcripts; (2) ligation of sequence tags to obtain concatemers that can be cloned and sequenced; and (3) comparison of the sequence data to determine differences in expression of genes that have been identified by the tags. This procedure is performed for every mRNA population to be analyzed. A major drawback of SAGE is the fact that corresponding genes can be identified only for those tags that are deposited in gene banks, thus making the efficiency of SAGE dependent on the extent of available databases. Alternatively, a major sequencing effort is required to complete a SAGE data set capable of providing 95% coverage of any given mRNA population, simply because most of the sequencing work yields repetitive reads on those tags that are present in high frequency in cellular mRNA. In other words, SAGE sequencing experiments yield diminishing returns for rare mRNAs, whose unique tags will begin to accumulate in the database only after many weeks of sequencing effort.

A different approach to the study of gene-expression profiles and genome composition is the use of DNA microarrays. Current DNA microarrays are systematically gridded at high density. Such microarrays are generated by using cDNAs (for example, ESTs), PCR products or cloned DNA, which are linked to the surface of nylon filters, glass slides or silicon chips (Schena et al., *Science* 270, 467–470 (1995)). DNA arrays can also be assembled from synthetic oligonucleotides, either by directly applying the synthesized oligonucleotides, either by directly applying the synthesized oligonucleotides to the matrix or by a more sophisticated method that combines photolithography and solid-phase chemical synthesis (Fodor et al., *Nature* 364:555–556 (1993)). To determine differences in gene-expression, labeled cDNAs or oligonucleotides are hybridized to the DNA- or oligomer-carrying arrays. When using different fluorophores for labeling cDNAs or oligonucleotides, two probes can be applied simultaneously to the array and compared at different wavelengths. The expression of 10,000 genes and more can be analyzed on a single chip (Chee et al., *Science* 274:610–614 (1996)). However, depending on the sensitivity of both cDNA and oligonucleotide arrays, the intensity of hybridization signals can leave the linear range when either weakly or abundantly expressed genes are analyzed. Thus, individual optimization steps are required to ensure the accurate detection of differentially expressed genes. While such microarray methods may be used to address a number of interesting biological questions, they are not suitable for the discovery of new genes.

There is a need for a method that combines the power and convenience of array hybridization technology with the capability for gene discovery inherent in differential display or SAGE. Such a method would be most attractive if it could enable comprehensive gene expression analysis without the use of gel electrophoresis, and without the need for a redundant DNA sequencing effort.

Therefore, it is an object of the present invention to provide a method for the comprehensive analysis of nucleic acid sequence tags.

It is another object of the present invention to provide a detector composition that allows indexing of nucleic acid sequence tags.

BRIEF SUMMARY OF THE INVENTION

Disclosed is a method for the comprehensive analysis of nucleic acid samples and a detector composition for use in the method. The method, referred to as Fixed Address Analysis of Sequence Tags (FAAST), involves generation of a set of nucleic acid fragments having a variety of sticky end sequences; indexing of the fragments into sets based on the sequence of sticky ends; associating a detector sequence with the fragments; sequence-based capture of the indexed fragments on a detector array; and detection of the fragment labels. Generation of the multiple sticky end sequences is accomplished by incubating the nucleic acid sample with one or more nucleic acid cleaving reagents. Preferably this is accomplished by subjecting the nucleic acid sample to digestion by a restriction endonuclease that cleaves at a site different from the recognition sequence, or by multiple restriction endonucleases. The indexed fragments are captured by hybridization and coupling, preferably by ligation, to a probe. The probe is preferably immobilized in an array or on sortable beads.

The method allows detection of the indexed fragments where detection provides some sequence information for the fragments including the sequence of the original sticky end of each fragment, the recognition sequence of the restriction endonuclease (if different from the sticky end sequence), and the sequence corresponding to the probe. The method allows a complex sample of nucleic acid to be cataloged quickly and easily in a reproducible and sequence-specific manner.

One form of the FAAST method, referred to as variable address analysis of sequence tags (VAAST) allows determination of associations, in a nucleic acid molecule, of different combinations of known or potential sequences. For example, particular combinations of joining and variable regions in immunoglobulins or T cell receptors can be determined. Another form of the FAAST method, referred to as modification assisted analysis of sequence tags (MAAST), assesses modification of sequences in nucleic acid molecules by basing cleavage of the molecules on the presence or absence of modification. For example, a site that is methylated in a nucleic acid molecule will not be cut by a restriction enzyme that is sensitive to methylation at that site. A restriction enzyme that is insensitive to methylation will cleave at that site, thus producing a different pattern of sequence tags.

BRIEF DESCRIPTION OF THE DRAWINGS

FIG. 1 is a listing of examples of ligator-detectors (numbered sequences SEQ ID NOS:36–75) designed for use with one of two example adaptor-indexers (top SEQ ID NO:36 and bases 5–24 of SEQ ID NO:56). The sticky end sequences (or their complements) are shown in bold.

FIG. 2 is a list of nucleic acid molecules used and formed during an example of the disclosed method focused on a single example nucleic acid molecule (panel A SEQ ID NO:76). The restriction enzyme recognition sequence is underlined and the sticky end sequence is in bold. Panel B (bases 1–27 and 28–51 of SEQ ID NO:76) shows the nucleic acid molecule after cleavage with FokI. Panel C (bases 1–27 and 28–51 of SEQ ID NO:77) shows the nucleic acid fragment (left) and an example of a compatible adaptor-indexer (right; this is adaptor-indexer I from FIG. 1). Panel D (SEQ ID NO:77) shows the adaptor-indexer ligated to the nucleic acid fragment. Panel E (SEQ ID NO:77) shows one strand (the top strand) of the adaptor/fragment (top) and an example of a compatible ligator-detector (bottom; this is ligator-detector 13 from FIG. 1). Panel F (SEQ ID NO:77)

shows the ligator-detector hybridized to the adaptor/fragment strand. Panel G (SEQ ID NO:77) shows the adaptor/fragment/ligator (top) and a compatible hexamer detector array probe (bottom) immobilized on a detector array. Panel H (SEQ ID NO:77) shows the detector array probe ligated to the ligator-detector (both hybridized to the adaptor/fragment). Panel I (complementary bases 22–51 of SEQ ID NO:77) show the ligated probe/ligator-detector, which is immobilized on the detector array.

FIG. 3 is a list of nucleic acid molecules used and formed during an example of the disclosed method focused on a single example nucleic acid molecule (panel A (SEQ ID NO:76)). In this example, the bottom strand of the nucleic acid molecule is used. The restriction enzyme recognition sequence is underlined and the sticky end sequence is in bold. Panel B (bases 1–27 and 28–51 of SEQ ID NO:76) shows the nucleic acid molecule after cleavage with FokI. Panel C (bases 1–27 and 28–51 of SEQ ID NO:76) shows the nucleic acid fragment (left) and an example of a compatible adaptor-indexer (right; this is adaptor-indexer I from FIG. 1). Panel D (SEQ ID NO:77) shows the adaptor-indexer ligated to the nucleic acid fragment. Panel E (bases 28–51 and complementary bases of SEQ ID NO:77) shows the bottom strand of the adaptor/fragment (top) and an example of a compatible ligator-detector (bottom; this is ligator-detector 1 from FIG. 1). Panel F (bases 28–51 and complementary bases of SEQ ID NO:77) shows the ligator-detector hybridized to the adaptor/fragment strand. Panel G (bases 22–27, bases 28–51, and complementary bases of SEQ ID NO:77) shows the adaptor/fragment/ligator (top) and a compatible hexamer detector array probe (bottom) immobilized on a detector array. Panel H (bases 22–51 and complementary bases of SEQ ID NO:77) shows the detector array probe ligated to the ligator-detector (both hybridized to the adaptor/fragment). Panel I (bases 22–51 of SEQ ID NO:77) show the ligated probe/ligator-detector, which is immobilized on the detector array.

FIG. 4 is a list of nucleic acid molecules used and formed during an example of the disclosed method focused on a single example nucleic acid molecule (panel A (SEQ ID NOS:78 & 76)). This is the same as the example in FIG. 2 except the addition of a second adaptor is illustrated. The restriction enzyme recognition sequence is underlined and the sticky end sequences are in bold. Panel D (SEQ ID NOS:78 & 77) shows the adaptor-indexer ligated to the nucleic acid fragment. Panel D1 (bases 1–5 and 6–15 of SEQ ID NO:78 and SEQ ID NO:77) shows the nucleic acid molecule after cleavage with Sau3AI. Panel D2 (bases 1–20 and 21–30 of SEQ ID NO:79 & 77) shows the nucleic acid fragment (right) and an example of a compatible second adaptor (left). Panel D3 (SEQ ID NOS:79 & 77) shows the second adaptor ligated to the nucleic acid fragment (the adaptor-indexer is ligated to the other end of the fragment). Panel F (SEQ ID NOS:79 & 77) shows a ligator-detector hybridized to a strand of the adaptor/fragment. Panel H (SEQ ID NOS:79 & 77) shows a detector array probe ligated to the ligator-detector (both hybridized to the adaptor/fragment). Panel I show (complementary bases 22–51 of SEQ ID NO:77) the ligated probe/ligator-detector, which is immobilized on the detector array.

FIG. 5 is a list of nucleic acid molecules used and formed during an example of the disclosed method focused on a single example nucleic acid molecule (panel A (SEQ ID NO:76)). This is the same as the example in FIG. 2 except the addition of a capture tag is illustrated. The restriction enzyme recognition sequence is underlined and the sticky end sequence is in bold. Panel B (bases 1–27 and 28–51 of SEQ ID NO:76) shows the nucleic acid molecule after cleavage with FokI. Panel C (bases 1–27 and 28–51 of SEQ ID NO:77) shows the nucleic acid fragment (left) and an example of a compatible adaptor-indexer (right; this is adaptor-indexer I from FIG. 1). The adaptor-indexer includes a capture tag (tag). Panel D (SEQ ID NO:77) shows the adaptor-indexer ligated to the nucleic acid fragment. Panel E (SEQ ID NO:77) shows one strand (the top strand) of the adaptor/fragment (top) and an example of a compatible ligator-detector (bottom; this is ligator-detector 13 from FIG. 1). Separation of the strands can be facilitated by the capture tag. Panel F (SEQ ID NO:77) shows the ligator-detector hybridized to the adaptor/fragment strand. Panel G (SEQ ID NO:77) shows the adaptor/fragment/ligator (top) and a compatible hexamer detector array probe (bottom) immobilized on a detector array. Panel H (SEQ ID NO:77) shows the detector array probe ligated to the ligator-detector (both hybridized to the adaptor/fragment). Panel I (complementary bases 22–51 of SEQ ID NO:77) show the ligated probe/ligator-detector, which is immobilized on the detector array.

DETAILED DESCRIPTION OF THE INVENTION

The disclosed method, referred to as Fixed Address Analysis of Sequence Tags (FAAST), allows a complex sample of nucleic acid to be quickly and easily cataloged in a reproducible and sequence-specific manner. Such a catalog can be compared with other, similarly prepared catalogs of other nucleic acid samples to allow convenient detection of differences between the samples. The catalogs, which incorporate a significant amount of information about the nucleic acid samples, can serve as fingerprints of the nucleic acid samples which can be used both for detection of related nucleic acid samples and comparison of nucleic acid samples. For example, the presence or identity of specific organisms can be detected by producing a catalog of nucleic acid of the test organism and comparing the resulting catalog with reference catalogs prepared from known organisms. Changes and differences in gene expression patterns can also be detected by preparing catalogs of mRNA from different cell samples and comparing the catalogs. The catalog of sequences can also be used to produce a set of probes or primers that is specific for the source of a nucleic acid sample.

Comparison of nucleic acid catalogs produced with the disclosed method is facilitated by the highly ordered nature of the sequence information produced and cataloged in the method. Use of immobilization, sorting, and/or array detection in the method allows automation of the method, the cataloging of the information, and comparisons to other catalogs. The method results in the equivalent of a large number of sequence-specific bins that can be filled, empty, or filled to different levels, with the pattern of filled and empty bins, and/or of the amount of signal in a bin, providing information about the nucleic acid sample that has been cataloged.

The FAAST method involves the following basic steps. A nucleic acid sample is incubated with one or more nucleic acid cleaving reagents, preferably restriction endonucleases, that results in a set of DNA fragments having sticky ends with a variety of sequences. In a preferred form of the method, the sample can be divided into aliquots (referred to as index samples); preferably as many aliquots as there are sticky end sequences. Where multiple restriction endonucleases are used, the nucleic acid sample is preferably divided into index samples before cleavage. Where a single restriction endonuclease is used, the nucleic acid sample is preferably divided into index samples following cleavage. Each sample (each index sample if the nucleic acid sample was divided) is then mixed with one or more adaptor-indexers, each of which has a sticky end compatible with one of the possible sticky ends on the DNA fragments in that index sample. It is preferred that a different adaptor-indexer be mixed with each index sample. The adaptor-indexes are then covalently coupled, preferably by ligation, onto compatible DNA fragments.

The DNA fragments in each sample (or each index sample) are then hybridized to ligator-detectors. One end of each ligator-detector has sequence matching or complementary to all or part of one of the possible sticky end sequences generated by the first nucleic acid cleaving reagent(s), or all or part of the recognition sequence of the first nucleic acid cleaving reagent(s) when cleavage is not offset from the recognition sequence. The ligator-detector can, and preferably does, have sequence matching or complementary to sequence adjacent to the sticky end sequence in the fragment coupled to the adaptor-indexer. The ligator-detector used in each index sample preferably matches or is complementary to sequence, including sticky end sequence, in the adaptor-indexer sequence used in that index sample.

Finally, each sample (or index sample) is reacted with and coupled, preferably by ligation, to one or more detector probes. Preferably, the set of detector probes used include every possible sequence of a given length (for example, every possible six base sequence). The ends of the probes and the ligator-detector oligonucleotides are coupled only if the probe hybridizes adjacent to the end of the ligator-adaptor. The probes are preferably immobilized oligonucleotides.

Each processed DNA fragment from the sample will result in a signal based on coupling of the ligator-detector to a probe. A complex nucleic acid sample will produce a unique pattern of signals. It is this pattern that allows unique cataloging of nucleic acid samples and sensitive and powerful comparisons of the patterns of signals produced from different nucleic acid samples.

Coupling of ligator-detectors to probes can be detected directly or indirectly. For example, any of the probe, the ligator-detector, or the associated adaptor-indexer can be detected. Association of a ligator-detector or adaptor-indexer with a given probe is indicative of coupling of the probe and ligator-detector. Detection of such associations can be facilitated through immobilization of the probes, detector-ligators, or adaptor-indexers, and through the use of capture tags, sorting tags and detectable labels in association with the probes, detector-ligators, and/or adaptor-indexers. Any combination of immobilization and association with capture tags, sorting tags, and labels can be used. Preferably, the probes are immobilized in arrays and the ligator-detectors are associated with a detectable label. Thus, detection of a signal at a particular location in a particular array of immobilized probes can provide information about nucleic acid fragments indexed from the nucleic acid sample.

Where the probes are immobilized in arrays, the array, and location in the array, where a DNA fragment generates a signal identify the sequence of the sticky end of the DNA fragment and of the sequence adjacent to the sticky end (or the recognition sequence of the first restriction enzyme and adjacent sequence when the recognition sequence and sticky end sequence overlap). This is a ten base sequence when a four base sticky end and six base immobilized oligonucleotides are used. The fixed relationship between the recognition sequence and the cleavage site of the type II-S restriction enzyme, when used, and the identity of the recognition sequence, provide additional sequence information about the DNA fragment. The same effect can be accomplished by otherwise capturing, sorting, or detecting particular probes (via capture tags, sorting tags, and labels). That is, so long as the probe and the ligator-detector coupled to it can be identified, a pattern can be determined.

Optionally, prior to hybridization with ligator-detectors, each sample (or index sample) can be incubated with one or more other nucleic acid cleaving reagents (referred to as second nucleic acid cleaving reagents), preferably a restriction enzyme having a four base recognition sequence. A second adaptor can then be coupled, preferably by ligation, to the DNA fragments in the samples. The DNA fragments can then be amplified using any suitable method, such as PCR.

One form of the FAAST method, referred to as modification assisted analysis of sequence tags (MAAST), assesses modification of sequences in nucleic acid molecules by basing cleavage of the molecules on the presence or absence of modification. For example, a site that is methylated in a nucleic acid molecule will not be cut by a restriction enzyme that is sensitive to methylation at that site. A restriction enzyme that is insensitive to methylation will cleave at that site, thus producing a different pattern of sequence tags.

Another form of the FAAST method, referred to as variable address analysis of sequence tags (VAAST) allows determination of associations, in a nucleic acid molecule, of different combinations of known or potential sequences. For example, particular combinations of joining and variable regions in immunoglobulins or T cell receptors can be determined. VAAST uses the same basic steps as FAAST and adds a step prior to cleavage of the nucleic acid sample. In VAAST, a recognition site for cleavage, preferably a restriction enzyme recognition site, is introduced into nucleic acid fragments in the nucleic acid sample. This recognition site is then used as the target of cleavage in the first basic FAAST method. The adaptor-indexers should be chosen to match known or potential sequences that would appear adjacent to the sequence into which the recognition site was introduced. The result is fragments with defined end sequences surrounding a central sequence derived from a nucleic acid fragment. This allows the association of known or potential sequences to be assessed. In particular, the association of the sequence into which the recognition site was introduced with a particular adaptor-indexer (which has sequence matching the known or potential adjacent sequence) can be detected.

Materials

Nucleic Acid Samples

Any nucleic acid sample can be used with the disclosed method. Examples of suitable nucleic acid samples include genomic samples, mRNA samples, cDNA samples, nucleic acid libraries (including cDNA and genomic libraries), whole cell samples, environmental samples, culture samples, tissue samples, bodily fluids, and biopsy samples. Numerous other sources of nucleic acid samples are known or can be developed and any can be used with the disclosed method. Preferred nucleic acid samples for use with the disclosed method are nucleic acid samples of significant complexity such as genomic samples and mRNA samples.

Nucleic acid fragments are segments of larger nucleic molecules. Nucleic acid fragments, as used in the disclosed method, generally refer to nucleic acid molecules that have been cleaved. A nucleic acid sample that has been incubated with a nucleic acid cleaving reagent is referred to as a digested sample. A nucleic acid sample that has been digested using a restriction enzyme is referred to as a digested sample.

An index sample is a nucleic acid sample that has been divided into different aliquots for further processing. In the context of the disclosed method, index samples are preferably aliquots of a digested nucleic acid sample to which different adaptor-indexers are added for coupling, preferably by ligation, to nucleic acid fragments present in the digested sample. In the disclosed method, different nucleic acid fragments are processed in the different index samples based on the sticky end sequence of the fragments. Thus, it is preferred that digested nucleic acid samples be divided into as many index samples as the number of possible sticky end sequences generated by the nucleic acid cleaving reagent used to digest the sample. Where multiple different nucleic acid cleaving reagents are used to cleave a nucleic acid sample, it is preferred that the nucleic acid sample be divided into as many aliquots as nucleic acid cleaving reagents used and that the nucleic acid sample be divided prior to cleavage.

A control nucleic acid sample is a nucleic acid sample to which another nucleic acid sample (which can be referred to as a tester nucleic acid sample) is to be compared. A control index sample is an index sample to which another index sample (which can be referred to as a tester index sample) is to be compared.

Secondary index samples are aliquots of index samples. Thus, index samples can be divided into a plurality of secondary index samples. Secondary index samples are to be cleaved with a nucleic acid cleaving reagent, preferably a restriction enzyme. Restricted index samples and non-restricted index samples are aliquots of index samples. Restricted index samples are to be cleaved with a nucleic acid cleaving reagent while non-restricted index samples are not. Restricted secondary index samples and non-restricted secondary index samples are aliquots of secondary index samples. Restricted secondary index samples are to be cleaved with a nucleic acid cleaving reagent while non-restricted secondary index samples are not. Secondary index samples, restricted index samples, non-restricted index samples, restricted secondary index samples, and non-restricted secondary index samples are referred to collectively herein as derivative index samples. Each is derived from an index sample and, in some cases, from another derivative index sample.

Nucleic Acid Cleaving Reagents

The disclosed method makes use of nucleic acid cleaving reagents. Nucleic acid cleaving reagents are compounds, complexes, and enzymes that cause, mediate, or catalyze cleavage on nucleic acid molecules. Preferred nucleic acid cleaving reagents are those that cleave nucleic acid molecules in a sequence-specific manner. Restriction enzymes (also referred to as restriction endonucleases) are the preferred form of nucleic acid cleaving reagents. Other nucleic acid cleaving reagents include the universal restriction endonucleases of Szybalski (Szybalski, Gene 40(2–3):169–73 (1985); Podhajska and Szybalski, Gene 40(2–3):175–82 (1985)[published erratum appears in Gene 43(3):325 (1985)]), and the advanced DNA cleavage systems have been evolved by Breaker et al. (Carmi et al., Proc Natl Acad Sci USA 95(5):2233–2237 (1998)).

Many nucleic acid cleaving reagents are known and can be used with the disclosed method. Relevant to the disclosed method, nucleic acid cleaving reagents generally have a recognition sequence and a cleavage site. Many nucleic acid cleaving reagents, especially restriction enzymes, also generate sticky ends at the cleavage site. A recognition sequence is the nucleotide sequence which, if present in a nucleic acid molecule, will direct cleavage of the nucleic acid molecule by a cognate nucleic acid cleaving reagent. The cleavage site of a nucleic acid cleaving reagent is the site, usually in relation to the recognition sequence, where the nucleic acid cleaving reagent cleaves a nucleic acid molecule. Sticky ends (also referred to as cohesive ends, protruding ends, and 5' or 3' overhangs) are single-stranded nucleic acid segments at the end of a double-stranded nucleic acid segment.

For specific embodiments of the method, the nucleic acid cleaving reagents used will have certain properties and/or certain relationships to other restriction enzymes used in the method. For example, in some preferred embodiments of the disclosed method, nucleic acid cleaving reagents that generates sticky ends having a plurality of different sequences are preferred, with nucleic acid cleaving reagents having a cleavage site offset from the recognition sequence being most preferred. Other embodiments of the disclosed method require the use of different nucleic acid cleaving reagents that have different recognition sequences and/or generate different sticky ends than other nucleic acid cleaving reagents used on the same index sample at other stages in the method. For example, where three digests (that is, cleavage reactions) are used in the method, it is preferred that the nucleic acid cleaving reagents used in each of the digests have a recognition sequence different from that of the nucleic acid cleaving reagents used in the other digests. In such cases, the known properties of nucleic acid cleaving reagents can be used to select or design appropriate nucleic acid cleaving reagents.

Where a nucleic acid cleaving reagent cleaves DNA at a site different or offset from the recognition sequence, a variety of sticky ends having different sequences can be generated. This is because recognition sequences in nucleic acids can occur next to any sequence and therefore the site of cleavage can have any sequence. For example, FokI cleaves 9 (upper strand) and 13 (lower strand) nucleotides downstream from the recognition site of GGATG. The four base sticky end will have whatever sequence happens to be 10 to 13 nucleotides away from the recognition site. Given enough cleavage sites, a total of 256 different sticky end sequences (that is every possible four base sequence) can result from a FokI digestion. As a result, restriction enzymes such as type II-S restriction enzymes can be said to generate sticky ends having a plurality of different sequences.

As used herein, unless otherwise indicated, the terms digest, digestion, digested, and digesting refer generally to a cleavage reaction or the act of cleaving and is not intended to be limited to cleavage by a protein enzyme or by any particular mechanism. Similarly, the term restricted is intended to refer to any nucleic acid cleavage, not just cleavage by a restriction enzyme. In the context of nucleic acid cleaving reagents, sequence-specific requires only some sequence specificity, not absolute sequence specificity. That is, nucleic acid cleaving reagents having a completely or partially defined recognition sequence are preferred. Thus, nucleic acid cleaving reagents having some degeneracy in their recognition sequence are still considered sequence-specific.

A second nucleic acid cleaving reagent is a nucleic acid cleaving reagent used to digest a secondary index sample. A third nucleic acid cleaving reagent is an nucleic acid cleaving reagent used to digest a restricted index sample or a restricted secondary index sample. Second and third nucleic acid cleaving reagents are preferably type II restriction endonucleases that cleave in the recognition sequence. A second restriction enzyme is a restriction enzyme used to digest a secondary index sample. A third restriction enzyme is an enzyme used to digest a restricted index sample or a restricted secondary index sample. Second and third restriction enzymes are preferably type II restriction endonucleases that cleave in the recognition sequence.

In addition to the use of restriction enzymes in a standard mode, one can make use of the type II-S enzymes as universal restriction endonuclease as described by Szybalski (Szybalski, Gene 40(2–3):169–73 (1985); Podhajska and Szybalski, Gene 40(2–3):175–82 (1985)[published erratum appears in Gene 43(3):325 (1985)]). In the Szybalski technique single stranded or double stranded DNA can be cleaved at any arbitrary (but specific) site utilizing the structure described in combination with a type II-S enzyme. More advanced DNA cleavage systems have been evolved by Breaker et al. (Carmi et al., Proc Natl Acad Sci USA 95(5):2233–2237 (1998)). In these systems Breaker has shown that DNA recognize a particular sequence in a target DNA and can cleave the target DNA, single stranded or double stranded targets. With Breaker's system for evolution of DNA for a particular action, it is clear that given reasonable time and effort a suitable DNA for a recognition and particular cleavage result is practical.

Adaptor-Indexers

Adaptor-indexers are double-stranded nucleic acids containing a single-stranded portion and a double-stranded portion. The single-stranded portion is at one end of the adaptor-indexer and constitutes a sticky end. The sticky end is referred to as the sticky end portion of the adaptor-indexer. It is preferable that the protruding single strand (sticky end) have two, three, four, or five nucleotides. The double-stranded portion of adaptor-indexers may have any convenient sequence or length. In general, the sequence and length of the double-stranded portion is selected to be adapted to subsequent steps in the method. For example, sequences in the adaptor-indexer may be used for primer or probe hybridization. A main purpose of adaptor-indexers is to provide sequence for hybridization by a ligator-detector. If the fragments in the samples to which adaptors have been coupled are to be amplified, the adaptor-indexers can also provide sequence for primer hybridization (which can overlap or be contiguous with sequence for ligator-detector hybridization). Thus, preferred sequence composition and length for the double-stranded portion of adaptor-indexers will generally be those that are useful for probe and primer hybridization. Adaptor-indexers can also include a detector portion which is designed to facilitate detection of the adaptor-indexer. The detection portion can be, for example, a sequence that is a hybridization target or it can be a label or tag.

Generally, the sequence of the double-stranded portion of an adaptor-indexer should not include the recognition sequence of any restriction enzyme to be used in a subsequent step in the method. It is preferred that adaptor-indexers not have any sequences that are self-complementary. It is considered that this condition is met if there are no complementary regions greater than six nucleotides long without a mismatch or gap.

A set of adaptor-indexers for use in the disclosed method should include different adaptor-indexers where the single-stranded portion each have a different nucleotide sequence selected from combinations and permutations of the nucleotides A, C, G, and T. Where multiple nucleic acid cleaving reagents are used in the first digest, the single-stranded portion of each adaptor-indexer can have a different nucleotide sequence compatible with a sticky end sequence generated by one of the nucleic acid cleaving reagents. While the sticky ends of adaptor-indexers in one set have different sequences, it is preferred that they be of the same length to facilitate use of the set to index fragments produced by cleavage by one nucleic acid cleaving reagent. It is preferable that the members of a set of adaptor-indexers contain a double-stranded portion which is identical for each member of the set.

A preferred set of indexing linker strands comprising: (a) at least two single-stranded first oligonucleotides each having a common identical sequence, and a unique sequence of a length selected from 2, 3, 4 and 5 nucleotides selected from permutations and combinations of A, G, C and T nucleotides, at one end selected from a 3' end and a 5' end; and (b) a single stranded second oligonucleotide whose sequence is complementary to the common sequence of the first oligonucleotides such that, when hybridized with any one of the first oligonucleotides, a double-stranded adaptor-indexer would result which includes an end having a sticky end with a unique sequence.

Adaptor-indexers can also contain or be associated with capture tags to facilitate immobilization or capture of fragments to which adaptor-indexers have been coupled. In general, the capture tag can be one member of a binding pair such as biotin and streptavidin. Capture tags are discussed more fully elsewhere herein. Adaptor-indexers can also contain or be associated with sorting tags to facilitate sorting or separation of fragments to which adaptor-indexers have been coupled. In general, the sorting tag can be a detectable label such as a fluorescent moiety or a manipulable moiety such as a magnetic bead. Sorting tags are discussed more fully elsewhere herein. Adaptor-indexers can also contain or be associated with labels to facilitate detection of fragments to which adaptor-indexers have been coupled. Adaptor-indexers can also be immobilized on a substrate.

Adaptor-indexers can also include a protruding end at the end opposite the sticky end. Such an end can be used as, for example, a hybridization target for a label to be associated with the adaptor-indexer (and thus can be considered the detection portion of the adaptor-indexer). Adaptor-indexers can also include one or more photocleavable nucleotides to facilitate release of adaptor-indexer sequences for detection. Photocleavable nucleotides and their use are described in WO 00/04036.

Adaptor-indexers need not be composed of naturally occurring nucleotides. Modified nucleotides, unnatural based and nucleotide and oligonucleotide analogs can be used. All that is required is that the adaptor-indexer have the general structure described herein and be capable of the interactions and reactions required in the disclosed method.

Ligator-Detectors

A ligator-detector is a nucleic acid molecule containing a single-stranded region that is complementary to a portion of a nucleic acid fragment generated in the disclosed method from a nucleic acid sample. The ligator-detectors generally have a specific sequence relationship to adaptor-indexers. Ligator-detectors include sequence—referred to as the detector portion of the ligator-detector—matching or complementary to all or part of sequence including, and adjacent to, the sticky end of at least one of the adaptor-indexers. Thus, the ligator-detector can have sequence matching or complementary to sequence in the nucleic acid fragment adjacent to the sticky end sequence (on either or both sides), matching or complementary to the sticky end, or sequence matching or complementary to both sequence in the nucleic acid fragment adjacent to the sticky end sequence and the sticky end.

Preferably, the sequence of a ligator-detector matches or is complementary to all or part of a sticky end sequence and all or part of the adjacent sequence of the adaptor-indexer designed for use with that sticky end sequence. In this form, the sequence of a ligator-detector matches or is complementary to all or part of the recognition sequence of the first restriction enzyme(s) when cleavage is not offset from the recognition sequence. For VAAST, it is preferred that the ligator-detector include sequence matching or complementary to sequence in the nucleic acid fragment adjacent to the sticky end sequence. Whether the sequence in the ligator-detector is matching or complementary determines which strand of the adaptor-indexer and/or fragment will hybridize to the detector-ligator. It is preferred that only one type of ligator-detector—matching or complementary—is used in a given FAAST reaction.

Some examples of sequence relationships between adaptor-indexers and ligator detectors are illustrated in FIG. 1. Ligator-detectors 1–12 in FIG. 1 are designed to match all or part of the sticky end sequence of adaptor-indexer I and all or part of the adjacent sequence of adaptor-indexer I. Ligator-detectors 13–19 are designed to be complementary to all or part of the sticky end sequence of adaptor-indexer I and all or part of the adjacent sequence of adaptor-indexer I. Ligator-detectors 21–32 are designed to match all or part of the sticky end sequence of adaptor-indexer II and all or part of the adjacent sequence of adaptor-indexer II. Ligator-detectors 33–40 are designed to be complementary to all or part of the sticky end sequence of adaptor-indexer II and all or part of the adjacent sequence of adaptor-indexer II. Note that the part of the adjacent sequence of the adaptor-indexer embodied in the ligator-detector is contiguous with the part of the sticky end sequence embodied in the ligator-detector. This is what is meant by adjacent.

Ligator-detectors 1–4 in FIG. 1 are designed to match all of the sticky end sequence of adaptor-indexer I and all or part of the adjacent sequence of adaptor-indexer I. Ligator-detectors 5–12 are designed to match part of the sticky end sequence of adaptor-indexer I and all or part of the adjacent sequence of adaptor-indexer I. Ligator-detectors 2–4 and 8–12 are designed to match all or part of the sticky end sequence of adaptor-indexer I and part of the adjacent sequence of adaptor-indexer I. Ligator-detectors 13–16 are designed to be complementary to all of the sticky end sequence of adaptor-indexer I and all or part of the adjacent sequence of adaptor-indexer I. Ligator-detectors 17–19 are designed to be complementary to part of the sticky end sequence of adaptor-indexer I and all or part of the adjacent sequence of adaptor-indexer I. Ligator-detectors 14–16 are designed to be complementary to all or part of the sticky end sequence of adaptor-indexer I and part of the adjacent sequence of adaptor-indexer I. Ligator-detector 20 is designed to match all of the recognition sequence of the restriction enzyme (which generates a sticky end compatible with the sticky end of adaptor-indexer I), and all of the adjacent sequence of adaptor-indexer I. Note the extra nucleotide extending beyond the adaptor-indexer sticky end sequence. This is a flanking nucleotide in the recognition sequence.

Ligator-detectors 21–24 are designed to match all of the sticky end sequence of adaptor-indexer II and all or part of the adjacent sequence of adaptor-indexer II. Ligator-detectors 25–32 are designed to match part of the sticky end sequence of adaptor-indexer II and all or part of the adjacent sequence of adaptor-indexer II. Ligator-detectors 22–24 and 28–31 are designed to match all or part of the sticky end sequence of adaptor-indexer II and part of the adjacent sequence of adaptor-indexer II. Ligator-detectors 33–36 are designed to be complementary to all of the sticky end sequence of adaptor-indexer II and all or part of the adjacent sequence of adaptor-indexer II. Ligator-detectors 37–40 are designed to be complementary to part of the sticky end sequence of adaptor-indexer II and all or part of the adjacent sequence of adaptor-indexer II. Ligator-detectors 34–36 and 40 are designed to be complementary to all or part of the sticky end sequence of adaptor-indexer II and part of the adjacent sequence of adaptor-indexer II.

Where the nucleic acid cleaving reagents used in the first digest cleave within the recognition sequence for the nucleic acid cleaving reagent such that the recognition sequence extends beyond the sticky end sequence, the ligator-detector can also match or be complementary to all or part of the recognition sequence. Where the recognition sequence extends beyond the sticky end sequence (for example, six-base recognition sequence and four-base sticky end), the ligator-detector sequence can extend beyond the sticky end sequence of its cognate adaptor-indexer. An example of such a ligator-detector is illustrated in FIG. 1 (ligator-detector number 20).

While the ligator-detector can be detected using sequence-based detection systems, the ligator-detectors can also contain a label to facilitate detection of the ligator-detector. Numerous labels are known and can be used for this purpose. Ligator-detectors can also contain or be associated with capture tags to facilitate immobilization or capture of the ligator-detectors. Ligator-detectors can also contain or be associated with sorting tags to facilitate sorting or separation of the ligator-detectors. Ligator-detectors can also be immobilized on a substrate.

Ligator-detectors can also include one or more photocleavable nucleotides to facilitate release of ligator-detector sequences for detection. Photocleavable nucleotides and their use are described in WO 00/04036.

Ligator-detectors need not be composed of naturally occurring nucleotides. Modified nucleotides, unnatural based and nucleotide and oligonucleotide analogs can be used. All that is required is that the ligator-detector have the general structure described herein and be capable of the interactions and reactions required in the disclosed method.

Detector Probes

Detector probes are molecules, preferably oligonucleotides, that can hybridize to nucleic acids in a sequence-specific manner. In the disclosed method, detector probes are used to capture ligator-detectors based on complementary sequences present in sample nucleic acid fragments to which the ligator-detectors are hybridized. Detector probes are preferably used in sets having a variety of probe sequences, preferably a set of probes having every possible combination (or hybridizable to every combination) of nucleotide sequence the length of the probe. Detector probes are preferably used in sets where each probe has the same length. Preferred lengths for the probe portion of detector probes are five, six, seven, and eight nucleotides. Detector probes preferably include a probe portion (for hybridization to sample fragments) and linker portions through which the probe portion is coupled to a substrate, capture tag, sorting tag, or label. These linker portions can have any suitable structure and will generally be chosen based on the method of immobilization or synthesis of the detector probes. The linker portion can be made up of or include nucleotides. The linker portions can have any suitable length and preferably are of sufficient length to allow the probe portion to hybridize effectively. For convenience and unless otherwise indicated, reference to the length of detector probes refers to the length of the probe portion of the probes. Immobilized detector probes are detector probes immobilized on a support.

Detector probes can be, and preferably are, immobilized on a substrate. Detector probes can also contain or be associated with capture tags to facilitate immobilization or capture of the probes and ligator-detectors to which they have been coupled. Detector probes can also contain or be associated with sorting tags to facilitate sorting or separation of the probes and ligator-detectors to which they have been coupled. Detector probes can also contain or be associated with labels to facilitate detection of the probes and ligator-detectors to which they have been coupled.

Detector probes can also include one or more photocleavable nucleotides to facilitate release of probe sequences and ligator-detectors coupled to the probe. Photocleavable nucleotides and their use are described in WO 00/04036.

Detector probes need not be composed of naturally occurring nucleotides. Modified nucleotides, unnatural based and nucleotide and oligonucleotide analogs can be used. All that is required is that the probe have the general structure described herein and be capable of the interactions and reactions required in the disclosed method.

Probe Arrays

Different detector probes can be used together as a set. The set can be used as a mixture of all or subsets of the probes, probes used separately in separate reactions, or immobilized in an array. Probes used separately or as mixtures can be physically separable through, for example, the use of capture tags, sorting tags, or immobilization on beads. A probe array (also referred to herein as an array) includes a plurality of probes immobilized at identified or predetermined locations on the array. In this context, plurality of probes refers to a multiple probes each having a different sequence. Each predetermined location on the array has one type of probe (that is, all the probes at that location have the same sequence). Each location will have multiple copies of the probe. The spatial separation of probes of different sequence in the array allows separate detection and identification of ligator-detectors that become coupled to the probes via hybridization of the probes to nucleic acid fragments in a nucleic acid sample. If a ligator-detector is detected at a given location in a probe array, it indicates that the sequence adjacent to the site in the nucleic acid fragment where the ligator-detector hybridized is complementary to the probe immobilized at that location in the array.

Adaptor-indexers and ligator-detectors can also be immobilized in arrays. Different modes of the disclosed method can be performed with different components immobilized, labeled, or tagged. Arrays of adaptor-indexers and ligator-detectors can be made and used as described below and elsewhere herein for the detector probes.

Solid-state substrates for use in probe array can include any solid material to which oligonucleotides can be coupled, directly or indirectly. This includes materials such as acrylamide, cellulose, nitrocellulose, glass, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin films or membranes, beads, bottles, dishes, fibers, woven fibers, shaped polymers, particles and microparticles. A preferred form for a solid-state substrate is a microtiter dish. The most preferred form of microtiter dish is the standard 96-well type.

Methods for immobilization of oligonucleotides to solid-state substrates are well established. Detector probes can be coupled to substrates using established coupling methods. For example, suitable attachment methods are described by Pease et al., *Proc. Natl. Acad. Sci. USA* 91(11):5022–5026 (1994), and Khrapko et al., *Mol Biol* (*Mosk*) (*USSR*) 25:718–730 (1991). A method for immobilization of 3'-amine oligonucleotides on casein-coated slides is described by Stimpson et al., *Proc. Natl. Acad. Sci. USA* 92:6379–6383 (1995). A preferred method of attaching oligonucleotides to solid-state substrates is described by Guo et al., *Nucleic Acids Res.* 22:5456–5465 (1994).

Methods for producing arrays of oligonucleotides on solid-state substrates are also known. Examples of such techniques are described in U.S. Pat. No. 5,871,928 to Fodor et al., U.S. Pat. No. 5,54,413, U.S. Pat. No. 5,429,807, and U.S. Pat. No. 5,599,695 to Pease et al.

Although preferred, it is not required that a given probe array be a single unit or structure. The set of probes may be distributed over any number of solid supports. For example, at one extreme, each probe may be immobilized in a separate reaction tube or container.

The probes in arrays can also be designed to have similar hybrid stability. This would make hybridization of fragments to detector probes more efficient and reduce the incidence of mismatch hybridization. The hybrid stability of probes can be calculated using known formulas and principles of thermodynamics (see, for example, Santa Lucia et al., *Biochemistry* 35:3555–3562 (1996); Freier et al., *Proc. Natl. Acad. Sci. USA* 83:9373–9377 (1986); Breslauer et al., *Proc. Natl. Acad. Sci. USA* 83:3746–3750 (1986)). The hybrid stability of the probes can be made more similar (a process that can be referred to as smoothing the hybrid stabilities) by, for example, chemically modifying the probes (Nguyen et al., *Nucleic Acids Res.* 25(15):3059–3065 (1997); Hohsisel, *Nucleic Acids Res.* 24(3):430–432 (1996)). Hybrid stability can also be smoothed by carrying out the hybridization under specialized conditions (Nguyen et al., *Nucleic Acids Res.* 27(6):1492–1498 (1999); Wood et al., *Proc. Natl. Acad. Sci. USA* 82(6):1585–1588 (1985)).

Another means of smoothing hybrid stability of the probes is to vary the length of the probes. This would allow adjustment of the hybrid stability of each probe so that all of the probes had similar hybrid stabilities (to the extent possible). Since the addition or deletion of a single nucleotide from a probe will change the hybrid stability of the probe by a fixed increment, it is understood that the hybrid stabilities of the probes in a probe array will not be equal. For this reason, similarity of hybrid stability as used herein refers to any increase in the similarity of the hybrid stabilities of the probes (or, put another way, any reduction in the differences in hybrid stabilities of the probes). This is useful since any such increased similarity in hybrid stability can improve the efficiency and fidelity of hybridization and ligation of the detector probes.

The efficiency of hybridization and ligation of detector probes to sample fragments can also be improved by grouping detector probes of similar hybrid stability in sections or segments of a probe array that can be subjected to different hybridization conditions. In this way, the hybridization conditions can be optimized for particular classes of probes.

Labels

To aid in detection and quantitation of ligator-detectors coupled to detector probes, labels can be incorporated into, coupled to, or associated with, ligator-detectors, detector probes, and/or adaptor-indexers. It is preferred that the ligator-detector be labeled. A label is any molecule that can be associated with ligator-detectors, directly or indirectly, and which results in a measurable, detectable signal, either directly or indirectly. A label is associated with a component when it is coupled or bound, either covalently or non-covalently, to the component. A label is coupled to a component when it is covalently coupled to the component. Many suitable labels for incorporation into, coupling to, or association with nucleic acid are known. Examples of labels suitable for use in the disclosed method are radioactive isotopes, fluorescent molecules, phosphorescent molecules, bioluminescent molecules, enzymes, antibodies, and ligands.

Examples of suitable fluorescent labels include fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7. Preferred fluorescent labels are fluorescein (5-carboxyfluorescein-N-hydroxysuccinimide ester) and rhodamine (5,6-tetramethyl rhodamine). Preferred fluorescent labels for simultaneous detection are FITC and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), CyS (652 nm: 672 nm), Cy5.5 (682 nm; 703 nm) and Cy7 (755 nm; 778 nm), thus allowing their simultaneous detection. The fluorescent labels can be obtained from a variety of commercial sources, including Molecular Probes, Eugene, Oreg. and Research Organics, Cleveland, Ohio.

Labeled nucleotides are preferred form of label since they can be directly incorporated into ligator-detectors during synthesis. Examples of labels that can be incorporated into DNA or RNA include nucleotide analogs such as BrdUrd (Hoy and Schimke, *Mutation Research* 290:217–230 (1993)), BrUTP (Wansick et al., *J. Cell Biology* 122:283–293 (1993)) and nucleotides modified with biotin (Langer et al., *Proc. Natl. Acad. Sci. USA* 78:6633 (1981)) or with suitable haptens such as digoxygenin (Kerkhof, *Anal. Biochem.* 205:359–364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.*, 22:3226–3232 (1994)). A preferred nucleotide analog detection label for DNA is BrdUrd (BUDR triphosphate, Sigma), and a preferred nucleotide analog detection label for RNA is Biotin-16-uridine-5'-triphosphate (Biotin-16-dUTP, Boehringher Mannheim). Fluorescein, Cy3, and Cy5 can be linked to dUTP for direct labeling. Cy3.5 and Cy7 are available as avidin or anti-digoxygenin conjugates for secondary detection of biotin- or digoxygenin-labeled probes.

Labels that are incorporated into nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5'-chloro)tricyclo [3.3.1.1$^{3,7}$]decane]-4-yl) phenyl phosphate; Tropix, Inc.).

Other labels include molecular or metal barcodes, mass labels, and labels detectable by nuclear magnetic resonance, electron paramagnetic resonance, surface enhanced raman scattering, surface plasmon resonance, fluorescence, phosphorescence, chemiluminescence, resonance raman, microwave, or a combination. Mass labels are compounds or moieties that have, or which give the labeled component, a distinctive mass signature in mass spectroscopy. Mass labels are useful when mass spectroscopy is used for detection. Preferred mass labels are peptide nucleic acids and carbohydrates. Combinations of labels can also be useful. For example, color-encoded microbeads having, for example, 265 unique combinations of labels, are useful for distinguishing numerous components. For example, 256 different ligator-detectors can be uniquely labeled and detected allowing mutiplexing and automation of the disclosed method.

Useful labels are described in de Haas, R. R., et al., "Platinum porphyrins as phosphorescent label for time-resolved microscopy," *J. Histochem. Cytochem.* 45(9) :1279–92 (1997); Karger and Gesteland, "Digital chemiluminescence imaging of DNA sequencing blots using a charge-coupled device camera," *Nucleic Acids Res.* 20(24) :6657–65 (1992); Keyes, R. S., et al., "Overall and internal dynamics of DNA as monitored by five-atom-tethered spin labels," *Biophys. J.* 72(1):282–90 (1997); Kirschstein, S., et al., "Detection of the DeltaF508 mutation in the CFTR gene by means of time- resolved fluorescence methods," *Bioelectrochem. Bioenerg.* 48(2):415–21 (1999); Kricka, L. J., "Selected strategies for improving sensitivity and reliability of immunoassays," *Clin. Chem.* 40(3):347–57 (1994); Kricka, L. J., "Chemiluminescent and bioluminescent techniques," *Clin. Chem.* 37(9):1472–81 (1991); Kumke, M. U., et al., "Temperature and quenching studies of fluorescence polarization detection of DNA hybridization," *Anal. Chem.* 69(3):500–6 (1997); McCreery, T., "Digoxigenin labeling," *Mol. Biotechnol.* 7(2):121–4 (1997); Mansfield, E. S., et al., "Nucleic acid detection using non-radioactive labeling methods," *Mol. Cell Probes* 9(3): 145–56 (1995); Nurmi, J., et al., "A new label technology for the detection of specific polymerase chain reaction products in a closed tube," *Nucleic Acids Res.* 28(8):28 (2000); Oetting, W. S., et al. "Multiplexed short tandem repeat polymorphisms of the Weber 8A set of markers using tailed primers and infrared fluorescence detection," *Electrophoresis* 19(18):3079–83 (1998); Roda, A., et al., "Chemiluminescent imaging of enzyme-labeled probes using an optical microscope-videocamera luminograph," *Anal. Biochem.* 257(1):53–62 (1998); Siddiqi, A., et al., "Evaluation of electrochemiluminescence- and bioluminescence-based assays for quantitating specific DNA," *J. Clin. Lab. Anal.* 10(6):423–31 (1996); Stevenson, C. L., et al., "Synchronous luminescence: a new detection technique for multiple fluorescent probes used for DNA sequencing," *Biotechniques* 16(6):1104–11 (1994); Vo-Dinh, T., et al., "Surface-enhanced Raman gene probes," *Anal. Chem.* 66(20) :3379–83 (1994); Volkers, H. H., et al., "Microwave label detection technique for DNA in situ hybridization," *Eur. J. Morphol.* 29(1):59–62 (1991).

Metal barcodes, a form of molecular barcode, are 30–300 nm diameter by 400–4000 nm multilayer multi metal rods. These rods are constructed by electrodeposition into an alumina mold, then the alumina is removed leaving these small multilayer objects behind. The system can have up to 12 zones encoded, in up to 7 different metals, where the metals have different reflectivity and thus appear lighter or darker in an optical microscope depending on the metal; this leads to practically unlimited identification codes. The metal bars can be coated with glass or other material, and probes attached to the glass using methods commonly known in the art; assay readout is by fluorescence from the target, and the identity of the probe is from the light dark pattern of the barcode.

Methods for detecting and measuring signals generated by labels are known. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody. Such methods can be used directly in the disclosed method of amplification and detection. As used herein, detection molecules are molecules which interact with amplified nucleic acid and to which one or more detection labels are coupled. In another form of detection, labels can be distinguished temporally via different fluorescent, phosphorescent, or chemiluminescent emission lifetimes. Multiplexed time-dependent detection is described in Squire et al., J. Microscopy 197(2):136–149 (2000), and WO 00/08443.

Quantitative measurement of the amount or intensity of a label can be used. For example, quantitation can be used to determine if a given label, and thus the labeled component, is present at a threshold level or amount. A threshold level or amount is any desired level or amount of signal and can be chosen to suit the needs of the particular form of the method being performed.

Second Adaptors

Second adaptors are double-stranded nucleic acids containing a single-stranded portion and a double-stranded portion. The single-stranded portion is at one end of the second adaptor and constitutes a sticky end. It is preferable that the protruding single strand (sticky end) have two, three, four, or five nucleotides. The double-stranded portion of second adaptor may have any convenient sequence or length. In general, the sequence and length of the double-stranded portion is selected to be adapted to subsequent steps in the method. For example, sequences in the second adaptor may be used for primer or probe hybridization. If the fragments in the samples to which adaptors have been ligated are to be amplified, the second adaptors can provide sequence for primer hybridization. Thus, preferred sequence composition and length for the double-stranded portion of second adaptors will generally be those that are useful for primer hybridization.

Generally, the sequence of the double-stranded portion of a second adaptor should not include the recognition sequence of any nucleic acid cleaving reagent to be used in a subsequent step in the method. It is preferred that second adaptors not have any sequences that are self-complementary. It is considered that this condition is met if there are no complementary regions greater than six nucleotides long without a mismatch or gap.

A set of second adaptors for use in the disclosed method can include different second adaptors where the single-stranded portion each have a different nucleotide sequence compatible with a sticky end sequence generated by one of the second restriction enzymes. It is preferable that the members of a set of second adaptors contain a double-stranded portion which is identical for each member of the set.

Second adaptors can also contain or be associated with capture tags to facilitate immobilization or capture of fragments to which second adaptors have been coupled. Second adaptors can also contain or be associated with sorting tags to facilitate sorting or separation of fragments to which second adaptors have been coupled. Second adaptors can also contain or be associated with labels to facilitate detection of fragments to which second adaptors have been coupled. Second adaptors can also be immobilized on a substrate.

Capture Tags

A capture tag is any compound that can be used to separate compounds or complexes having the capture tag from those that do not. Preferably, a capture tag is a compound, such as a ligand or hapten, that binds to or interacts with another compound, such as ligand-binding molecule or an antibody. It is also preferred that such interaction between the capture tag and the capturing component be a specific interaction, such as between a hapten and an antibody or a ligand and a ligand-binding molecule.

Preferred capture tags, described in the context of nucleic acid probes, are described by Syvnen et al., *Nucleic Acids Res.*, 14:5037 (1986). Preferred capture tags include biotin, which can be incorporated into nucleic acids. In the disclosed method, capture tags incorporated into adaptor-indexers or second adaptors can allow sample fragments (to which the adaptors have been coupled) to be captured by, adhered to, or coupled to a substrate. Such capture allows simplified washing and handling of the fragments, and allows automation of all or part of the method.

Capturing sample fragments on a substrate may be accomplished in several ways. In one embodiment, capture docks are adhered or coupled to the substrate. Capture docks are compounds or moieties that mediate adherence of a sample fragment by binding to, or interacting with, a capture tag on the fragment. Capture docks immobilized on a substrate allow capture of the fragment on the substrate. Such capture provides a convenient means of washing away reaction components that might interfere with subsequent steps.

Substrates for use in the disclosed method can include any solid material to which components of the assay can be adhered or coupled. Examples of substrates include, but are not limited to, materials such as acrylamide, cellulose, nitrocellulose, glass, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Substrates can have any useful form including thin films or membranes, beads, bottles, dishes, fibers, woven fibers, shaped polymers, particles and microparticles. Preferred forms of substrates are plates and beads. The most preferred form of beads are magnetic beads.

In one embodiment, the capture dock is an oligonucleotide. Methods for immobilizing and coupling oligonucleotides to substrates are well established. For example, suitable attachment methods are described by Pease et al., *Proc. Natl. Acad. Sci. USA* 91(11):5022–5026 (1994), and Khrapko et al., *Mol Biol (Mosk) (USSR)* 25:718–730 (1991). A method for immobilization of 3'-amine oligonucleotides on casein-coated slides is described by Stimpson et al., *Proc. Natl. Acad. Sci. USA* 92:6379–6383 (1995). A preferred method of attaching oligonucleotides to solid-state substrates is described by Guo et al., *Nucleic Acids Res.* 22:5456–5465 (1994).

In another embodiment, the capture dock is the anti-hybrid antibody. Methods for immobilizing antibodies to substrates are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidin-biotin, photocrosslinkable agents, epoxides and maleimides. A preferred attachment agent is glutaraldehyde. These and other attachment agents, as well as methods for their use in attachment, are described in *Protein immobilization: fundamentals and applications*, Richard F. Taylor, ed. (M. Dekker, New York, 1991), Johnstone and Thorpe, *Immunochemistry In Practice* (Blackwell Scientific Publications, Oxford, England, 1987) pages 209–216 and 241–242, and *Immobilized Affinity Ligands*, Craig T. Hermanson et al., eds. (Academic Press, New York, 1992). Antibodies can be attached to a substrate by chemically cross-linking a free amino group on the antibody to reactive side groups present within the substrate. For example, antibodies may be chemically cross-linked to a substrate that contains free amino or carboxyl groups using glutaraldehyde or carbodiimides as cross-linker agents. In this method, aqueous solutions containing free antibodies are incubated with the solid-state substrate in the presence of glutaraldehyde or carbodiimide. For crosslinking with glutaraldehyde the reactants can be incubated with 2% glutaraldehyde by volume in a buffered solution such as 0.1 M sodium cacodylate at pH 7.4. Other standard immobilization chemistries are known by those of skill in the art.

Sorting Tags

A sorting tag is any compound that can be used to sort or separate compounds or complexes having the sorting tag from those that do not. In general, all capture tags can be a sorting tag. Sorting tags also include compounds and moieties that can be detected and which can mediate the sorting of tagged components. Such forms of sorting tags are generally not also capture tags. For example, a fluorescent moiety can allow sorting of components tagged with the moiety from those that are not (or those with a different tag). However, such a fluorescent moiety does not necessarily have a suitable capture dock with which it can interact and be captured. Preferably, a sorting tag is a label, such as a fluorescent label, that can mediate sorting.

Amplification Target Circle

An amplification target circle (ATC) is a circular single-stranded DNA molecule, generally containing between 40 to 1000 nucleotides, preferably between about 50 to 150 nucleotides, and most preferably between about 50 to 100 nucleotides. Portions of ATCs have specific functions making the ATC useful for rolling circle amplification (RCA). These portions are referred to as the primer complement portion and the reporter tag portions. The primer complement portion and the reporter tag portion are required elements of an amplification target circle. Those segments of the ATC that do not correspond to a specific portion of the ATC can be arbitrarily chosen sequences. It is preferred that ATCs do not have any sequences that are self-complementary. It is considered that this condition is met if there are no complementary regions greater than six nucleotides long without a mismatch or gap.

An amplification target circle, when replicated, gives rise to a long DNA molecule containing multiple repeats of sequences complementary to the amplification target circle. This long DNA molecule is referred to herein as tandem sequences DNA (TS-DNA). TS-DNA contains sequences complementary to the primer complement portion and the reporter tag portions. These sequences in the TS-DNA are referred to as primer sequences (which match the sequence of the rolling circle replication primer) and reporter tags. Amplification target circles and their use are further described in U.S. Pat. No. 5,854,033.

Method

The FAAST method involves the following basic steps. A nucleic acid sample, embodied in double stranded DNA, is incubated with one or more nucleic acid cleaving reagent, preferably restriction endonucleases, such that a set of DNA fragments having sticky ends with a variety of sequences is generated. Preferred for this purpose is the use of a single type II-S restriction endonuclease having an offset cleavage site. Since such class II-S restriction endonucleases cleave at a site different from the recognition sequence, this results in a set of DNA fragments having sticky ends with a variety of sequences. A similar effect can be obtained by digesting the nucleic acid sample with a mixture of restriction endonucleases or other nucleic acid cleaving reagents which cleave at their recognition site.

For a four base sticky end, there are 256 possible sequences. The general formula is $N=4^X$ where X is the length of the sticky end and N is the number of possible sequences. In a sufficiently complex nucleic acid sample, all of these sequences will be represented in the ends of the set of DNA fragments. The nucleic acid sample is also divided into aliquots (referred to as index samples); preferably as many aliquots as there are sticky end sequences (that is, $N=4^X$ aliquots). Where multiple restriction endonucleases are used, the nucleic acid sample is preferably divided into index samples before digestion. Where a single restriction endonuclease is used, the nucleic acid sample is preferably divided into index samples following digestion. Each index sample is then mixed with a different adaptor-indexer, each of which has a sticky end compatible with one of the possible sticky ends on the DNA fragments in that index sample. The adaptor-indexes are then coupled onto compatible DNA fragments. The basic method then proceeds to hybridization of the nucleic acid sample with ligator-detectors.

Optionally, prior to hybridization with ligator-detectors, each index sample can then be incubated with one or more other nucleic acid cleaving reagents (referred to as second nucleic acid cleaving reagents), preferably restriction enzymes. Second nucleic acid cleaving reagents are preferably restriction enzymes having a four base recognition sequences. All index samples are preferably digested with the same nucleic acid cleaving reagent(s). Alternatively, the index samples can be further divided into secondary index samples each of which is digested with a different second nucleic acid cleaving reagent or set of nucleic acid cleaving reagents. A second adaptor can then be coupled to the DNA fragments in the index samples (or secondary index samples). Preferably, the same second adaptor is used for each index sample. Different second adaptors are preferably used with secondary index sample derived from the same index sample. In this case, it is preferred that the same set of second adaptors be used with each set of secondary index samples. DNA fragments in each index sample (or secondary index sample) now have adaptors ligated to each end. The DNA fragments can then be amplified using any suitable method, such as PCR. Sequences in the adaptors can be used as primer binding sites for this amplification.

Optionally, prior to hybridization with ligator-detectors, the index samples (or secondary index samples) can divided into further aliquots. These are referred to as restricted index samples and non-restricted index samples (or restricted secondary index samples and non-restricted secondary index samples, if there are secondary index samples). Generally, the index samples (or secondary index samples) can be divided into one or more restricted index samples and one non-restricted index sample. The restricted index samples (or restricted secondary index samples), but not the non-restricted index sample (or non-restricted secondary index sample) are then each incubated with a different nucleic acid cleaving reagents (referred to as third nucleic acid cleaving reagents), preferably restriction enzymes. The third nucleic acid cleaving reagents are preferably different from any of the nucleic acid cleaving reagents or second nucleic acid cleaving reagents with which the sample has been digested.

In some cases, the third nucleic acid cleaving reagents will cleave some DNA fragments in the restricted index samples (or restricted secondary index samples), thus making the fragment incompetent for amplification (another optional step prior to hybridization of the nucleic acid sample with ligator-detectors). In this way, the signals generated by the restricted index samples and non-restricted index sample (or restricted and non-restricted secondary index samples) can differ, and fragments containing the recognition sequence of one of the third restriction enzymes can be identified.

Secondary index samples, restricted index samples, non-restricted index samples, restricted secondary index samples, and non-restricted secondary index samples are referred to collectively herein as derivative index samples. Each is derived from an index sample and, in some cases, from another derivative index sample. In general, only those derivative index samples last generated are carried forward in the method. For example, if secondary index samples are created, the original index samples from which they were derived are no longer carried forward in the method (the secondary index samples are). Similarly, if restricted and non-restricted secondary index samples are created, then neither the original index samples nor the secondary index samples from which the restricted and non-restricted secondary index samples were derived are carried forward in the method. However, additional information may be gained by carrying forward all or some of the index samples and derivative index samples.

After the basic steps (and any desired optional steps), the DNA fragments in each index sample (or each derivative index sample, if used) are hybridized to ligator-detectors. One portion of each ligator-detector matches or is complementary to all or part of sequence including, and adjacent to, the sticky end of at least one of the adaptor-indexers. Preferably, the ligator-detector has sequence matching or complementary to one of the possible sticky end sequences generated by digestion with the restriction enzymes. The ligator-detector can also be complementary to nucleotides in the recognition sequence of the restriction enzymes if restriction enzymes that cleave in their recognition sequence are used. Ligator-detectors can also have sequence matching or complementary to common sequences in the adaptor-indexers. In this case, the appropriate ligator-detector is used with each of the index samples (or each derivative index sample, if used). That is, the ligator-detector oligonucleotide used in each index sample (or each derivative index sample) matches or is complementary to sequence, including sticky end sequence (and recognition sequence, if overlapping with the sticky end sequence), in the adaptor-indexer sequence used in that index sample (or used in the index sample from which the derivative index sample was derived). Alternatively, the ligator-detector can have sequence matching or complementary to sequence of the nucleic acid fragment (to which an adaptor-indexer has been coupled) adjacent to the sticky end sequence and on opposite the side of the fragment from the adaptor-indexer. Such ligator-detectors are preferred for use in VAAST.

Finally, each index sample (or each derivative index sample) is mixed with detector probes and the probes are coupled to the ligator-detectors. Preferably, the set of probes used include every possible sequence of a given length (for example, every possible six base sequence). The detector probes can be immobilized in an array.

The ends of the detector probes and the ligator-detectors are coupled together only if the probe hybridizes adjacent to the end of the ligator-adaptor. Thus, a ligator-detector is coupled to a detector probe only when a sequence complementary to the probe is present immediately adjacent to the region in a DNA fragment from the original sample to which the end of the ligator-detector hybridizes (preferably the sticky end sequences). Examples of the relationship and interaction of various components of the disclosed method are illustrated in FIGS. 2, 3, 4, and 5.

Each processed DNA fragment (that is, each DNA fragment to which an adaptor-indexer was ligated) from the sample will result in an association of a ligator-detector (and an adaptor-indexer) with a detector probe. This association will be detected through a signal generated from one of the associated components. In a preferred form of the disclosed method, the set of detector probes (if multiple sets are used) in which the signal for a given fragment is determined by the sequence of the original sticky end sequence (or recognition sequence). Each different sticky end or recognition sequence is processed in a separate index sample; a separate set of detector probes is used for each index sample or derivative index sample. The probe in the set of probes to which the signal for a given fragment is associated and detected is determined by the sequence in the DNA fragment adjacent to the sticky end sequence (or recognition sequence) since the detector probe must hybridize to this sequence in order to be coupled to the ligator-detector hybridized to the DNA fragment. A complex nucleic acid sample will produce a unique pattern of signals in the probe sets. It is this pattern that allows unique cataloging of nucleic acid samples and sensitive and powerful comparisons of the patterns of signals produced from different nucleic acid samples.

The set of detector probes, and particular probe in the set, in which a signal is associated identifies the sequence of the sticky end of the DNA fragment that gave rise to the signal and of the sequence adjacent to the sticky end (or the recognition sequence of the restriction enzyme and of the sequence adjacent to the recognition sequence). This is a ten base sequence when a four base sticky end and six base probes are used. The set of detector probes identifies the sticky end sequence (the four bases) because each set of detector probes used a different adaptor-indexer having a different sticky end sequence. The particular probe identifies the sequence adjacent to the sticky end (the six bases) because each probe has a different probe with a different sequence. Only the probe with sequence complementary to the adjacent sequence will hybridize and thus become associated with a signal. The fixed relationship between the recognition sequence and the cleavage site of a type 11-S restriction enzyme, when used, and the identity of the recognition sequence, provide additional sequence information about the DNA fragment.

The information generated is similar when probe arrays are used. The array (if multiple arrays are used) in which the signal for a given fragment is detected is determined by the sequence of the original sticky end sequence (or recognition sequence). Each different sticky end or recognition sequence is processed in a separate index sample; a separate array is used for each index sample or derivative index sample. The location in the array in which the signal for a given fragment is detected is determined by the sequence in the DNA fragment adjacent to the sticky end sequence (or recognition sequence) since the probe must hybridize to this sequence in order to be coupled to the ligator-detector hybridized to the DNA fragment. A complex nucleic acid sample will produce a unique pattern of signals on the arrays.

The array, and location in the array, where a DNA fragment generates a signal identifies the sequence of the sticky end of the DNA fragment and of the sequence adjacent to the sticky end (or the recognition sequence of the restriction enzyme and of the sequence adjacent to the recognition sequence). This is a ten base sequence when a four base sticky end and six base probes are used. The array identifies the sticky end sequence (the four bases) because each array used a different adaptor-indexer having a different sticky end sequence. The location in the array identifies the sequence adjacent to the sticky end (the six bases) because each location in the array has a different probe with a different sequence. Only the probe with sequence complementary to the adjacent sequence will hybridize and thus become associated with a signal. The fixed relationship between the recognition sequence and the cleavage site of a type II-S restriction enzyme, when used, and the identity of the recognition sequence, provide additional sequence information about the DNA fragment.

The disclosed method is performed using one or more nucleic acid cleaving reagents that collectively produce a plurality of different sticky end sequences. Preferably, the sticky end sequences generated by the nucleic acid cleaving reagent are not limited by the recognition sequence of the nucleic acid cleaving reagent. The sticky ends generated are preferably 2, 3, 4 or 5 nucleotides long. Preferred nucleic acid cleaving reagents for use in the disclosed method are type II-S restriction endonucleases, which are enzymes that cleave DNA at locations outside of (or offset from) the recognition site and which generate sticky ends. Examples of Type II-S restriction endonucleases are FokI, BbvI, HgaI, BspMI and SfaNI.

Nucleic acid cleaving reagents for use in the disclosed method produce sticky ends encompassing permutations and combinations of the four nucleotides, A, C, G, and T. The larger the number of protruding bases, the greater the number of possible permutations and combinations of terminal nucleotide sequences, and the more specific the indexing is likely to be. For example, a restriction endonuclease such as FokI, which releases fragments with four base, 5'-protruding sticky ends, will generate fragments having $4^4$ or 256 possible protruding tetranucleotide ends. Cleavage of a cDNA sample having an average of 12,000 different cDNAs with the restriction endonuclease FokI will produce a mixture of fragments with four base, 5'-protruding ends. For a sample containing a random distribution of bases, on average, FokI cuts twice in every $4^5$ base pairs giving an average fragment size of 512 base pairs. If the average length of cDNA is 1,700 base pairs, each cDNA will produce approximately four fragments. The entire sample will contain approximately 4*12,000=48,000 fragments. There are $4^4$=256 possible tetranucleotide sequences and therefore 256 possible identities for each sticky end. On average, there will be 48,000/256=188 fragments with a given sticky end sequence. Each of these fragments is sorted by hybridization to different probes based on the sequence adjacent to the sticky end sequence in each fragment. A hexamer probe array has 4,096 different six nucleotide probes. Thus, only 188 of the 4,096 hexamers in the probe array will ligate to a ligator-detector, on average. With 256 probe arrays each having 4,096 different hexamer detector probes, there are 256* 4,096=1,048,576 "bins" in which to distribute 48,000 fragments. This leaves ample opportunity to identify different patterns when using different cDNA samples.

Cleavage of human genomic DNA (which has a haploid number of $3 \times 10^9$ base pairs) with the restriction endonuclease Bsp24I will release a large and complex mixture of fragments with five base, 3'-protruding ends. On average, Bsp24I cuts twice in every $4^6$ base pairs giving an average fragment size of 2048 base pairs, and resulting in $3 \times 10^9$/2048=approximately $1.5 \times 10^6$ fragments. There are $4^5$=1024 possible pentanucleotide sequences and therefore 1024 possible identities for each sticky end. On average, there will be $1.5 \times 10^6$/1024=1,465 fragments with a given sticky end sequence. Each of these fragments is sorted by hybridization to different probes based on the sequence adjacent to the sticky end sequence in each fragment. An heptamer probe array has 16,384 different seven nucleotide probes. Thus, only 1,465 of the 16,384 heptamers in the array will ligate to a ligator-detector, on average. With 1024 detector arrays each having 16,384 different heptamer probes, there are 1024*16,384=$1.6 \times 10^7$ "bins" in which to distribute $1.5 \times 10^6$ fragments.

Cleavage of a cDNA sample with twenty different restriction endonucleases having six-base recognition sequences will produce a mixture of fragments with sticky ends. On average, restriction endonucleases having six-base recognition sequences cut once every $4^6$=4096 base pairs. If the sample contains approximately 12,000 cDNA molecules with an average length of cDNA of 1,500 base pairs, cleavage with one of the restriction enzymes will result about 3200 cuts (and thus 6400 DNA fragments with sticky ends). Further cleavage of the sample (second digest) with two different restriction endonucleases having four-base recognition sequences will result in additional cuts once every $4^4$=256 base pairs. Since the second digest will, in many cases, result in cuts on each fragment, this will result in (for each of the 20*2=40 secondary index samples) approximately 6,400 fragments, each approximately 256 base pairs long.

If five different restriction endonucleases having four-base recognition sequences are used for the third digest, approximately half of the fragments in each restricted secondary index sample will be cleaved (since these restriction enzymes will cut about once every 256 base pairs). Thus, there will be approximately 3,200 fragments (intact, with both an adaptor-indexer and a second adaptor) in each of the 20*2*5=200 restricted secondary index samples (there will be approximately 6,400 fragments in the non-restricted secondary index sample). Each of these fragments is sorted by hybridization to different probes based on the sequence adjacent to the sticky end sequence in each fragment. A hexamer probe array has 4,096 different six nucleotide probes. Thus, only 3,200 of the 4,096 hexamers in the array will ligate to a ligator-detector, on average. With 200 probe arrays each having 4,096 different hexamer probes, there are 200*4,096=819,200 "bins" in which to distribute the of 3,200*200=640,000 total fragments (a heptamer array would provide 200*16,384=3,276,800 "bins").

As these examples illustrate, the length of the recognition sequence, the length of the sticky end generated, and the length of the probes used together determine the number of data bins into which the nucleic acid fragments are sorted. By using sticky ends and detector probes of sufficient length, the sorting of fragments can be matched to the complexity of the sample being analyzed.

The use of a comprehensive panel of adaptor-indexers provides a means for attaching specific functional modifications to selected subsets of a complex mixture of nucleic acid fragments and identifying the molecules so modified. Such a defined subset of molecules may be further resolved by additional cleavage and indexing, or by any of the established techniques such as cloning, PCR amplification, or gel electrophoresis. Individual members of the class may be distinguished by identifying characteristics such as length, sequence, or restriction endonuclease maps. The sequence of the sticky ends of the adaptor-indexers provides a means of indexing a large number of nucleic acid fragments.

Detector probes of different sequence can be immobilized at different locations on a probe array. In this way, the sequence of the probes on the probe array and the sequence of nucleic acid fragments in the index samples determine where on the array ligator-detectors become coupled. The presence, amount, presence and amount, or absence of ligator-detector at different locations in the probe arrays thus forms a pattern of signals that provides a signature or fingerprint of a nucleic acid sample based on the presence or absence of specific nucleic acid sequences in the sample. For this reason, cataloging of this pattern of signals (that is, the pattern of the presence, amount, presence and amount, or absence of ligator-detectors) is an embodiment of the disclosed method that is of particular interest. As discussed elsewhere herein, the probability of probe mismatch can be used to create more complex catalogs based on differential hybridization of particular fragments to different detector probes.

Catalogs can be made up of, or be referred to, as, for example, a pattern of ligator-detectors on probe arrays, a pattern of the presence of ligator-detectors on probe arrays, a catalog of nucleic acid fragments in a sample, or a catalog of nucleic acid sequences in a sample. The information in the catalog is preferably in the form of positional information (that is, location in the detector array) or, more preferably, in the form of sequences. Preferred sequence information for catalogs include sequences of detector probes to which a ligator-detector was coupled and sequences of nucleic acid fragments present in the sample (derived from the locations in the detector array where ligator-detectors were coupled).

Such catalogs of nucleic acid samples can be compared to a similar catalog derived from any other sample to detect similarities and differences in the samples (which is indicative of similarities and differences in the nucleic acids in the samples). For example, a catalog of a first nucleic acid sample can be compared to a catalog of a sample from the same type of organism as the first nucleic acid sample, a sample from the same type of tissue as the first nucleic acid sample, a sample from the same organism as the first nucleic acid sample, a sample obtained from the same source but at a different time than the first nucleic acid sample, a sample from a different organism than the first nucleic acid sample, a sample from a different type of tissue than the first nucleic acid sample, a sample from a different strain of organism than the first nucleic acid sample, a sample from a different species of organism than the first nucleic acid sample, or a sample from a different type of organism than the first nucleic acid sample.

The same type of tissue is tissue of the same type such as liver tissue, muscle tissue, or skin (which may be from the same or a different organism or type of organism). The same organism refers to the same individual, animal, or cell. For example, two samples taken from a patient are from the same organism. The same source is similar but broader, referring to samples from, for example, the same organism, the same tissue from the same organism, or the same cDNA library. Samples from the same source that are to be compared are preferably collected at different times (thus allowing for potential changes over time to be detected). This is especially useful when the effect of a treatment or change in condition is to be assessed. A different organism refers a different individual organism, such as a different patient, a different individual animal. Different organism includes a different organism of the same type or organisms of different types. A different type of organism refers to organisms of different types such as a dog and cat, a human and a mouse, or E. coli and Salmonella. A different type of tissue refers to tissues of different types such as liver and kidney, or skin and brain. A different strain or species of organism refers to oganisms differing in their species or strain designation as those terms are understood in the art.

The presence, amount, presence and amount, or absence of ligator-detectors coupled to detector probes can be accomplished by detection of labels incorporated into, coupled to, or associated with the ligator-detectors. Alternatively, the ligator-detectors can be detected based on detection of their sequence. These detections are generally referred to as direct detection of coupling of ligator-detectors. Any of the numerous sequence-specific detection techniques can be used for this purpose, including, for example, hybridization of labeled probes. The presence, amount, presence and amount, or absence of ligator detectors can also be detected by generating a signal mediated by the ligator-detector. Use of the ligator-detector as a primer for rolling circle replication, described below, is a preferred example of this. The presence, amount, presence and amount, or absence of ligator detectors can also be detected by detecting the detector probe to which the ligator-detector is coupled, the adaptor-indexer associated with the coupled ligator-detector, or both. These detections are generally referred to as indirect detection of coupling of ligator-detectors.

The signal to be detected for the nucleic acid fragments can be increased by nucleic acid amplification during the method. It is preferred either that the nucleic acid fragments to which adaptor-indexers have been coupled (referred to as adaptor/fragments) be amplified or that the ligator-detectors that have been coupled to detector probes be amplified or mediate amplification of another nucleic acid. In the first case, the adaptor/fragments can be amplified using any suitable method. These include polymerase chain reaction (PCR), ligase chain reaction (LCR), self-sustained sequence replication (3SR), nucleic acid sequence based amplification (NASBA), strand displacement amplification (SDA), amplification with Qβ replicase, and rolling circle amplification (RCA) (Birkenmeyer and Mushahwar, *J. Virological Methods*, 35:117–126 (1991); Landegren, *Trends Genetics*, 9:199–202 (1993); Lizardi et al., *Nature Genetics* 19(3):225–232 (1998)). In the case of ligator-detector amplification, a preferred form of amplification is rolling circle amplification of a single-stranded circular DNA molecule primed by the ligator-detector. In this way, a long tandem repeat of the DNA circle is generated with the amplified strand anchored to the detector array via the ligator-detector. This technique of amplification is described in PCT application WO 97/19193. If the ligator-detector is used as a rolling circle replication primer, there is no need to incorporate a label in the ligator-detector since the amplified DNA can be detected (either directly or via an incorporated label).

Amplification of the adaptor/fragments is facilitated by the presence of adaptor-indexer sequence at the end of the fragment (and by the presence of second adaptor sequence at the other end, if a second adaptor is used). For example, the adaptor sequences can be used for amplification primer sequences. The adaptor sequences can also be used to circularize the adaptor/fragments for subsequent amplification by rolling circle replication. Rolling circle amplification is described in U.S. Pat. No. 5,854,033 and PCT application WO 97/19193.

In another embodiment, the strands of nucleic acid fragments to which adaptor-indexers have been coupled (adaptor/fragments) can be separated prior to hybridization to the ligator-detectors. Such strand separation can improve the efficiency of ligator-detector hybridization. This separation can be accomplished using any suitable technique. Strand separation is preferably accomplished by including a capture tag or sorting tag on one of the strands of the adaptor-indexers. Such a capture tag can then be used to immobilize one strand of the adaptor/fragments while the other strands are washed away. Either the immobilized or washed strand can be carried forward in the method. A sorting tag can allow separation of the strands by a sorting technique.

In another embodiment, the concentration of the various nucleic acid fragments in the index samples are normalized. Normalization can be preformed either before after any amplification step that may be used. A preferred technique for fragment normalization involves immobilizing one strand of the nucleic acid fragments, denaturing the nucleic acid fragments, renaturing the nucleic acid fragments for a time greater than the $c_0t_{1/2}$ for abundant nucleic acid fragments and less than the $c_0t_{1/2}$ for rare nucleic acid fragments, and collecting the un-renatured nucleic acid fragments.

To correct hybridization errors one may use one of two general approaches in a singular, dual or sequential manner. For purpose of illustration consider a hybridization and ligation experiment carried out in a glass microarray detection system. In the first approach one treats a hybridized array, prior to the ligation step, with a process that blocks ligation of the indexer-detector to an incorrect probe sequence. The key to this approach is to block (sterically hinder) the nick to be ligated such that the covalent bonding mechanism is unable to make the bond. In practice one would take a hybridized array and contact it with the blocking entity and a suitable buffer and hold the system at a suitable temperature for an appropriate time for the masking entity to become correctly located on the mismatches, then continuing with ligation. A number of single chain antibodies selected to bind to particular mismatches are of use for this method, as are a number of yeast mismatch repair and cell cycle checkpoint proteins such as MSH2-MSH6 (Habraken et al., ATP-dependent assembly of a ternary complex consisting of a DNA mismatch and the yeast MSH2-MSH6 and MLH1-PMS1 protein complexes. J Biol Chem 273(16):9837–41 (1998)); MSH2-MSH3 (Habraken et al., Binding of insertion/deletion DNA mismatches by the heterodimer ofyeast mismatch repair proteins MSH2 and MSH3. Curr Biol 6(9):1185–7 (1996)); MutS; and Mec1 (Paciotti et al., Mec1p is essential for phosphorylation of the yeast DNA damage checkpoint protein Ddc1p, which physically interacts with Mec3p. Embo J 17(14):4199–209 (1998)).

The second approach is to treat a covalently bonded probe-target sample with a system that recognizes and specifically cleaves the strand containing the mismatch. This second approach utilizes recognition of mismatches and destructive targeting or 'error checking' of the mismatched region such that in the final stringent washes of the probe array the destroyed mismatched sample is washed away from the chip before the signal detection procedure. In practice one would take the hybridized and ligated probe array and contact it with the error checking reagents in a suitable buffer and hold the system at a suitable temperature for an appropriate time for the error checking reagent to locate the mismatches and destroy the strand containing the mismatch prior to the final stringent washes. One or more of the following 'error checking' systems can be used: T4 endonuclease VII; proteins MutH, MutL, and MutS together; MutY (Lu and Hsu, Detection ofsingle DNA base mutations with mismatch repair enzymes. Genomics 14(2):249–55 (1992)); glycosylase (Neddermann and Jiricny, Efficient removal of uracilfrom G. U mispairs by the mismatch-specific thymine DNA glycosylase from HeLa cells. Proc Natl Acad Sci USA 91(5):1642–6 (1994)); mammalian topoisomerase I (Yeh et al., Mammalian topoisomerase I has base mismatch nicking activity. J Biol Chem 269(22):15498–504 (1994)); and T7 endonuclease I.

In particular, the fidelity of the hybridization/coupling steps in the disclosed method—the steps where adaptor-indexers are coupled to fragments and where ligator-detectors are coupled to detector probes—can be increased by digesting the samples with a mismatch nuclease such as T4 endonuclease VII. T4 endonuclease VII cleaves double-stranded DNA where there is a mismatch. By "unligating" illegitimate hybridization/ligations, the mis-cataloging of nucleic acid fragments will be made less likely. Fidelity of hybridization/ligation steps can also be maximized by using appropriately stringent hybridization conditions.

The following provides examples of FAAST and the sequence and sequence relationships that can be obtained. When a single type II-S restriction enzyme is used in the first digest, the sequence information obtainable can be illustrated with the following structures:

DNA fragment: . . . NNNNXXXX . . . NNNNRRRR-ROOOOOOOOOSSSSNNNN . . .

Sequence information: RRRRROOOIIIIISSSS.

In these structures, each character represents a nucleotide. N represents any nucleotide (having no special identity or relationship to the method). R represents a nucleotide in the recognition sequence of the type II-S restriction enzyme. O represents a nucleotide in the offset between the recognition site and the cleavage site of the type II-S restriction enzyme. S represents a nucleotide in the sticky end resulting from cleavage with the type 11-S restriction enzyme. X represents a nucleotide in the recognition/cleavage site of the second restriction enzyme. I represents a nucleotide complementary to the immobilized oligonucleotide.

From the DNA fragment . . . NNNNXXXX . . . NNNNR-RRRROOOOOO OOOSSSSNNNN . . . , the sequence information RRRRROOOIIIIISSSS can be obtained. In this example, the type II-S restriction enzyme has a five base recognition sequence, a nine base offset to the cleavage site (that is, there are nine bases between the recognition sequence and the cleavage site), and creates a four base sticky end. The probes contain hexamer sequences. Each array location where a signal is generated in this example thus represents a specific sequence: nnnnn - - - nnnnnnnnnnn (where n represents an identified nucleotide and each— represents an unidentified nucleotide). This is referred to as a determined sequence. The portion of the nucleic acid fragments for which the sequence is determined corresponds to the sticky end sequence, the sequence adjacent to the sticky end sequence to which the detector probe hybridized, and the recognition sequence of the restriction enzyme (S, I, and R, respectively).

This sequence information can also be represented by the structure

A-B-C-D where A is the recognition sequence of the restriction enzyme, B is the gap of unknown sequence, C is the sequence to which the immobilized oligonucleotide hybridized, and D is the sticky end sequence. The gap represents the nucleotides between the recognition sequence and the sequence to which the probe hybridized. C is always adjacent to the sticky end sequence D. In the example above, A is RRRRR, B is OOO, C is IIIIII, and D is SSSS. Cleavage by the second restriction enzyme also adds useful information since without cleavage there would be no amplification (and thus no further processing of that nucleic acid molecule) with the result that a signal will be absent.

The sequence information that can be obtained with the disclosed method can be further illustrated using a specific example of a nucleic acid fragment. Assume a nucleic acid sample containing a nucleic acid fragment with the sequence ... CGGTGGATGACTTGAAGCTATGCTTAGG ... (SEQ ID NO:1)
... GCCACCTACTGAACTTCGATACGAATCC ...

If the sample is digested with FokI—a type II-S restriction enzyme with a recognition sequence of GGATG and a cleavage site offset by 9 and 13 nucleotides—the fragment will be cleaved to generate the following fragments (the FokI recognition sequence is shown in bold)

... CGGTGGATGACTTGAAGCTATGCTTAGG ... (bases 1–18 and 19–28 of SEQ ID NO:1)
... GCCACCTACTGAACTTCGATAC GAATCC ...

When the corresponding adaptor-indexer is ligated to fragment and the ligated fragment is hybridized to the corresponding ligator-detector, the following nucleic acid is obtained (sequence from the adaptor-indexer is underlined)

TATGCGGTATTACAGCCTATTGGG-label (bases 7–30 of SEQ ID NO:2)
... GCCACCTACTGAACTTCGATAC GCCATAATGTCGGATAACCC.

When this nucleic acid is hybridized to an appropriate probe (an immobilized hexamer in this example) and the probe and ligator-detector are ligated the following structure is obtained support
TGAAGCTATGCGGTATTACAGCCTATTGGG-label (SEQ ID NO:2)
... GCCACCTACTGAACTTCGATAC GCCATAATGTCGGATAACCC.

The sequence of the immobilized probe is identified by the location in a probe array where the label of the ligator-detector is detected. The sequence of the adjacent sticky end is identified by the detector array in which the label of the ligator-detector is detected (since a different detector array is used for each sticky end sequence). Finally, the sequence of the recognition sequence is identified by the relationship of the cleavage site to the recognition sequence. Thus, in this example, detection of label in the TGAAGC hexamer position of the ATAC sticky end detector array indicates the presence of a nucleic acid fragment in the nucleic acid sample having the sequence

CCTACNNNACTTCGATAC. (SEQ ID NO:3)

Relating this sequence to the generalized structure A-B-C-D, A is CCTAC, B is NNN, C is ACTTCG, and D is ATAC.

When multiple restriction enzymes are used for the first digestion, the sequence information obtainable can be illustrated with the following structures:

DNA fragment: ... NNXXXXNN ... NNRRRRNN ... NNIIIIIISSSSSSSNN ...
Sequence: XXXX .... RRRR ... IIIIIISSSSSS.

In these structures, each character represents a nucleotide. N represents any nucleotide (having no special identity or relationship to the method). S represents a nucleotide in the recognition sequence (including sticky end) of the first restriction enzyme. X represents a nucleotide in the recognition/cleavage site of the second restriction enzyme. R represents a nucleotide in the recognition sequence of the third restriction enzyme. I represents a nucleotide complementary to the detector probe. The sequence and distance between the recognition sites of the second and third restriction enzymes and between the recognition site of the second restriction enzyme and the probe complement are not determined in the basic method.

From the DNA fragment ... NNXXXX ... NNRRRRNN ... NNIIIIII SSSSSSNN ..., the sequence information XXXX ... RRRR ... IIIIIISSSSSS can be obtained. In this example, the immobilized probes contain hexamer sequences. Each array location where a signal is generated in this example thus represents a specific sequence: nnnn ... nnnn ... nnnnnnnnnnnn (where n represents an identified nucleotide and each ... represents an unidentified gap sequence). This is referred to as a determined sequence. The portion of the nucleic acid fragments for which the sequence is determined corresponds to the recognition sequence of the first restriction enzyme, the sequence adjacent to the recognition sequence to which the detector probe hybridized, the recognition sequence of the second restriction enzyme, and the recognition sequence of the third restriction enzyme (S, I, X, and R, respectively).

This sequence information can also be represented by the structure

E-B-F-B-C-D where B is a gap of unknown sequence, C is the sequence to which the probe hybridized, D is the recognition sequence of the first restriction enzyme, E is the recognition sequence of the second restriction enzyme, and F is the recognition sequence of the third restriction enzyme. The gaps represent nucleotides between the recognition sequences of the second and third restriction enzymes and between the recognition sequence of the third restriction enzyme and the sequence to which the probe hybridized. C is always adjacent to the recognition sequence D. In the example above, C is IIIIII, D is SSSSSS, E is XXXX, and F is RRRR.

The sequence information that can be obtained with the disclosed method can be further illustrated using a specific example of a nucleic acid fragment. Assume a nucleic acid sample containing a nucleic acid fragment with the sequence ... CGCATGGG ... ATAGCTTG ... CAAGCTATG-GATCCGA ... (SEQ ID NO:4–6)
... GCGTACCC ... TATCGAAC ... GTTCGATAC-CTAGGCT ...

If the sample is first digested with BamHI—a restriction enzyme with a recognition sequence of GGATCC generating a four-base sticky end—the fragment will be cleaved to generate the following fragments:

... CGCATGGG ... ATAGCTTG ... CAAGCTATG-GATCCGA ... (SEQ ID NOS:4 & 5 and bases 1–9 and 10–15 of SEQ ID NO:6)
... GCGTACCC ... TATCGAAC ... GTTCGATAC-CTAGGCT ...

When the corresponding adaptor-indexer is ligated to the fragment and the fragment digested with NlaI (recognition sequence CATG) the result is bases 1–6 and 7–8 of SEQ ID NO:7, SEQ ID NO:5, and SEQ ID NO:7:

... CGCATGGG. .. ATAGCTTG ... CAAGCTATG-GATCTGGTATTACAGCCTATTG
... GCGTACCC ... TATCGAAC ... GTTCGATAC-CTAGACCATAATGTCGGATAAC

After addition of the second adaptor and hybridization to the corresponding ligator-detector, the following nucleic acid is obtained (sequence from the adaptor-indexer is underlined). Note that the adaptor-indexer hybridizes to both the sticky end sequence and the remaining recognition sequence (that is, the C not in the sticky end).

GGATCTGGTATTACAGCCTATT-*(bases 9–30 of SEQ ID NO:7)
CGGTACCTAGAGAGTGTACCC.TATCGAAC . . . GTTCGATACCTAG<u>ACCATAATGTCGGATAA</u> (SEQ ID NO:8, complementary strands of SEQ ID NOS:5 & 7)

When this nucleic acid is hybridized to an appropriate probe (an immobilized hexamer in this example) and the immobilized probe and ligator-detector are ligated the following structure is obtained support
AGCTATGGATCCGGTATTACAGCCTATT-* (bases 3–30 of SEQ ID NO:7)
CGGTACCTAGAGAGTGTACCC . . . TATCGAAC . . . GTTCGATACCTAG <u>GCCATAATGTCGGATAA</u> (SEQ ID NO:8 and complementary strands of SEQ ID NO:5 & 7).

The sequence of the immobilized probe is identified by the location in the array where the label of the ligator-detector is detected. The sequence of the adjacent recognition sequence (including the sticky end) is identified by the array in which the label of the ligator-detector is detected (since a different set of arrays is used for each index sample). The sequence of the recognition sequence of the second restriction enzyme is identified by the array in which the label of the ligator-detector is detected (since a different set of arrays is used for each secondary index sample). Finally, the presence of an internal sequence (the recognition sequence of the third restriction enzyme) is determined by seeing if the signal is absent from the array for the restricted secondary index sample that was digested with the third restriction enzyme (a different array is used for each restricted and non-restricted secondary index sample). If the signal is absent, it indicates the recognition site is present in the fragment. This digestion would be performed prior to the NlaI digestion or following the NlaI digestion if there was an amplification step after digestion with the third restriction enzyme.

Thus, in this example, detection of label in the AGCTAT (SEQ ID NO:9) hexamer position of the TCGA (SEQ ID NO:10) third recognition site array in the GTAC (SEQ ID NO:11) second recognition site set of arrays in the CCTAGG (bases 7–12 of SEQ ID NO:12) sticky end set of arrays indicates the presence of a nucleic acid fragment in the nucleic acid sample having the sequence GTAC . . . TCGA . . . TCGATACCTAGG. (SEQ ID NO:12) Relating this sequence to the generalized structure E-B-F-B-C-D, C is TCGATA (bases 1–6 of SEQ ID NO:12), D is CCTAGG (bases 7–12 of SEQ ID NO:12), E is GTAC (SEQ ID NO:11), and F is TCGA (SEQ ID NO:10).

Use of labels and sorting in FAAST can be illustrated with the following example which makes use of microbeads in a new way. In this example, 256 ligator-detectors are coupled to the surface of 256 of color encoded microbeads. Each ligator-detector is identified by a single color. After annealing and ligating these new "microbead ligator-detectors" to the target sequences, the 256 sets of "microbead ligator-detectors" are loaded simultaneously in a 4096-well microtiter plate containing 4096 hexamer probes, one probe per well. Only a perfect match during hybridization will ligate a fluorochrome-labeled hexamer to a specific microbead labeled complex. Since the Luminex flow analyzer can distinguish color encoded microbeads and measure their fluorescence simultaneously, one can identify the six bases adjacent to the ligator-detector by knowing the specific address (and the hexamer contained at that address) of the wells on the microtiter plate. The design is illustrated below.

The steps up to generating the single-stranded amplicon are the same as in one basic FAAST, including II-S enzyme cuts, adaptor indexer ligation, second 4 bp enzyme cut, second adaptor ligation, PCR amplification, and capturing and denaturing the fragments to generate single-stranded fragments.

The 256 single stranded DNA amplicons are annealed to 256 ligator-detectors. There are 256 different sequences of ligator-detector oligonucleotides, which comprise the 256 different ligator-detectors complementary to each of the 4-base sticky ends generated. The ligator-detector is labeled with a signaling moiety, such as a fluorescent dye or a fluorescent bead. Each of the 256 annealed single stranded preparations is split into 4096 aliquots and hybridized to one of 4096 hexamer probes. For example, the 4096 hexamers are contained in a 4096 microtiter plate, with each well containing a single hexamer probe. Each of the 4096 hexamer probes is fluorescently labelled at the 5'-end and contains a free 3'-hydroxyl end.

Following hybridization and ligation of the hexamer probe with the annealed single-stranded amplicons, the 256 preparations are transferred to another well containing streptavidin and unbound material is washed away (the hexamer probe also contains a biotin group). Two signals are then measured.

One signal corresponds to the sample (either tester or control, for instance). Tester and control samples are distinguished by fluorescently encoded beads (Luminex). In one embodiment, one would use 512 colors, 256 colors for the tester and 256 colors for the control. However, one could also use 256 color encoded beads where the beads are "offset" between the tester and control. For instance, color 1 corresponds to hexamer 2 for the tester but hexamer 3 for the control, and so on. The second signal derives from the labeled hexamer probe and measures the level of the single-stranded DNA annealed to the ligator-detector. The two signals measured here could be read simultaneously on an instrument such as the Luminex 100.

A number of varied probe sets and arrays are known in the art and can be used with FAAST. Terstappen et al. (Tibbe, A. G., et al., Optical tracking and detection of immunomagnetically selected and aligned cells. Nat Biotechnol, 1999. 17(12): p. 1210–3; Dolan, G. J. and L. W. M. M. Terstappen, Magnetic separation apparatus and methods employing an internal magnetic capture gradient and an external transport force, . 1999: U.S. Pat. No. 5,985,153; Terstappen, L. W. M. M. and P. A. Liberti, Quantitative cell analysis methods employing magnetic separation,. 1999: U.S. Pat. No. 5,993, 665; Terstappen, L. W. M. M. and P. A. Liberti, Methods for biological substance analysis employing internal magnetic gradients separation and an externally-applied transport force,. 2000: U.S. Pat. No. 6,013,188) have demonstrated immunomagnetically selected and fluorescently labeled probes for detection of cells of interest. In their technique the cells are labeled using immunospecific binding probes and the resulting labeled cells are induced to move into detector range by an externally applied magnetic field. Lithographic processing of one wall of the sample vessel leads to the improvement of locating the tagged cells along well determined spatial patterns.

Thorp et al. (Napier, M. E., et al., Probing biomolecule recognition with electron transfer: electrochemical sensors for DNA hybridization. Bioconjug Chem, 1997. 8(6): p. 906–13; Thorp, H. H., C. R. Loomis, and M. E. Napier, Polymer-electrodes for detecting nucleic acid hybridization and method of use thereof,. 1999: U.S. Pat. No. 5,968,745; Thorp, H. H., et al., Electrochemical detection of nucleic acid hybridization,. 1999: U.S. Pat. No. 5,871,918; Welch, T. W., Electochemicalprobesfor detection of molecular interactions and drug discovery,. 1999: WO9964847) have developed an electrochemical detection method. Their method directly detects target nucleic acids without sample amplification or use of fluorescent labels. Detection is accomplished by following the oxidation-reduction cycle of $Ru(bpy)_3^{2+}$ by electrochemical measurement. The measurement elements have synthetically prepared oligonucleotide probes attached to electrodes, the electrodes have been fabricated into a variety of formats including biochips, microtiter plates and hand-held devices.

Spectral labeling coupled with a counting technique, such as flow cytometry, has been exploited for analysis of DNA samples (Fulton, R. J., Method and compositions forflow cytometric determination ofDNA sequences,. 1998: U.S. Pat. No. 5,736,330; Phipps, S., et al., Precisionfluorescently dyed particles and methods of making and using same,. 1999: WO9919515; Chandler, D. and M. B. Chandler, Microparticles with multiple fluorescent signals, . 1999: WO9937814). In such analyses, micron scale beads are color coded according to the probes attached to their surface, targets are labeled with an analytical fluorescent tag, and the coincidence events containing the bead color and the analytical color are counted. In this manner a probe array of many colors can be read out very quickly and easily.

In another technique utilizing microspheres, Walt et al. (Walt, D. R., Techview: molecular biology. Bead-basedfiber-optic arrays. Science, 2000. 287(5452): p. 451–2; Ferguson, J. F., B. G. Healey, and D. R. Walt, Fiber optic biosensor for selectively detecting oligonucleotide species in a mixed fluid sample,. 1988: WO9850782; Walt, D. R. and K. L. Michael, Fiber optic sensor with encoded microspheres,. 2000: U.S. Pat. No. 6,023,540; Michael, K. L., et al., Randomly ordered addressable high-density optical sensor arrays. Anal Chem, 1998. 70(7): p. 1242–8) have developed a system where the probes are attached to the microspheres and the microspheres subsequently self assemble in a random spatial pattern into the distal end of a fiber optic array. The "optical bar code" signature each microsphere provides the identity of the attached probe, and signal of the labeled target indicates the concentration of the target.

Modification Assisted Analysis of Sequence Tags (MAAST)

Modification assisted analysis of sequence tags (MAAST) is a form of FAAST that assesses modification of sequences in nucleic acid molecules by detecting differential cleavage based on the presence or absence of modification in the molecules. For example, a site that is methylated in a nucleic acid molecule will not be cut by a restriction enzyme that is sensitive to methylation at that site. A restriction enzyme that is insensitive to methylation will cleave at that site, thus producing a different pattern of sequence tags. Comparison of the results with different samples of nucleic acids can establish differences in the modification levels or patterns on the different samples. As used herein, a nucleic acid cleaving reagent or restriction enzyme that is sensitive to modification in its recognition site is a nucleic acid cleaving reagent or restriction enzyme that will either cleave only when the site is unmodified or will cleave only when the site is modified (that is, the nucleic acid cleaving reagent or restriction enzyme requires a particular modification state for cleavage). A nucleic acid cleaving reagent or restriction enzyme that is insensitive to modification in its recognition site is a nucleic acid cleaving reagent or restriction enzyme that will cleave regardless of whether the site is modified or unmodified.

MAAST is useful for assessing the state, level, and condition of modifications in nucleic acid molecules. Many nucleic acid modifications are known and most can have biological effects and significance. Methylation, for example, is a universal mechanism for regulating gene expression in animals and plants (Bird and Wolffe, Methylation-induced repression-belts, braces, and chromatin, Cell 99:451–454 (1999); Finnegan et al., DNA Methylation in Plants, Annual Rev Physiol 49:223–247 (1998); Bird, DNA Methylation de Novo, Science 286:2287–2288 (1999)). Understanding the physiological consequences of methylation has utility in a number of fields. It is well documented that methylation of promoter regions can repress transcription, both in vitro and in vivo (Baylin et al., Alterations in DNA methylation: a fundamental aspect of neoplasia, Adv Cancer Res 72:141–96 (1998)). For instance, the promoters of several genes implicated in neoplasia and tumor suppression are subject to hypermethylation (Melki et al., Concurrent DNA hypermethylation of multiple genes in acute myeloid leukemia, Cancer Res 59(15):3730–40 (1999)). Methylation also performs important functions in plant development and flowering.

The use of differential methylation to study gene function traditionally required prior knowledge of DNA sequences subject to methylation, obtained only after substantial effort to clone, sequence and verify the methylation sensitivity of the region of interest. MAAST expedites the identification of differentially methylated sequences by, in its preferred forms, combining the power of high throughput microarray technology and in silico analysis with the sensitivity and quantitation of differential display.

MAAST has several advantages over other methods currently used to identify promoters on a genomic scale. Current approaches to identify promoter and other regulatory elements in a high throughput manner include: in silico analysis of nucleotide sequence for transcription factor binding sites, β-lactamase insertion (Whitney et al., A genome-wide functional assay of signal transduction in living mammalian cells, Nat Biotechnol 16(13):1329–33 (1998)), COBRA (Xiong and Laird, COBRA: a sensitive and quantitative DNA methylation assay, Nuc Acid Res 25(12):2532–2534 (1997)), and restriction landmark genomic scanning (Costell et al., aberrant CpG-island methylation has non-random and tumour-type-specific patterns, Nature Genetics 25:132–138 (2000)).

Other forms of modification are indicative of certain types of DNA damage caused by particular agencies. These include alkylation, dimerization, derivatization, depurination, or ADP-ribosylation. Examples of modifications and their source are described in Lodovici et al., Levels of 8-hydroxydeoxyguanosine as a marker of DNA damage in human leukocytes, Free Radic Biol Med 28(1):13–7 (2000); Maehira et al., Alterations of protein kinase C, 8-hydroxydeoxyguanosine, and K-ras oncogene in rat lungs exposed to passive smoking, Clin Chim Acta 289(1–2):133–44 (1999); Gamboa Da Costa et al., Characterization of the Major DNA Adduct Formed by alpha-Hydroxy-N-desmethyltamoxifen in Vitro and in Vivo, Chem Res Toxicol 13(3):200–207 (2000); Phillips et al., Methods of DNA adduct determination and their application to testing compounds for genotoxicity, Environ Mol Mutagen 35(3):222–233 (2000); Airoldi et al., Carcinogen-DNA adducts as tools in risk assessment, Adv Exp Med Biol 472:231–40 (1999); Purewal et al., Association between acetylator genotype and 2-amino-1-methyl-6-phenylimidazo[4,5-b]pyridine (PhIP) DNA adduct formation in colon and prostate of inbred Fischer 344 and Wistar Kyoto rats, Cancer Lett 149(1–2):53–60 (2000).

MAAST uses the same basic steps as FAAST and includes cleavage with a second nucleic acid cleaving reagent and coupling of a second adaptor to the nucleic acid fragments. The difference is that MAAST uses a nucleic acid cleaving reagent that is sensitive to modification of its recognition site. Thus, the nucleic acid cleaving reagent will either not cleave at a site that is modified or cleave only at a site that is modified. In nucleic acid fragments that have a modification at the recognition site, the fragment will not be cleaved by the second nucleic acid cleavage reagent and no second adaptor will be added to the end.

Uncleaved nucleic acid fragments can be culled from the procedure in a number of ways. For example, if the nucleic acid fragments are to be amplified following addition of the second adaptors, amplification can be made dependent on the presence of a second adaptor on the end. This can be accomplished, for example by using a PCR primer complementary to sequence in the second adaptor. The uncleaved nucleic acid fragments can also be culled by, for example, including a capture tag, sorting tag, or label in the second adaptor. By capturing or sorting the fragments based on the presence or absence of the capture or sorting tag, one can carry forward in the procedure only those fragments containing a second adaptor.

If a label is associated with the second adaptor, all of the fragments can be carried forward in the procedure but only those having a second adaptor (and thus a label) will produce a detectable signal (in this scenario, the label on the second adaptor would have to be detected in association with a detector probe and/or a ligator-detector). Use of a label in this manner in the second adaptor can also allow discrimination of cleaved and uncleaved fragments (that is, fragments cleaved or not cleaved by the second nucleic acid cleaving reagent). This can be accomplished by detecting coupling of ligator-detectors to detector probes via labels, capture tags, or sorting tags on the detector probes, ligator-detectors, or adaptor-indexers and also detecting the presence, amount, presence and amount, or absence of a second adaptor on the fragment via its label.

MAAST can also be used to determine how one type of cell or organism influences gene expression or other biological pathways in another type of cell or organism. For example, suppose that a mouse is genetically altered via gene targeting to inactivate a particular methyltransferase gene (there are several known for mouse but for the illustration purposes, assume there is only one). Cells of interest (for instance, B cells) are taken from the mouse and mixed with other cells of interest (for instance, T cells) obtained from a normal mouse. The B and T cells are mixed together. One could then compare the T cell methylation pattern between B cell mixed and non-B cell mixed. It would be safe to conclude that the observed changes in methylation occurred within the T cells since the B cells harbored an inactivated methyltransferase.

Using standard differential gene expression techniques, it would be very difficult for many genes, and impossible for others, to distinguish which transcripts originated in the B cells and which transcripts originated in the T cells (since any two cell types will share expression of a number of genes). However, due to the prior genetic alterations, that is, deleting the methyltransferase gene, MAAST allows examination of gene expression in a mixed cell population.

MAAST can be further understood through the following illustration.

1. Isolate genomic DNA (gDNA) from control and tester samples.

2. Select a set of two restriction enzymes. Each set contains a type II-S restriction enzyme and a type II restriction enzyme that will not cut DNA when methylated. In this illustration FokI (II-S) and HinPII (II, methylation sensitive) are used as examples. There a number of type II-S and type II restriction enzymes that could be used.

3. First digest gDNA with the type II-S restriction endonuclease. A 5' four base overhang is preferred:

```
5'-NNNNNNNNNNGGATGNNNNNNNNNNNNNNNN-3' (SEQ ID NO:13)
   ||||||||||||||||||||||||||||||
3'-NNNNNNNNNNCCTACNNNNNNNNNNNNNNNN-5'
```

Cut with FokI to produce:

```
                         (bases 1–29 of SEQ ID NO:13)
5'-NNNNNNNNNNGGATGNNNNNNNNN-3'
   |||||||||||||||||||||||
3'-NNNNNNNNNNCCTACNNNNNNNNN-5'
```

4. Distribute to 256 wells, each with one of 256 unique adapter-indexers.

5. Ligate an adapter-ligator (one of 256) complimentary to the four base overhang. The adapter-indexer contains a biotin moiety to facilitate subsequent purification away from non-ligated strands.

```
                         (bases 1–28 of SEQ ID NO:13)
5'-NNNNNNNNNNGGATGNNNNNNNNNNnnnn-adap-ind-3'
   ||||||||||||||||||||||||||||
3'-NNNNNNNNNNCCTACNNNNNNNNNNNNNN-adap-ind-5'-Biotin
```

6. Wash ligation products to eliminate non-ligated material. Leaving only ligated products.

```
                         (bases 1–28 of SEQ ID NO:13)
  5'-NNNNNNNNNNGGATGNNNNNNNNNNnnn-adap-ind-3'
     ||||||||||||||||||||||||||||||
  3'-NNNNNNNNNNCCTACNNNNNNNNNNNNNN-adap-ind-5'-Biotin
```

7. Second digest with a methylation sensitive restriction endonuclease (or pair/combination of restriction enzymes that recognize the same site and where one of the enzymes will not cut a methylated site and the other one will).
  Example: Control sample digested with HinPII:

```
5'-NNNGCGCNNNNNNNNNN//NNNNNNNNNGGATGnnnn..adap-ind-3'     (SEQ ID NO:14 and bases 2-19
   ||||||||||||||||  |||||||||                             of SEQ ID NO:13)
3'-NNNCGCGNNNNNNNNNN//NNNNNNNNNCCTACNNNN..adap-ind-5'-Biotin
```

Cut with HinPII to produce:

```
5'-NNNG    CGCNNNNNNNNNN//NNNNNNNNNGGATGnnnn..adap-ind-3'   (bases 1-4 and 5-16 of SEQ ID NO:
   ||||       ||||||||||//|||||||||                         and bases 2-19 of SEQ ID NO:13)
3'-NNNCGC     GNNNNNNNNN//NNNNNNNNNCCTACNNNN..adap-ind-5'-
Biotin
```

Example: Tester sample (which has undergone methylation at the HinPII site) digested with HinPII (SEQ ID NO:15 and bases 2–19 of SEQ ID NO:13):

```
        CH3
         |
5'-NNNGCGCNNNNNNNNNN//NNNNNNNNNGGATGnnnn..adap-ind-3'
   ||||||||||||||||
3'-NNNCGCGNNNNNNNNNN//NNNNNNNNNCCTACNNNN..adap-ind-5'-Biotin
```

Cut with HinPII (methylation sensitive) to produce:

```
        CH3   (No cut)
         |
5'-NNNGCGCNNNNNNNNNN//NNNNNNNNNGGATGnnnn..adap-ind-3'(SEQ ID NO:15 and bases 2-19 of SEQ ID NO:13)
   ||||||||||||||||  |||||||||
3'-NNNCGCGNNNNNNNNNN//NNNNNNNNNCCTACNNNN..adap-ind-5'Biotin
```

8. Wash and ligate on methyl-adapter. The second adapter is specific for the sticky end generated at the site recognized by the methylation sensitive restriction endonuclease. Ligation of the second adaptor is most efficient when the DNA has been cut by the methylation sensitive restriction enzyme (when methylation is not present in this example). When the DNA is not cut, there is no sticky end available for ligation. Therefore, regions of genomic DNA methylated in a manner that inhibit cleavage will not be substrates for subsequent steps.
  Example: Ligation of second adapter to DNA cut by methylation sensitive restriction enzyme.

9. Amplification of the immobilized gDNA fragment library via PCR or other suitable amplification technologies. Amplification primers are designed to be complementary to the appropriate strand of each of the adapters.
  Example: Amplicons generated by PCR

```
5'-sec-adap..NNNG CGCNNNNNNNN//NNNNNGGATGnnnn..adap-ind-3'(bases 1-4 and 5-14 of SEQ ID NO:14 and
             ||||    ||||||||  ||||||||||||||             bases 7-19 of SEQ ID NO:13)
3'-sec-adap..NNNCGC GNNNNNNNN//NNNNNCCTACNNNN..adap-ind-5'-Biotin
```

```
5'-sec-adap..NNNGCGCNNNNNNNN//NNNNNGGATGnnnn..adap-ind-3'(SEQ ID NO:14 and bases 7-19 of SEQ ID NO:13)
             ||||||||||||||  ||||||||||||||
3'-sec-adap..NNNCGCGNNNNNNNN//NNNNNCCTACNNNN..adap-ind-5'-Biotin
```

```
5'-sec-adap..NNNGCGCNNNNNNNN//NNNNNGGATGnnnn..adap-ind-3'(SEQ ID NO:14 and bases 7-19 of SEQ ID NO:13)
              ||||||||||||||  ||||||||||||||
3'-sec-adap..NNNCGCGNNNNNNNN//NNNNNCCTACNNNN..adap-ind-5'
```

10. A digestion step with T7 gene 6 exonuclease may be employed to generate single-stranded amplicons. This step requires that one of the primers used for amplification has been synthesized with 5 phosphorothioate linkages substituting for phosphodiester linkages at the 5' end of the primer. The strand containing the phosphorotioate linkages is protected from digestion.

Example: Single-stranded amplicon after exonuclease digestion.

```
3'-sec-adap..NNNCGCGNNNNNNNN//NNNNNCCTACNNNN..adap-ind-5'   (complementary strand of SEQ ID NO:14 and
                                                             complementary bases 7-20 of SEQ ID NO:13)
```

11. Hybridize to ligator-detector probes.

Example: gDNA amplicon hybridized with ligator-detector which has a 5' phosphate group. The ligator-detector has a label, such as a fluorescent molecule attached at the 3' end.

silico analysis of predicted methylation sites should facilitate such assumptions. If genomic sequence is unavailable, the sequence tag can serve as a starting point to facilitate characterization of previously undefined genomic DNA regions of interest.

Variable Address Analysis of Sequence Tags (VAAST)

Variable address analysis of sequence tags (VAAST) is a form of the FAAST method that allows determination of associations, in a nucleic acid molecule, of different combinations of known or potential sequences. For example, particular combinations of joining and variable regions in immunoglobulins or T cell receptors can be determined. VAAST uses the same basic steps as FAAST and adds a step prior to cleavage of the nucleic acid sample. In VAAST, a

```
                              5'-nnnn-lig-detect-Signal.A
                                 ||||||||||||||
3'-sec-adap..NNCGCGNN//NNCCTACNNNNNNNNNNnnnn..adap-ind-5'(complementary bases 2-9 of
                                                          SEQ ID NO:14 and SEQ ID NO:16)
```

12. Hybridize to universal detector array. Each of the 256 preparations of genomic DNA containing a hybridized ligator-detector probe is contacted with a comprehensive array of detector probes, consisting of all 4,096 possible hexamers. The hexamer probes on the array are distributed in a particular order. The probes are preferably spaced away from the surface of the array, preferably by a non-polynucleotide linker spacer.

Example: Detector-ligator joined to immobilized hexamer.

recognition site for cleavage, preferably a restriction enzyme recognition site, is introduced into nucleic acid fragments in the nucleic acid sample. This recognition site is then used as the target of cleavage in the basic FAAST method. The adaptor-indexers should be chosen to match known or potential sequences that would appear adjacent to the sequence into which the recognition site was introduced. The result is fragments with defined end sequences surrounding a central sequence derived from a nucleic acid

```
        Surface---linker spacer----NNNNNN-3'
                              5'-nnnn-lig-detect-Signal.A
                                 ||||||||||||||
3'-sec-adap..NNCGCGNN//NNCCTACNNNNNNNNNNnnnn..adap-ind-5'(complementary bases 2-9 of
                                                          SEQ ID NO:14 and SEQ ID NO:16)
```

The fluorescent signals in each of the 256 generic detector arrays are measured using a suitable fluorescence scanning instrument or fluorescent beads.

Example: Tag sequence (5 known+3 unknown+10 known bases) for each array address. The sequence of the methylation site, at some unknown distance, is also identified.

fragment. This allows the association of known or potential sequences to be assessed. In particular, the association of the sequence into which the recognition site was introduced with a particular adaptor-indexer (which has sequence matching the known or potential adjacent sequence) can be detected.

```
        <<methyl site    5   (3)   6 + 4
3'-sec-adap..NNCGCGNN//NCCTACNNNNNNNNNNnnnn..adap-ind-5'(complementary bases 2-9 of
                                                         SEQ ID NO:14 and SEQ ID NO:16)
```

13. Characterization of derived sequence information. If genomic sequence information available, a BLAST search using the derived sequence may indicate the presence of a promoter if the sequence lies 5' of a characterized gene. In VAAST can be further understood through the following illustration.

1. Isolate RNA and make cDNA (DNA) from the samples of interest.

2. Select a set of two PCR primers, one specific for the V region, one specific for the J region (or D or C region if desired). In the first preferred method (there are several), the V primer contains a Type II-S restriction site, say FokI. Furthermore, the V specific primer contains several phosphorothioate linkages at the 5' end. The length of the amplicon is controlled by placement of the primers.

Example: cDNA target:

```
                                              (SEQ ID NO:17 & 18)
         V        |(N) |    J       /     / C
5'-GATCTAGATCAGTNNNNNNNTGACCATGT.....CGTGAATCATG-3'
   |||||||||||||||||||||||||||||    |||||||||||
3'-CTAGATCTAGTCANNNNNNNACTGGTACA.....GCACTTAGTAC-5'
```

Example of cDNA arnplicon, with introduced FokI site:

```
                                              (SEQ ID NO:19)
         V        |(N) |    J
5'-GATCTGGATGAGTNNNNNNNTGACCATGT......-3'
   ||||||||||||||||||||||||||||||
3'-CTAGACCTACTCANNNNNNNACTGGTACA......-5'
```

3. After PCR, the amplicons are digested with FokI and an adapter-indexer is ligated. This readies the amplicon for digestion with T7 exonuclease gene 6. The 5' end of the adapter-indexer is not protected from T7 exonuclease gene 6 digestion. Hence, a digestion step with T7 exonuclease gene 6 will generate single-stranded amplicons.

cDNA amplicon from step 2

```
     FokI digestion            (bases 1–19 of SEQ
         V        |(N) |        ID NO:20)
5'-GATCTGGATGAGTNNNNNN-3'
   ||||||||||||||||||||

3'-CTAGACCTACTCANNNNNNNACTG-5'  (bases 20–34 of SEQ
      adapter-indexer             ID NO:20)
5'-TGACXXXXXXXXX-3'
   |||||||||
       3'-YYYYYYYYY-5'
```

4. After PCR, the amplicons are digested with T7 exonuclease gene 6.

Example of T7 exonuclease gene 6 treated amplicon:

```
                                              (SEQ ID NO:20)
       V_x    |(N) |    J_y   | adapter-indexer
5'-GATCTGGATGAGTNNNNNNNTGACXXXXXXXXXXX......-3'
```

5. Single stranded amplicons are hybridized to a pool of 100 V ligator-detectors, each containing a label and each specific for a single V region gene segment. All V ligator-detectors (about 25 bases long) are designed a priori to hybridize specifically to a single V region gene segment. The V and J subscript numbers are chosen arbitrarily here for illustration purposes.

```
                                              (SEQ ID NO:21)
         V_1           |(N) |      J_10
5'-GATCTAGATCAGTNNNNNNNTGACCATGT......-3'
3'-signal-ligator-detector-V_1-5'
```

```
                                              (SEQ ID NO:22)
         V_1           |(N) |      J_1
5'-GATCTAGATCAGTNNNNNNNACTGATCGG......-3'
3'-signal-ligator-detector-V_1-5'
```

```
         V_2           |(N) |      J_10
5'-GTTATACTGCAACNNNNNNNTGACCATGT......-3'
3'-signal-ligator-detector-V_2-5'
```

Note that in this example, both $V_1$ ligator-detector and $V_2$ ligator-detector will generate a signal by hybridizing and ligating to the $J_{10}$ probe. In addition, $V_1$ ligator-detector will generate a signal from the $J_1$ address; hence the name variable address analysis of sequence tags. The address of the hybridized complex will be dependent upon which J region gene segment the V gene segment has joined to. This same principle would hold true for all 100 V gene segments.

6. The amplicon/adapter indexer complexes are contacted with a comprehensive address array containing oligonucleotide probes specific for all known J gene segments and those sequences created by the addition of 6 nucleotide bases between the V and the J. Because of the small number of J segments (50), it is not necessary to limit the size of the probes to 6 bases. A preferred length may be 8 to 15 bases or longer if more stringent conditions are desired to increase hybridization fidelity.

```
                                              (SEQ ID NO:24)
V             |(N) |       J
        5'-GATCTAGATCAGTNNNNNNNTGACCATGT......-3'
        3'-V1-adapter indexer-5'NNNNNNNACTGGTACA...-linker/
                                             spacer-surface
```

Illustration of probe complexity required to cover all possible sequences generated at the N region:

| Number of<br>N region bases | Number of possible<br>N region sequences | Number of Js | Number of<br>sequences |
|---|---|---|---|
| 0 | 0 | 50 | 50 |
| 1 | 4 | 50 | 200 |
| 2 | 16 | 50 | 800 |
| 3 | 64 | 50 | 3,200 |
| 4 | 256 | 50 | 12,800 |
| 5 | 1024 | 50 | 51,200 |
| 6 | 4096 | 50 | 204,800 |
|   | 5461 |   | 273,050 |

Therefore, assuming all possible sequences are generated at the N region and that all J gene segments are utilized, there would be 273,050 sequences possible. If one further assumes that all 100 V gene segments are used, then the total number of sequences possible would be:

100×273,050=27,305,000—just over twenty seven million sequences.

The following observations expand the sequence complexity that could be interrogated 10–100 fold:

Observation 1: Although not taken into account here, it is well established that N region additions can exceed six bases, although zero to six appear to be the most common.

Observation 2: Additional complexity comes from a phenomenon known as DNA editing, in which bases at the 3' end of the V region and the 5' end of the J region are "nibbled" back to generate still more diversity. For simplicity, DNA editing is not accounted for in this illustration.

Observation 3: Finally, the Ig and TCR receptor families described here are expressed as heterodimers on the cell surface. For instance, the TCR-alpha chain associates with the TCR-beta chain. It is therefore a simple task to generate a chip that could simultaneously interrogate a cDNA preparation for sequence variability in both the alpha and beta genes.

Observation 4: The full diversity of the TCR or Ig sequences assumes any combination of V, D, J, and C regions. The potential combinations include VDJC, VNDJC, VJC, VNJC, VDDJC, VNDDNJC, VDNDNJC, VNDNDNJC, and any combination of these.

Mass Spectroscopy Detection

Mass spectrometry techniques can be utilized for detection in FAAST. These techniques include matrix-assisted laser desorption/ionization time-of-flight (MALDI-TOF) mass spectroscopy. Such techniques allow automation and rapid throughput of multiple samples and assays.

Mass spectrometry detection works better with smaller molecules so it is useful to cut some FAAST components prior to, or as part of mass spectrometry detection. A number of methods are contemplated where an oligonucleotide molecule to be detected is cut to a shorter length prior to detection by mass spectrometry. The FAAST protocol would proceed as normal and, in the preferred embodiment, the surface that has the hexamer probes attached would be compatible with the source region of a matrix assisted laser desorption ionization, time of flight, mass spectrometer (MALDI-TOF-MS). The resultant fragment of the FAAST process with FokI index cut would look something like defined (approximately 30 bases) which may be used to advantage to generate the parent as well as the fragmentation set. Metal containing porphyrins attached to oligonucleotides have been shown to cut DNA very near the porphyrin when exposed to light (texaphyrins, U.S. Pat. No. 5,607,924). One could denature and use a hybridization texaphryin and light to cleave the remaining strand. Another cleavage technology is that of Dervan (Cartwright, I. L., et al., Cleavage of chromatin with methidiumpropyl-EDTA. iron (II). Proc Natl Acad Sci USA, 1983. 80(11): p. 3213–7; Schultz, P. G. and P. B. Dervan, Sequence-specific double-strand cleavage of DNA by penta-N-methylpyrrolecarboxamide-EDTA X Fe(II). Proc Natl Acad Sci USA, 1983. 80(22): p. 6834–7). Techniques using photocleave linkages are described by Olejnik et al. (Olejnik, J., et al., Photocleavable peptide-DNA conjugates: synthesis and applications to DNA analysis using MALDI-MS. Nucleic Acids Res, 1999. 27(23): p. 4626–31; Olejnik, J., E. Krzymanska-Olejnik, and K. J. Rothschild, Photocleavable affinity tags for isolation and detection of biomolecules. Methods Enzymol, 1998. 291: p. 135–54; Olejnik, J., E. Krzymanska-Olejnik, and K. J. Rothschild, Photocleavable aminotag phosphoramidites for 5'-termini DNA/RNA labeling. Nucleic Acids Res, 1998. 26(15): p. 3572–6; Olejnik, J.,

```
Surface---3'HHHHHHNNNIIIIXXXXXXXXXXXXXXXXXXXXXXXXX-L-3'
             XXXXXXXXXXXXXXXXXXXXXXXXXXXXXXXXXXXXXX-5
             /
3'...YYYYYYYYY
```

Where:

H are the hexamer probe, ligated to the fragment;

I are the quadramer from the indexing step;

N are the unknown bases not read out by FAAST;

X are complementary bases, not germane;

Y are the remaining nucleotides of the FAAST fragment;

- are linker, universal bases, mimics or other analogs;

L is a label;

bold indicate a possible sub-fragment.

For fragments of greater than approximately 50 bases the performance of mass spectrometry techniques degrades for DNA samples. Chemical, biological, physical (thermal), and other cleaving reagents can be used to generate smaller, more optimal, sub-fragments to be analyzed in the mass spectrometer. The degree of fragmentation is somewhat tunable in instruments like the Q-TOF systems (Micromass, US head office at Suite 407N, 100 Cummings Center, Beverly, Mass. 01915-6101, USA.) where one can look at the parent ion, then increase the fragmentation to see the decomposition fragments and thus the sequence; such a technique is contemplated to determine the full sized sub-fragment, and infer the sequence (which is longer sequence information than for the basic FAAST method) of the sub-fragment through these known tools. The detectable fragment can be top strand, bottom strand, or both strands depending upon the scheme. The label may be a cleavable mass tag or the strand need not be labeled.

There are several useful cleaving reagents for this purpose. For example, one technique is that of Szybalski (described elsewhere herein) where FokI is used to cut at a fixed distance from an arbitrary, specific, recognition site. This technique can be extended to other restriction enzymes of type II-S or type III. One could also use this technique twice, once to trim off the end nearer the surface, once to trim off the end further from the surface; preferably one would use a type II enzyme to cut the end furthest from the surface.

Use of McrBC (NEB, #272), can be used to cut at methylcytosine sites adjacent to G/A. The cut site is not well E. Krzymanska-Olejnik, and K. J. Rothschild, Photocleavable aminotag phosphoramidites for 5'-termini DNA/RNA labeling. Nucleic Acids Res, 1998. 26(15): p. 3572–6; Olejnik, J., et al., Photocleavable biotin derivatives: a versatile approach for the isolation of biomolecules. Proc Natl Acad Sci USA, 1995. 92(16): p. 7590–4). These linkages can be cleaved using light to release the fragment from the surface, thus allowing one to provide a more gentle desorption. WO 0004036 describes photocleavable nucleotides and methods for their use.

In one embodiment, a mass label such as peptide nucleic acid (PNA) molecules (Hanvey et al., Science 258:1481–1485 (1992)) of different sequence and molecular weight can be used as labels that bind specifically to sequence in ligator-detectors or adaptor-indexers. Laser desorption of the samples is used to generate MALDI-TOF mass spectra of the PNA labels, which are released into the spectrometer and resolved by mass. The intensity of each PNA label reveals the relative amount of different components (e.g. ligator-detectors or adaptor-indexers. In other words, the PNA spectra generate scalar values that are indirect indicators of the relative abundance of the labeled component at specific locations in an array.

Probability Detection

Sequencing by hybridization is known to produce mismatch errors (Lipshutz, R. J., Likelihood DNA sequencing by hybridization. J Biomol Struct Dyn, 1993. 11(3):637–53). Database searching for sequence information currently is regular expression based and requires matched "letters" between the database entry and the search sequence. FAAST allows replacement of regular expression matching (match versus no-match per base) with a probability function to determine a confidence in the assignment of the identity of a sequence tag (that is, the fragments produced in FAAST).

The FAAST method uses ligation to improve the specificity of the hybridization near the ligation site. Despite this improvement, there will remain a finite probability of a mismatch, particularly for nucleotides more removed from the ligation site. The error rate depends on least two mismatch properties:

base pairing, i.e. A with G;

distance from the ligation site.

As an illustration of the process to determine the confidence value, consider the two bases in a hexamer probe furthest from the ligation site, numbering the bases as shown here.

```
                        <hexamer>
surface-linker-spacer-NNNNNNnnnn-ligator-detect-signal-3'<probe>
                      ||||||||||||||||||||||||||||
           3'-adapter..NNNNNNNNNNnnnn-adapter-indexer-5'  <target>
                      123456 <position>
``` where for this particular case one has, surface - - - linker-spacer - - - ATXXXX, focusing on the AT (positions 1 and 2) bases for purpose of the immediate illustration.

To evaluate the possible set of sequences represented, weight matrices are used, following Dayhoff (Dayhoff, M. O., R. M. Schwartz, and B. C. Orcutt, A model of evolutionary changes in proteins, in Atlas of Protein Sequence and Structure, M. O. Dayhoff, Editor. 1978, National Biomedical Research Foundation: Washington D.C.) and Venezia (Venezia, D. and P. J. O'Hara, Rapid motif compliance scoring with match weight sets. Comput Appl Biosci, 1993. 9(1):65–9) protein techniques. The coefficient in these matrices will be determined experimentally for the FAAST system. Below is an example of matrices (with illustrative coefficients) representing position 1 and 2, where the columns represent the upper strand nucleotide and the rows represent the lower strand nucleotide. The actual coefficients can be determined empirically.

```
        Position 1                    Position 2

A    T    C    G              A    T    C    G

A[.02,.90,.03,.05]           A[.01,.97,.01,.01]

T[.90,.02,.03,.05]           T[.97,.01,.01,.01]

C[.02,.03,.05,.90]           C[.01,.01,.01,.97]

G[.03,.02,.90,.05]           G[.01,.01,.97,.01]
```

For the case of a perfect match detection on the hexamer ATXXXX the score is determined to be the product of the coefficients of the matrices, shown below here in bold; 0.90×0.97=0.87.

```
        Position 1                    Position 2

A    T    C    G              A    T    C    G

A[.02,.90,.03,.05]           A[.01,.97,.01,.01]

T[.90,.02,.03,.05]           T[.97,.01,.01,.01]

C[.02,.03,.05,.90]           C[.01,.01,.01,.97]

G[.03,.02,.90,.05]           G[.01,.01,.97,.01]
```

A case where a singe base mismatch in one strand occurs, for example A→G in position 1 on the hexamer side, the score is determined in a similar fashion, to be 0.05×0.97=0.05

```
        Position 1                    Position 2

A    T    C    G              A    T    C    G

A[.02,.90,.03,.05]           A[.01,.97,.01,.01]

T[.90,.02,.03,.05]           T[.97,.01,.01,.01]

C[.02,.03,.05,.90]           C[.01,.01,.01,.97]

G[.03,.02,.90,.05]           G[.01,.01,.97,.01]
```

This procedure can be extended to an arbitrary number of bases in a similar manner. For a given number of nucleotides the score can be computed for all possible mismatches and rank ordered to reveal the most probable identity. A cut-off score can be used to reduce the number of possible identities from the matrix estimation. For example using the example matrices above, sequences with a threshold score above 0.50 would yield only one sequence, that being a sequence which matches the probe.

This method of estimating sequences and their respective probability scores from the universe of mismatch events for a said probe can from extended from 1 to n, where n is the number of free bases available for hybridization.

In an organism that has not been completely characterized (i.e. at least sequenced and consensus sequence assembled) one can compute a confidence value for uniqueness if one assumes a random distribution of bases. For example, if one has a candidate of 15 bases in length, in an organism which has an estimated $10^8$ base genome, one expects the 15 base fragment to be unique because $10^8/4^{15}$=0.1 is much less than 1. The genome would have to be 10 times larger before one would expect an occurrence of two instances of the particular 15 base fragment.

The distributions, in known genomes, are known not to be completely random and the initial assumption of a random distribution can be improved as information is gathered. This new information can be used to assign and use confidence values.

As an example, consider a fictitious gene family ABCD, whose members are ABCD1, ABCD2 and ABCD3. The three members were discovered following some event such as heat shock, and they are thus putatively assigned to belong to the heat shock family of genes and happen to have significant stretches of conserved sequence among the family of genes. Also consider the organism to be a plant, where ABCD1 was isolated from the plant root, ABCD2 was isolated from the plant leaf, and ABCD3 was isolated from the plant flower. The estimation matrix may look like

```
                    1       2       3

ABCD1[.60, .15, .05]

ABCD2[.25, .60, .15]

ABCD3[.05, .15, .60]
``` where the column 1 represents root, column 2 represents leaf and column 3 represents flower.

In a single experiment where one has high confidence in the sequence but the sequence may belong to one of the three known members of the family, the source of the sample (i.e. root, leaf or flower) allow estimation of the identity of the gene. For the fully mathematically closed treatment the matrix must contain all elements of the family, here to allow for a still to be found gene in this family, the rows and columns do not add to 1; all the other members are assigned a sum of 0.05, the values to be updated as the amount of information known about the organism increases.

One can extend this estimation to include organism homology. That is, if one were to search a database of all organisms for a FAAST tag from gene ABCD1 of Plant 1 there may be matches to Plant 2, Plant 3, Mammal 1, etc. The estimation matrix would be constructed from the known organism data in the database.

The calculations and analysis described above can be illustrated using the following example of construction of a catalog. Consider a two probe detector array, a control sample, and a tester sample. Consider the two probes to have the known sequences: A, <substrate - - - linker - - - AGGGAG-3'>, and, B, <substrate - - - linker - - - ATG-GAG>. These probes will capture their cognate sequence: AA, < . . . TCCCTC . . . >, and, BB, < . . . TACCTC . . . > from the control and tester samples, as well as some mismatched species with lower probability as described herein. Utilizing the estimation matrix technique as discussed above one calculates the probabilities of the correct matching.

The FAAST procedure is conducted on the control and tester, resulting signals are collected from the probe detector array, and a catalog is made which contains the four signals:

|   | control | | | tester | |
|---|---|---|---|---|---|
|   | AA | BB |   | AA | BB |
| A | .30 | .03 | A | .80 | .10 |
| B | .03 | .50 | B | .03 | .50 |

The catalog also contains the probabilities, and/or entries derived from the probabilities, for each probe/target combination, as discussed above. For purpose of illustration, let us assume that the probability of having probe sequence A paired with target sequence AA is 0.80, and the probability of having probe sequence A paired with sequence BB is 0.10, probe sequence B paired with target sequence AA is 0.05, and the probability of having probe sequence B paired with sequence BB is 0.75, or

|   | estimation | |
|---|---|---|
|   | AA | BB |
| A | .80 | .10 |
| B | .05 | .75 |

It is a simple matter of application of linear algebra to determine the signals corresponding to each target. Here, for example, multiplying the corresponding entries together to convert the control and tester to the pattern corresponding to the probabilistic pattern of the target of interest. For example, the total signal ascribed, in the control sample, to AA target is 0.30×0.80 (on A probe site, perfect match)+ 0.03×0.05 (on B probe site, imperfect match)= approximately 0.24. On the tester sample, the AA target signal is 0.80×0.80+0.03×0.05=approximately 0.64. Comparison of the pattern for the control and tester, for the sequence corresponding to AA, exhibits an increase in the relative amount of AA from 0.24 to 0.64 for control to tester respectively. All other entries in the pattern are calculated in the same fashion.

Illustrations

The disclosed method can be further understood by reference to the following illustrations.

Illustration 1—FAAST

1. Double-stranded cDNA is prepared with reverse transcriptase, using standard procedures.

2. The double-stranded cDNA is cleaved with a class II-S restriction endonuclease. Any one of several available class II-S enzymes may be used or this step. A preferred class II enzyme will recognize a unique 5-base sequence in the cDNA, and will cleave at a site located 8 or 9 bases downstream of the recognition sequence. The number of possible cleavage sites comprises a total of 256 different sequences, resulting in the generation of any of 256 different 4-base sticky ends. Examples of suitable enzymes for this step are BbvI (recognition, GCAGC→N8 cleavage), and FokI (recognition, GGATG→N9 cleavage).

Example: cleavage with FokI

```
NNNNNNNNNGGATGNNNNNNNNNN-3'        (bases 3-24 of SEQ
|||||||||||||||||||||||            ID NO:13)
NNNNNNNNCCTACNNNNNNNNNNnnnn -5'
```

3a. Using 384-well microtiter dishes, the cDNA digest is separated into 256 equal aliquots, and each aliquot is incubated with a first adaptor-indexer in the presence of T4 DNA ligase. The process of linking adaptors to the sticky ends generated by class II-s enzymes has been denominated "indexing" (Unrau and Deugau, Gene 145:163–169 (1994)). There are 256 different first adaptor-indexers, corresponding to the 256 possible 4-base sticky ends generated by the cDNA digest. The adaptors contain a biotin moiety at the non-ligating end, so as to enable immobilization of the adaptor in a subsequent step.

Example: ligation of first adaptor indexer (one of 256)

```
                                    (bases 3-24 of SEQ ID NO:13)
NNNNNNNNNGGATGNNNNNNNNNN    nnnn-adaptor-indexer-3'
|||||||||||||||||||||||         ||||||||||||||
NNNNNNNNCCTACNNNNNNNNNNnnnn    -adaptor-indexer-Biot (bases 3-28 of SEQ ID NO:13)
NNNNNNNNNGGATGNNNNNNNNNNnnnn-adaptor-indexer-3'
|||||||||||||||||||||||||||||||||||||||
NNNNNNNNCCTACNNNNNNNNNNnnnn-adaptor-indexer-Biot
```

3b. The ligated material is incubated in the presence of phage T4 endonuclease VII, under mismatch cleavage conditions (Youil et al., *Genomics* 32:431–435 (1996)). This step will cleave any ligated DNA where the adaptors had been joined to an imperfectly paired sticky end. Thus, this step performs error-checking of the previous ligation step. This step is optional.

4a. Each of the 256 cDNA aliquots is digested with a single specific restriction endonuclease that recognizes a unique 4-base sequence. Any four-cutter enzyme that is a frequent cutter is suitable for this step. This digestion will result in cleavage of the majority of those cDNAs that already contain a ligated first adaptor-indexer. After this digest, the cDNA fragments will comprise a heterogeneous population with a mean size of 100 to 200 bases, depending on the specific pair of class II-S and 4-cutter restriction enzymes used. A cDNA fragment will comprise a useful tag for future analysis if it contains a ligated adaptor and a sticky end. This step is optional.

4b. The material from each of the 256 reactions is placed on a separate microtiter well containing immobilized avidin, in order to bind the biotinylated adapters on the surface. This step will result in the immobilization of all the fragments that were successfully ligated to adaptors in step 3. Any unbound fragments are removed by washing. The resulting collection of 256 immobilized fragment sets is called the immobilized cDNA fragment library. This step is optional.

Example: Surface-immobilized tag with a four-cutter sticky end
```
5'-nnnnNNN...NNNGGATGNNNNNNNNNNnnnn-adaprot-indexer-3'     (bases 8-28 of SEQ ID NO:13)
   ||||||||||||||||||||||||||||||||||||||||||||
   3'NNN...NNNCCTACNNNNNNNNNNnnnn-adaptor-indexer-Biot-SURF
```

5. Each member of the immobilized cDNA fragment library is incubated with a second adaptor, in the presence of DNA ligase, in order to join the immobilized cDNA fragments to a universal priming sequence. Unligated adaptors are removed by washing. This step is optional.

Example: Immobilized cDNA tag with two adaptors

```
second.adap-nnnnNNN...  (bases 8-28 of SEQ ID)
||||||||||||||||||||||  NO:13)
second.adap-nnnnNNN...

...NNNGGATGNNNNNNNNNNnnnn-adaptor-indexer-3'
||||||||||||||||||||||||||||||||||||||
...NNNCCTACNNNNNNNNNNnnnn-adaptor-indexer-Biot-SURF
```

6a. All members of the immobilized cDNA fragment library are amplified using a suitable amplification method, such as PCR. A total of 256 separate amplification reactions are performed. Two amplification primers are used, one designed to be complementary to a strand of the second adaptor, and another designed to be complementary to the first adaptor-indexer. The primer complementary to the first adaptor-indexer is one of 256 possible primer sequences, overlapping by four bases with only one of the 4-base sticky ends generated in step 2. Amplification is performed for a total of 12 to 18 cycles using PCR. This step is optional.

Example: Amplicons generated by PCR

```
second.adap-nnnnNNN...NNNGGATGNNNNNNNNNNnnnn-adaptor-indexer-3'  (bases 8-82 of SEQ ID NO:13)
|||||||||||||||||||||||||||||||||||||||||||||||||||||
second.adap-nnnnNNN...NNNCCTACNNNNNNNNNNnnnn-adaptor-indexer-5'
```

6b. A digestion step with T7 exonuclease gene 6 (Nikiforov et al., *PCR Methods and Applications* 3:285–291 (1994)) may be employed to generate single-stranded amplicons. This digestion step assumes that one of the primers used in 6a had been synthesized with 5 phosphorothioate linkages substituting for phosphodiester linkages at the 5' end of the primer (Nikiforov et al. (1994)). These linkages protect one strand from digestion. This step is optional.

Example: Single-stranded amplicon after exonuclease digestion

```
second.adaptor-nnnnNNN..NNNCCTACNNNNNNNNNNnnnn-adaptor-indexer-5'   (complementary bases 8-27 of
                                                                     SEQ ID NO:13)
```

6c. There exist alternative methods for generating amplified tags in step 6. One example is the Strand Displacement Amplification method of Walker et al., *Nucleic Acids Research* 20:1691–1696 (1992). Yet another method for amplification of cDNA tags is rolling Circle Amplification (Lizardi et al., *Nature Genetics* 19:225–232 (1998); U.S. Pat. No. 5,854,033 to Lizardi). In order to use rolling circle amplification, it is necessary to generate circularized cDNA tags by ligation. Ligation methods for generating circularized double stranded DNA are well known in the art. This step is optional.

7a. Each of the 256 preparations of amplified cDNA tags is transferred to another 384-well microtiter dish and hybridized with a fluorescence-labeled detector-ligator oligonucleotide. There are 256 different sequences of ligator-detector oligonucleotides, which comprise the 256 different ligator-detectors complementary to each of the 4-base sticky ends generated in step 2. Only the specific cognate sequence is used for each of the 256 amplified cDNA tags. The ligator-detectors contain a 5'-phosphate group.

Example: cDNA amplicon hybridized with phosphorylated ligator-detector

```
                    5'-nnnn-ligator-detect-SIGNAL.A    (complementary bases 8-27 of SEQ
                       ||||||||||||||||||||            ID NO:13)
2nd.adap-nnnnNNN...NNNCCTACNNNNNNNNNNnnnn-adaptor-indexer-5'
```

7b. For more accurate expression profiling of control vs. tester mRNA populations, this step may incorporate a second set of detector-ligator oligonucleotides labeled with a fluorescent dye of a different color. Thus, control tags are hybridized with 256 oligonucleotides of color "A", while tester tags are hybridized with 256 oligonucleotides of color "B". After hybridization is complete, paired sets of cDNA tags are mixed, and one proceeds to step 8 below.

Example: cDNA amplicon hybridized with phosphorylated ligator-detector

9. To minimize hybridization errors, an error-checking step is performed after ligation. This error-checking step will cleave incorrectly paired bases (those containing mispaired C or T) in the ligator-detector probe. The step is performed using the chemical cleavage of mismatched bases as described (Ellis et al., *Human Mutation* 11:345–353 (1998)). While this method will not destroy all incorrectly ligated ligator-detector probes, it will reduce noise at approximately

```
                    5'-nnnn-ligator-detect-SIGNAL.B
                       ||||||||||||||||||||
2nd.adap-nnnnNNN...NNNCCTACNNNNNNNNNNnnnn-adaptor-indexer-5'  (complementary bases 8-27 of SEQ ID NO:13)
```

8. Each of the 256 preparations of cDNA, which now contain hybridized ligator-detectors, is contacted with a comprehensive probe array. The comprehensive probe array consists of a complete set of 4,096 hexamers (or, alternatively, 16,384 heptamers), ordered on a solid surface, and separated from the surface by a non-polynucleotide linker-spacer. The hexamers (or heptamers) contain free 3'-hydroxyl ends. Each of the 256 detection reactions on the arrays is performed under identical hybridization/ligation conditions, using T4 DNA ligase or any other suitable ligase, in order to achieve ligation of a specific, cognate hexamer sequence to the corresponding sequence adjacent to the 5'-end of a detector ligator probe. After hybridization, any unbound material is removed by very stringent washing.

Example: Detector-ligator joined to immobilized HEXAMER

50% of the array addresses. Other error-checking methods could be used to remove mismatched G's and A's. This step is optional.

10. The fluorescent signals in each of the 256 generic probe arrays are measured using a suitable fluorescence scanning instrument. An expression profile dataset is generated from the combined signals of all 256 arrays. The address of each signal is translated into a known sequence, shown in bold letters.

Example: Determined sequence (5 known+3 unknown+ 10 known bases) for each array address.

```
                            Hexamer
        SURFACE-linker-spacer-NNNNNN-3'

5'-nnnn-ligator-detect-SIGNAL.A
                       ||||||||||||||||||||
2nd.adap-nnnnNNN...NNNCCTACNNNNNNNNNNnnnn-adaptor-indexer-5'  (complementary bases 8-27 of SEQ ID NO:13)

Hexamer
        SURFACE-linker-spacer-NNNNNNnnnn-ligator-detect-SIGNAL.A
                              ||||||||||||||||||||||||
2nd.adap-nnnnNNN...NNNCCTACNNNNNNNNNNnnnn-adaptor-indexer-5'  (complementary bases 8-27 of SEQ ID NO:13)

Hexamer
        SURFACE-linker-spacer-NNNNNNnnnn-ligator-detect-SIGNAL.B
                              ||||||||||||||||||||||||
2nd.adap-nnnnNNN...NNNCCTACNNNNNNNNNNnnnn-adaptor-indexer-5'  (complementary bases 8-27 of SEQ ID NO:13)
```

```
                    5  (3)    6    + 4
second.adap-nnnnNNN...NNNCCTACNNNNNNNNNNnnnn-adaptor-indexer-5'(complementary bases 8-27 of SEQ ID NO:13)
```

11. The expression profile dataset is further analyzed taking into consideration the expected address signatures of highly abundant gene products, which can be predicted from available sequence data. The expression differences between two tissues are measured by the ratio of the two different color signals corresponding to control and tester. A similar experiment should be performed with a different pair of restriction enzymes, in order to resolve inconsistencies generated by cross-hybridization of abundant sequences at incorrect addresses.

Oversampling calculations:

Average mRNA=17000 bases, average tag=120 bases

Number of tags for the average mRNA=4

Thus, the average mRNA is sampled many times, increasing the likelihood of accurate detection.

Considerations on complexity of the sieve:

mRNA complexity=12,000 transcripts*1700 bases→>1×$10^7$

Pentamer=1/1024*Tetramer=1/256*Hexamer=1/4096→>>1/1×$10^9$

Assuming average tag size of 120 bases:

Number of tags=12000*(4)=48,000 tags

Number of tags in each of the 256 microtiter wells=188

Number of different array addresses=256*4,096=1,048,576 (Hexamer)

Number of different array addresses=256*16,384=4,194,304 (Heptamer)

Illustration 2—FAAST

1. Double-stranded cDNA is prepared with reverse transcriptase, using standard procedures.

2. First Digest: The double-stranded cDNA is separated into C equal aliquots (index samples), and each index sample is cleaved with a different six-base recognition restriction endonuclease that generates a sticky end of 2 or 4 bases. Any one of many available restriction endonucleases may be used for this step.

Examples of suitable enzymes for this step include:

| | |
|---|---|
| BamHI | GGATCC (SEQ ID NO: 25) |
| BclI | TGATCA (SEQ ID NO: 26) |
| BglII | AGATCT (SEQ ID NO: 27) |
| BsiWI | CGTACG (SEQ ID NO: 28) |
| BspHI | TCATGA (SEQ ID NO: 29) |
| EcoRI | GAATTC (SEQ ID NO: 30) |

Example: cleavage with one of the C first restriction enzymes (R is a base in the recognition sequence, S is a base in the sticky end (which is also in the recognition sequence, of course), and N is any base):

```
...NNNNNNNNNNNNNNNNNNNNNNNNNNNNNR-3'
...|||||||||||||||||||||||||||||
...NNNNNNNNNNNNNNNNNNNNNNNNNNNNNRSSSS -5'
```

3. First ligation: Each of the C index samples of cleaved, double-stranded cDNA is mixed with a double stranded adaptor-indexer containing the correct sticky end for the corresponding enzyme used in the first digest, and an arbitrary primer complement sequence. There are C different such adaptor-indexers, and each adaptor-indexer has the following structure:

```
                         primer complement
sticky end   SSSSnnnnnnnnnnnnnnnnnnnnn
             |||||||||||||||||||||
             nnnnnnnnnnnnnnnnnnnnn
                    primer sequence of adaptor-indexer
```

A suitable DNA ligase is added, and the adaptor-indexer is thus ligated to all compatible ends present in the cleaved cDNA.

4. Second Digest: Each of the C index samples, containing ligated, double-stranded cDNA, is separated into R (typically 1 to 5) equal aliquots (secondary index samples), and each of these secondary index samples is cleaved with a different mixture of N (typically 1 or 2) different four-base recognition restriction endonuclease. Any mixture of the many available restriction endonucleases may be used for this step, provided that this mixture does not contain the same enzyme used in the first digest. Thus there are C*R possible fractions generated in the process of performing the second digest. The mixture of N enzymes used in the second digestion step can include enzymes such as the following:

| | | | |
|---|---|---|---|
| AciI   | sticky = 2 | CCGC | (SEQ ID NO:31) |
| Hha I  | sticky = 2 | GCGC | (SEQ ID NO:32) |
| TaqI   | sticky = 2 | TCGA | (SEQ ID NO:10) |
| Csp6I  | sticky = 2 | GTAC | (SEQ ID NO:11) |
| Sau3AI | sticky = 4 | GATC | (SEQ ID NO:33) |
| Tsp509I| sticky = 4 | AATT | (SEQ ID NO:34) |
| TaiI   | sticky = 4 | ACGT | (SEQ ID NO:35) |

This second digestion with the mixture of N enzymes will result in cleavage of many of those cDNAs that already contain a ligated adaptor-indexer. After this digest, the cDNA fragments will comprise a heterogeneous population with a mean size of 60 to 300 bases, depending on the specific mixture of N four-base recognition restriction endonucleases used.

5. Each aliquot is incubated with a second adaptor in the presence of T4 DNA ligase. There are N different second adaptors corresponding to the possible 2-base or 4-base sticky ends generated by the mixture of N enzymes. The second adaptors may contain a biotin moiety at the non-ligating end, so as to enable immobilization of the second adaptors in a subsequent step.

Example: ligation of second adaptor (one of N)

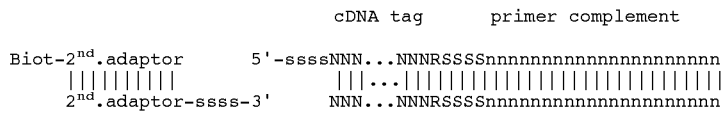

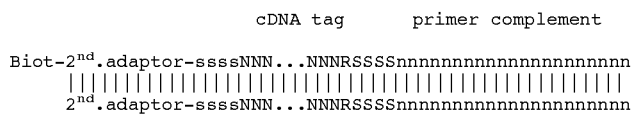

Productive cDNA fragments for further analysis will contain adaptors ligated at both ends.

5b. OPTIONAL: The ligated secondary index samples are incubated in the presence of phage T4 endonuclease VII, under mismatch cleavage conditions (Youil et al., 1996). This step will cleave any ligated DNA where the adaptors had been joined to an imperfectly paired sticky end. Thus, this step performs error-checking of the previous ligation steps.

6. Each secondary index sample is separated into D aliquots, and D-1 of these aliquots (restricted secondary index samples) are digested with a four-base recognition restriction endonuclease that is not included in the set of the four-base recognition restriction endonucleases used in the first digest and the mixture of N four-base recognition restriction endonucleases used in the second digest. The remaining undigested aliquot is the non-restricted secondary index sample. This digestion step will cleave a subset of the fragments and make them not amplifiable in step 7.

6b. (OPTIONAL): The material from each of the C*R*D secondary index samples is placed on a separate microtiter well containing immobilized avidin (or any suitable binding moiety), in order to bind the biotinylated adapters (or any ligand-adapter) on the surface. This step will result in the immobilization of all the fragments that were successfully ligated to second adaptors in step 5, and were not cleaved in step 6. Any unbound fragments are removed by washing. The resulting collection of C*R*D immobilized fragment sets is called the immobilized secondary index samples.

7. All of the immobilized secondary index samples are amplified using suitable amplification method, such as PCR. A total of C*R*D separate amplification reactions are performed. Two amplification primers are used, one designed to be complementary to a strand of the second adaptor, and another designed to be complementary to the adaptor-indexer. The primer complementary to the adaptor-indexer is one of C possible primer sequences, overlapping by 4 bases with the enzyme recognition site of the first digest. The primer complementary to the second adaptor in each of the different R reactions is one of N possible primer sequences, overlapping by 4 bases with each of the enzyme recognition sites of the mixture of N enzymes used in the second digest. Amplification is performed for a total of 12 to 25 cycles using PCR.

Example: Amplicons generated by PCR

7b. There exist alternative methods for generating amplified tags in step 7. One example is the Strand Displacement Amplification method of Walker et al., (1992). Yet another method for amplification of cDNA tags is rolling circle amplification (Lizardi et al., 1998). In order to use rolling circle amplification, it is necessary to generate circularized cDNA tags by ligation. Ligation methods for generating circularized double stranded DNA are well known.

8. A digestion step with T7 exonuclease gene 6 (Nikiforov et al., 1993) may be employed to generate single-stranded amplicons. This digestion step assumes that one of the primers used in step 7 had been synthesized with 5 phosphorothioate linkages substituting for phosphodiester linkages at the 5' end of the primer (Nikiforov et al., 1993). These linkages protect one strand from digestion.

Example: Single-stranded amplicon after exonuclease digestion

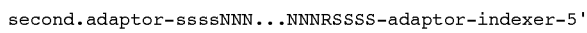

9. Each of the amplified secondary index samples is transferred to another microtiter dish and hybridized with a fluorescence-labeled ligator-detector oligonucleotide. There are C different ligator-detectors, each complementary to one of the adaptor-indexers. Only the specific cognate sequence is used in each of the amplified secondary index samples. The ligator-detectors contain a 5'-phosphate group.

Example: cDNA amplicon hybridized with phosphorylated ligator-detector

9b. For more accurate expression profiling of control vs. tester mRNA populations, this step may incorporate a second set of ligator-detectors labeled with a fluorescent dye of a different color. Thus, control tags are hybridized with C ligator-detectors of "signal type A", while tester tags are hybridized with C ligator-detectors of "signal type B". After hybridization is complete, paired sets of A-coded and B-coded secondary index samples are mixed, and one proceeds to step 10 below.

Example: cDNA amplicon hybridized with phosphorylated ligator-detector

```
                        5'-RSSSS-ligator-detector-SIGNAL.B
                           |||||||||||||||||||||||
second.adaptor-ssssNNN...NNNRSSSS-adaptor-indexer-5'
```

10. Each of the C*R*D secondary index samples, which now contain hybridized ligator-detectors, is contacted with a comprehensive address array (probe array). The comprehensive address array consists of a complete set of 4,096 hexamers (or, alternatively, 16,384 heptamers), ordered on a solid surface, and separated from the surface by a non-polynucleotide linker-spacer. The hexamers (heptamers) contain free 3'-hydroxyl ends. Each of the C*R*D detection reactions on the arrays is performed under identical hybridization/ligation conditions, using T4 DNA ligase or any other suitable ligase, in order to achieve ligation of a specific, cognate hexamer sequence to the corresponding sequence adjacent to the 5'-end of a ligator-detector probe. After hybridization, any unbound material is removed by very stringent washing.

Example: Ligator-detector joined to immobilized hexamer

```
                      Hexamer

SURFACE-linker-spacer-NNNNNN-3'

5'-RSSSS-ligator-detector-SIGNAL.A
                              ||||||||||||||||||||||
     second.adaptor-ssssNNN...NNNNNNRSSSS-adaptor-indexer-5'

Hexamer

SURFACE-linker-spacer-NNNNNNRSSSS-ligator-detector-SIGNAL.A
                      |||||||||||||||||||||||||||
        second.adap-ssssNNN...NNNNNNRSSSS-adaptor-indexer-5'

Hexamer

SURFACE-linker-spacer-NNNNNNRSSSS-ligator-detector-SIGNAL.B
                      |||||||||||||||||||||||||||
        second.adap-ssssNNN...NNNNNNRSSSS-adaptor-indexer-5'
```

11. The signals in each of the C*R*D comprehensive address arrays are measured using a suitable readout instrument. An expression profile dataset is generated from the signal ratios at each address of the C*R*D arrays. The address of each signal is translated into a sequence, shown in bold letters. Six nucleotides from the hexamer probe, five nucleotides from the recognition/sticky end sequence, and one nucleotide from the last base in the recognition sequence.

Example: Determined sequence for each array address.

```
                              6 + 5 + 1
second.adap-ssssNNN...NNNNNNRSSSS-adaptor-indexer-5'

Determined sequence:

NNNNNNRSSSSR (10 nucleotides)
```

Specific signals that disappear in each one of the D-1 restricted secondary index samples derived from a given secondary index sample are indicative of the presence of a specific cleavage site [REST, below] within the cDNA fragment.

```
               4           4         6 + 5 + 1
second.adap-ssssNNN...NNN[REST]NNN...NNNNNNRSSSS-adaptor-indexer Determined sequence:

ssss...[REST]...NNNNNNRSSSSR (4...4...10 = 18 nucleotides)
```

The expression dataset is analyzed taking into consideration the expected address signatures of abundant gene products, which can be predicted from available sequence data. The expression differences between two tissues are measured by the ratio of the two different color signals corresponding to control and tester. When N=1, the sequence ssss sticky end sequence adjacent to the second adaptor is also known.

EXAMPLES

Example 1
Creation of FAAST-indexed DNA Amplicons

Fixed Address Analysis of Sequence Tags or FAAST sorts complex DNA into a collection of small fragments of partially known sequence by a process involving two sequential rounds of digestion with a restriction enzyme followed by ligation to duplex adapters. In the first round, DNA is digested with a II-S type restriction enzyme that cuts at a site distinct from the enzyme recognition site and generates a 5' or 3' overhang of undetermined sequence. Only duplex adapters that contain the complementary overhang will be capable of ligating to the restricted-DNA ends. In the second round, DNA fragments are digested with a restriction enzyme that cuts inside the recognition site and generates a 5' or 3' overhang of known sequence. Duplex adapters of corresponding sequence are subsequently ligated to these ends. In this example, for the first round of digestion we use FokI as the II-S enzyme, which cuts 9 bases from the recognition site and generates a 4-base 5' overhang. For the second round of digestion either NlaIII or DpnII can be used, which are 4-base restriction enzymes that cut within their corresponding recognition sites and generate 3' and 5' 4-base overhangs, respectively. Two yORFs of known sequence are subjected to the two rounds of digestion/ligation and demonstrate that the single PCR amplicon obtained from each yORF corresponds to the expected FAAST-indexed fragment.

In one procedure, two PCR products each containing a unique yeast open reading frame (yORF) were independently processed through the first phase of the FAAST procedure. This phase involves two sequential rounds of digestion with a restriction enzyme followed by ligation of the 4-base overhang produced by the enzymatic cleavage to a compatible adapter oligonucleotide complex. In the first round, carried out in solution, the yORFs were digested with FokI and the restriction ends were ligated to compatible adapter-indexer complexes. In the second round, carried out on a solid surface, the fragments were further digested with either NlaIII or DpnII and ligated to compatible second-adapter complexes. Two end products, one from each yORF, were amplified by PCR. The identity of these FAAST-indexed DNA fragments was determined by restriction map analysis and by sequencing.

The following results were found. In the first round of digestion/ligation, PCR products 1.0 kbp and 1.1 kbp in size corresponding to yORFs YCR100C and YKL051W, respectively (obtained from Research Genetics, Inc.) were digested in separate reactions with FokI. Both PCR products generated four different restriction fragments, as expected from in silico restriction analysis of their respective sequences. Adapter/indexer complexes were made by annealing appropriate pairs of oligonucleotides, one of which contained a biotin moiety at its 5' end. These adapters were designed to complement the 5' 4-base overhang of only one fragment for each yORF. T4 DNA ligase was used to ligate adapter/indexer to FokI-treated DNA under standard conditions using a approximately 20-fold excess of adapter complexes. After incubating 30 minutes at room temperature (about 22° C.), the reactions were passed through AffiniTip streptavidin micro-columns. Only yORF DNA fragments ligated to an adapter/indexer complex are retained in the micro-columns through binding of biotin to streptavidin.

In the second round of digestion/ligation, the following steps were carried out by using 100 μl of reaction buffer to wet the matrix of AffiniTip micro-columns containing streptavidin-bound DNA. DNA from YCR100C and YKL051W was digested with NlaIII and DpnII, respectively, for 1 hour at 37° C. The micro-columns were then washed thoroughly to eliminate enzymes and all DNA fragments that did not contain adapter/indexer. T4 DNA ligase was used to ligate second-adapter complexes to the streptavidin-bound DNA using an excess of adapters compatible with either NlaIII or DpnII 4-base overhangs, as required. Ligation was carried out at room temperature (about 22° C.) for 1 hour, followed by thorough washing of the matrix to eliminate ligase and unreacted adapters.

The following steps were taken to recover single-stranded amplicons. The matrix of AffiniTip micro-columns was soaked in 0.1 M NaOH to denature streptavidin-bound DNA. In this step, the DNA strand containing the biotin moiety remains bound to the matrix while the complementary strand is released into solution. The elution volume (40 μl) was neutralized with 4 μl of 3 M sodium acetate. Single-stranded DNA (ssDNA) was ethanol-precipitated using 5 μg of glycogen as carrier and redissolved in 10 μl of TE buffer. Eluted ssDNA was not detectable using DNA-binding dyes in standard electrophoretic analysis. 1 μl of each eluant was added as template into 50 μl PCR reactions that included a primer pair complementary to indexer and second adapter sequences. The FAAST-indexed amplicons expected from YCR100C and YKL051W are 166 bp and 191 bp, respectively. DNA of the expected size was apparent among the products of the corresponding PCR reaction. Samples from PCR reactions started with dilutions of ssDNA as indicated above the lanes were run on a 4–20% polyacrylamide gel in 1×TBE. Standards were used to determine the size of indicated PCR products. Primer bands and putative PCR artifacts were also identified. Digestion with restriction enzymes that recognize a unique sequence within the predicted FAAST amplicons cleaved these products into fragments of the expected size. DNA from PCR reactions started with 1:10 dilutions of ssDNA were digested with the indicated restriction enzyme. Bands corresponding to intact and restriction fragments were identified. The 166 bp amplicon from YCR100C was cleaved by HpaII into 97 and 69 bp fragments. The 191 bp amplicon from YKL051W was cleaved by HinfI into 111 and 80 bp fragments. The intact products were extracted from the gel and used for further PCR amplification. Sequencing of this material confirmed that it was composed of the expected FAAST amplicon sequences. PCR primer annealing regions and 4-base restriction sites were identified. FokI cleavage and recognition sites in that order were also identified. The same pair of primers used for PCR amplification was used to sequence both strands of the DNA fragments.

In summary, FAAST adapters were successfully ligated to specific restriction fragments from two yORFs, as demonstrated by the production of the expected PCR amplicons. These results demonstrate FAAST-indexing of genomic DNA for use in subsequent hybridization analysis.

Example 2

FAAST Error Correction

The bacteriophage protein T7 endonuclease I binds specifically to heteroduplex DNA and cuts one of the strands one to two bases 5' from the mismatch. This property has made T7 endonuclease I an important tool in studies of DNA structure and mutation analysis. In this example, this enzyme is shown to be useful in mismatch elimination on surface-bound DNA. Error correction of surface-bound nucleic acids has not been demonstrated previously. A mismatch elimination procedure is desirable to correct errors during hybridization of a collection of target DNA strands to hexamer microarrays.

A microarray of probe oligonucleotides was covalently attached to the surface of a glass-slide (SurModics, Inc.) via a poly-ethylene-glycol spacer moiety (PEG). Probe oligonucleotides were composed of a hexamer probe sequence (B, A, D or E), 23 bases of adapter-indexer sequence (23mer) and a fluorophore (Cy5). A 47-base target oligonucleotide was then annealed to the probe molecules under standard conditions. The target sequence is composed of 23 bases (23mer) complementary to the adapter-indexer sequence, 18 bases ($N_{18}$) non-complementary to the probe oligonucleotides and a different fluorophore (Cy3). Hybridization between the probe and target oligonucleotides was determined by measuring the Cy3 fluorescence prior to treatment with T7 endonuclease I.

Upon hybridization, the probe and target molecules form a continuous double stranded helix, except in some positions of the hexamer probe region that are not complementary to the target oligonucleotide. The microarray was treated with T7 endonuclease I for 20 minutes at 22° C. in buffer No. 4 (NEB) supplemented with 100 mM NaCl. Cy5 fluorescence was measured using a General Scanning 3000 (GSI Lumonics) before (Pre-T7) and after (Post-T7) treatment with T7 endonuclease I. Loss of Cy5 signal is expressed as a percentage of the amount of signal detected before treatment with endonuclease. The measurements from replicate microarray dots demonstrated a significantly higher loss of Cy5 signal from the complexes containing base mismatches.

In summary, these results show that T7 endonuclease I can eliminate hybrids with at least two mismatches from a DNA microarray.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

We claim:

1. A method of identifying nucleic acid fragments in a nucleic acid sample, the method comprising
   (a) incubating a nucleic acid sample with one or more nucleic acid cleaving reagents that collectively generate sticky ends having a plurality of different sequences to produce nucleic acid fragments with sticky ends,
   (b) mixing a plurality of adaptor-indexers with the nucleic acid sample and covalently coupling the adaptor-indexers to the nucleic acid fragments, wherein each adaptor-indexer has a different sticky end, wherein each sticky end of the adaptor-indexers is compatible with a sticky end generated by the nucleic acid cleaving reagents,
   (c) hybridizing a plurality of ligator-detectors with the nucleic acid sample, wherein each ligator-detector comprises sequence matching or complementary to all or part of sequence including, and adjacent to, the sticky end of at least one of the adaptor-indexers,
   (d) hybridizing a plurality of detector probes with the nucleic acid sample and covalently coupling the ligator-detectors to the detector probes, wherein each detector probe has a different sequence, and
   (e) detecting, directly or indirectly, coupling of ligator-detectors to the detector probes.

2. The method of claim 1 wherein each adaptor-indexer comprises a sticky end portion and a detection portion, wherein the detector portion of each adaptor-indexer is separately detectable,
   wherein the method further comprises detecting, directly or indirectly, detector portions of the adaptor-indexers.

3. The method of claim 2 wherein each ligator-detector comprises a detector portion, wherein the detector portion of each ligator-detector corresponds to the detector portion of one of the adaptor-indexers, wherein detection of the detection portion of a ligator-detector is an indirect detection of the detector portion of the corresponding adaptor-indexer.

4. The method of claim 2 wherein detection of the detection portion of an adaptor-indexer is an indirect detection of the detector portion of the corresponding ligator-detector.

5. The method of claim 2 wherein the detection portion of at least one adaptor-indexer is a label.

6. The method of claim 1 wherein the adaptor-indexers are covalently coupled to the nucleic acid fragments by ligation, and wherein the ligator-detectors are covalently coupled to the detector probes by ligation.

7. The method of claim 1 further comprising, prior to step (b),
   dividing the sample into a plurality of index samples,
   wherein a different adaptor-indexer is mixed with each index sample, wherein a different ligator-detector is hybridized with each index sample, wherein the ligator-detector in each index sample comprises sequence matching or complementary to all or part of sequence including, and adjacent to, the sticky end of the adaptor-indexer in that index sample.

8. The method of claim 6 wherein the ligator-detector comprises sequence matching or complementary to all or part of the sticky end of the adaptor-indexer and to all or part of the adjacent sequence of the adaptor-indexer used in the index sample.

9. The method of claim 8 further comprising, following step (b), separating the strands of the nucleic acid fragments and proceeding with step (c) using only one of the strands.

10. The method of claim 9 wherein the strands are separated using a capture tag associated with one of the strands.

11. The method of claim 10 wherein the capture tag is associated with the adaptor-indexers.

12. The method of claim 9 wherein the concentration of the various nucleic acid fragments in the index samples are normalized.

13. The method of claim 12 wherein the strands of the nucleic acid fragments are separated and the concentration of the nucleic acid fragments is normalized by immobilizing one strand of the nucleic acid fragments, denaturing the nucleic acid fragments, renaturing the nucleic acid fragments for a time greater than the $c_0t_{1/2}$ for abundant nucleic acid fragments and less than the $c_0t_{1/2}$ for rare nucleic acid fragments, and collecting the un-renatured nucleic acid fragments.

14. The method of claim 8 wherein ligation of the ligator-detector is detected by rolling circle replication of an amplification target circle wherein replication is primed by the ligator-detector.

15. The method of claim 8 wherein the nucleic acid cleaving reagents generate sticky ends having N different sequences, and wherein the sample is divided into N index samples.

16. The method of claim 8 wherein the detector probes are all of the same length.

17. The method of claim 16 wherein the detector probes are six, seven, or eight nucleotides long.

18. The method of claim 8 wherein the detector probes all have similar hybrid stability.

19. The method of claim 8 wherein the nucleic acid cleaving reagents are restriction enzymes.

20. The method of claim 19 wherein the nucleic acid sample is digested with one restriction enzyme, wherein the restriction enzyme generates sticky ends having a plurality of different sequences.

21. The method of claim 20 wherein the restriction enzyme is a type II-S restriction enzyme that cleaves at a site different from its recognition sequence.

22. The method of claim 6 wherein each ligator-detector comprises sequence matching all or part of sequence including, and adjacent to, the sticky end of the adaptor-indexer.

23. The method of claim 6 wherein each ligator-detector comprises sequence complementary to all or part of sequence including, and adjacent to, the sticky end of the adaptor-indexer.

24. The method of claim 6 wherein at least one ligator-detector comprises sequence matching all or part of sequence including, and adjacent to, the sticky end of the adaptor-indexer and at least one ligator-detector comprises sequence complementary to all or part of sequence including, and adjacent to, the sticky end of the adaptor-indexer.

25. The method of claim 6 wherein the concentration of the various nucleic acid fragments in the nucleic acid sample are normalized.

26. The method of claim 25 wherein the concentration of the nucleic acid fragments is normalized by immobilizing one strand of the nucleic acid fragments, denaturing the nucleic acid fragments, renaturing the nucleic acid fragments for a time greater than the $c_0t_{1/2}$ for abundant nucleic acid fragments and less than the $c_0t_{1/2}$ for rare nucleic acid fragments, and collecting the un-renatured nucleic acid fragments.

27. The method of claim 8 wherein each adaptor-indexer, ligator-detector, or detector probe is immobilized on a substrate.

28. The method of claim 27 wherein the detector probes are immobilized on a substrate.

29. The method of claim 27 wherein all of the adaptor-indexers, ligator-detectors, or detector probes are immobilized on the same substrate.

30. The method of claim 27 wherein all of the adaptor-indexers, ligator-detectors, or detector probes are immobilized on a different substrate.

31. The method of claim 30 wherein the substrates are beads.

32. The method of claim 27 wherein the adaptor-indexers, ligator-detectors, or detector probes are immobilized on a plurality of different substrates such that at least one adaptor-indexer, ligator-detector, or detector probe is immobilized on one substrate and at least one other adaptor-indexer, ligator-detector, or detector probe, respectively, is immobilized on a different substrate.

33. The method of claim 27 wherein the adaptor-indexers, ligator-detectors, or detector probes are in an array.

34. The method of claim 33 wherein the detector probes are in an array.

35. The method of claim 8 wherein each adaptor-indexer, ligator-detector, or detector probe is associated with a capture tag, sorting tag, or both.

36. The method of claim 35 wherein the ligator-detectors are associated with capture tags or sorting tags.

37. The method of claim 35 wherein the adaptor-indexers, ligator-detectors, or detector probes are captured via the capture tags.

38. The method of claim 35 wherein the adaptor-indexers, ligator-detectors, or detector probes are sorted via the sorting tags.

39. The method of claim 35 wherein the ligator-detectors are associated with sorting tags, wherein the adaptor-indexers are associated with capture tags.

40. The method of claim 35 wherein the ligator-detectors are associated with capture tags, wherein the adaptor-indexers are associated with sorting tags.

41. The method of claim 35 wherein the detector probes are associated with sorting tags, wherein the adaptor-indexers are associated with capture tags.

42. The method of claim 35 wherein the adaptor-indexers, ligator-detectors, or detector probes are associated with a plurality of different capture tags or a plurality of different sorting tags.

43. The method of claim 8 further comprising determining the sequence of a portion of at least one of the nucleic acid fragments in the nucleic acid sample.

44. The method of claim 43 wherein the nucleic acid cleaving reagents are restriction enzymes,
   wherein the nucleic acid sample is digested with one restriction enzyme, wherein the restriction enzyme generates sticky ends having a plurality of different sequences,
   wherein the restriction enzyme is a type II-S restriction enzyme that cleaves at a site different from its recognition sequence, and
   wherein the portion of the nucleic acid fragments corresponds to the sticky end sequence, the sequence adjacent to the sticky end sequence to which the detector probe hybridized, and the recognition sequence of the restriction enzyme.

45. The method of claim 44 wherein the portion includes a gap of known length but unknown sequence between the sequence adjacent to the sticky end and the recognition sequence of the restriction enzyme.

46. The method of claim 45 wherein the portion has the structure

A-B-C-D wherein A is the recognition sequence of the restriction enzyme, B is the gap of unknown sequence, C is the sequence to which the detector probe hybridized, and D is the sticky end sequence.

47. The method of claim 44 further comprising detecting or amplifying a nucleic acid corresponding to a nucleic acid fragment in the nucleic acid sample using a probe or primer based on the determined sequence of the portion of the nucleic acid fragment.

48. The method of claim 8 wherein the detector probes are in an array, wherein each detector probe is immobilized at a different location in the array, and wherein detecting ligation of ligator-detectors to detector probes is accomplished by detecting the presence of ligator-detector at different locations in the arrays.

49. The method of claim 48 wherein the location, amount, or location and amount of ligator-detectors in the arrays constitutes a pattern of ligator-detectors in the arrays, the method further comprising comparing the pattern of ligator-detectors in the arrays with the pattern of ligator-detectors in arrays determined in a separate procedure using a second nucleic acid sample.

50. The method of claim 49 further comprising comparing the pattern of ligator-detectors in the arrays with the pattern of ligator-detectors in arrays determined in a plurality of separate procedures using a plurality of different nucleic acid samples.

51. The method of claim 8 further comprising, following step (b), incubating the index samples with one or more second nucleic acid cleaving reagents, and mixing a second adaptor with each index sample and ligating the second adaptors to the nucleic acid fragments, wherein each second adaptor has an end compatible with the end generated by one of the second nucleic acid cleaving reagents.

52. The method of claim 51 further comprising, prior to step (c), dividing each index sample into one or more restricted index samples and a non-restricted index sample, incubating each restricted index sample with a different third nucleic acid cleaving reagent, wherein steps (c), (d), and (e) are performed with both the restricted and non-restricted index samples.

53. The method of claim 51 further comprising, prior to incubation with the second nucleic acid cleaving reagents, dividing each index sample into a set of two or more of secondary index samples, wherein each secondary index sample in each set of secondary index samples is incubated with a different set of one or more second nucleic acid cleaving reagents.

54. The method of claim 53 wherein steps (c), (d), and (e) are performed with each secondary index sample.

55. The method of claim 53 further comprising, prior to step (c), dividing each secondary index sample into one or more restricted index samples and a non-restricted index sample, incubating each restricted index sample with a different third nucleic acid cleaving reagent, wherein steps (c), (d), and (e) are performed with both the restricted and non-restricted index samples.

56. The method of claim 55 wherein the first, second, and third nucleic acid cleaving reagents are restriction enzymes.

57. The method of claim 51 further comprising, following incubation with the second nucleic acid cleaving reagents, dividing each index sample into a set of two or more of secondary index samples.

58. The method of claim 57 wherein steps (c), (d), and (e) are performed with each secondary index sample.

59. The method of claim 51 wherein the first and second nucleic acid cleaving reagents are restriction enzymes.

60. The method of claim 51 further comprising, following ligation of second adaptors to the nucleic acid fragments, amplifying the nucleic acid fragments in the index samples to which adaptor-indexers and second adaptors have been ligated.

61. The method of claim 60 wherein the nucleic acid fragments are amplified by PCR.

62. The method of claim 61 wherein the primers used for PCR are complementary to sequence in the adaptor-indexers and second adaptors.

63. The method of claim 8 further comprising, prior to step (a), dividing the nucleic acid sample into a plurality of index samples, wherein more than one nucleic acid cleaving reagent is used in step (a), wherein each index sample is incubated with a different one of the nucleic acid cleaving reagents, wherein a different adaptor-indexer is mixed with each index sample, wherein a different ligator-detector is hybridized with each index sample, wherein the ligator-detector in each index sample comprises sequence matching or complementary to all or part of sequence including, and adjacent to, the sticky end of the adaptor-indexer in that index sample.

64. The method of claim 8 further comprising, following step (b), amplifying the nucleic acid fragments in the index samples to which adaptor-indexers have been ligated.

65. The method of claim 64 further comprising, following amplification, separating the strands of the amplified nucleic acid fragments and proceeding with step (c) using only one of the strands.

66. The method of claim 65 wherein the strands are separated using a capture tag incorporated into one of the strands.

67. The method of claim 66 wherein the capture tag is associated with a primer used for amplification of the nucleic acid fragments.

68. The method of claim 64 wherein the nucleic acid fragments are amplified by PCR.

69. The method of claim 8 further comprising, following ligation in steps (b) and (d), incubating the index samples with a reagent that destroys or alters base mismatches.

70. The method of claim 69 wherein the base mismatch reagent is (1) T4 endonuclease VII, (2) MutH, MutL, and MutS together, (3) T7 endonuclease I, (4) MutY, (5) glycosylase, or (6) topoisomerase I.

71. The method of claim 8 further comprising, prior to ligation in steps (b) and (d), mixing the index samples with a reagent that binds to base mismatches.

72. The method of claim 71 wherein the base mismatch reagent is (1) Mec1, (2) MutS, (3) MSH2-MSH6, (4) MLH1-PMS1, or (5) MSH2-MSH3.

73. The method of claim 8 wherein each adaptor-indexer, ligator-detector, or detector probe contains a label, wherein ligation of the ligator-detectors to the detector probes is detected via the label.

74. The method of claim 73 wherein each ligator-detector contains a label,
wherein detecting ligation of the ligator-detectors to the detector probes is accomplished by
separating ligated ligator-detectors from unligated ligator-detectors, and
detecting the labels of the ligated ligator-detectors.

75. The method of claim 74 wherein each different ligator-detector contains a different label, wherein each detector probe is associated with a capture tag or a sorting tag, wherein separating ligated ligator-detectors from unligated ligator-detectors is accomplished by separating the detector probes from the unligated ligator-detectors using the capture tags or sorting tags, wherein the ligated ligator-detectors separate with the detector probes.

76. The method of claim 75 wherein the sorting tag is a fluorescent label, and wherein separating the detector probes from the unligated ligator-detectors is accomplished using a fluorescent label sorter.

77. The method of claim 73 wherein the labels are fluorescent, phosphorescent, or chemiluminescent labels.

78. The method of claim 77 wherein at least two of the labels are distinguished temporally via different fluorescent, phosphorescent, or chemiluminescent emission lifetimes.

79. The method of claim 73 wherein the labels are detectable by nuclear magnetic resonance, electron paramagnetic resonance, surface enhanced raman scattering, surface plasmon resonance, fluorescence, phosphorescence, chemiluminescence, resonance raman, microwave, or a combination.

80. The method of claim 79 wherein the label is detected using nuclear magnetic resonance, electron paramagnetic resonance, surface enhanced raman scattering, surface plasmon resonance, fluorescence, phosphorescence, chemiluminescence, resonance raman, microwave, or a combination.

81. The method of claim 73 wherein the labels are beads comprising a label.

82. The method of claim 81 wherein the label is a molecular barcode.

83. The method of claim 73 wherein the labels are mass labels.

84. The method of claim 8 further comprising
performing steps (a) through (e) on a control nucleic acid sample,
identifying differences between the nucleic acid sample and the control nucleic acid sample in the pattern of ligator-detectors ligated to different detector probes.

85. The method of claim 84 wherein the ligator-detectors used with the control nucleic acid sample contain a different label from the label of the ligator-detectors used with the nucleic acid sample,
wherein the control index samples are mixed with corresponding index samples prior to step (d).

86. The method of claim 8 further comprising performing steps (a) through (e) on a plurality of nucleic acid samples.

87. The method of claim 86 further comprising
performing steps (a) through (e) on a control nucleic acid sample,
identifying differences between the nucleic acid samples and the control nucleic acid sample in the pattern of ligator-detectors ligated to different detector probes.

88. The method of claim 86 further comprising
identifying differences between the nucleic acid samples in the pattern of ligator-detectors ligated to different detector probes.

89. The method of claim 8 wherein the pattern of the presence, amount, presence and amount, or absence of ligator-detectors ligated to different detector probes constitutes a catalog of nucleic acid fragments in the nucleic acid sample.

90. The method of claim 89 further comprising preparing a second catalog of nucleic acid fragments in a second nucleic acid sample and comparing the first catalog and second catalog.

91. The method of claim 90 further comprising identifying or preparing nucleic acid fragments corresponding the nucleic acid fragments present at a threshold amount in the first nucleic acid sample but not present at the threshold amount in the second nucleic acid sample.

92. The method of claim 90 wherein the second nucleic acid sample is a sample from the same type of organism as the first nucleic acid sample.

93. The method of claim 90 wherein the second nucleic acid sample is a sample from the same type of tissue as the first nucleic acid sample.

94. The method of claim 90 wherein the second nucleic acid sample is a sample from the same organism as the first nucleic acid sample.

95. The method of claim 94 wherein the second nucleic acid sample is obtained at a different time than the first nucleic acid sample.

96. The method of claim 90 wherein the second nucleic acid sample is a sample from a different organism than the first nucleic acid sample.

97. The method of claim 90 wherein the second nucleic acid sample is a sample from a different type of tissue than the first nucleic acid sample.

98. The method of claim 90 wherein the second nucleic acid sample is a sample from a different species of organism than the first nucleic acid sample.

99. The method of claim 90 wherein the second nucleic acid sample is a sample from a different strain of organism than the first nucleic acid sample.

100. The method of claim 90 wherein the second nucleic acid sample is a sample from a different cellular compartment than the first nucleic acid sample.

101. The method of claim 90 further comprising identifying or preparing nucleic acid fragments corresponding the nucleic acid fragments present in the first nucleic acid sample but not present in the second nucleic acid sample.

102. The method of claim 101 further comprising using the nucleic acid fragments as probes.

103. The method of claim 102 wherein using the nucleic acid fragments as probes is accomplished by repeating steps (a) through (e) with a different nucleic acid sample, wherein the nucleic acid fragments are used as detector probes in steps (d) and (e).

104. The method of claim 8 wherein the pattern of the amount of ligator-detectors ligated to different detector probes constitutes a catalog of nucleic acid fragments in the nucleic acid sample,
wherein the pattern is compared to a predicted pattern based on probabilities of base mismatches of sequences hybridized to the detector probes.

105. The method of claim 8 wherein each adaptor-indexer comprises a nucleic acid comprising a single-stranded portion and a double-stranded portion, wherein the single-stranded portion is the sticky end, and wherein the double-stranded portion has the same sequence in each adaptor-indexer.

106. The method of claim 8 wherein detecting ligation of the ligator-detectors to the detector probes is accomplished by detecting the adaptor-indexers, the ligated ligator-detectors, mass labels associated with the adaptor-indexers, mass labels associated with the ligated ligator-detectors, or a combination, by mass spectroscopy.

107. The method of claim 106 wherein the adaptor-indexers, ligated ligator-detectors, mass labels associated with the adaptor-indexers, and mass labels associated with the ligated ligator-detectors are detected by matrix-assisted laser desorption/ionization time-of-flight mass spectroscopy.

108. The method of claim 106 wherein the composition of the adaptor-indexers, ligated ligator-detectors, mass labels associated with the adaptor-indexers, and mass labels associated with the ligated ligator-detectors are determined by analyzing the fragmentation pattern.

109. The method of claim 106 wherein unligated ligator-detectors are washed away from the detector probes prior to detection of the ligated adaptor-indexers.

110. The method of claim 106 further comprising, following step (b), incubating the index samples with one or more second nucleic acid cleaving reagents.

111. The method of claim 106 wherein the adaptor-indexers, the detector probes, or both, contain a photocleavable nucleotide, wherein the method further comprises, following ligation of the ligator-detectors to the detector probes,
 photocleavage of the photocleavable nucleotides, and
 detection of one or both strands of the ligated ligator-detector by mass spectroscopy.

112. The method of claim 106 further comprising, following ligation of the ligator-detectors to the detector probes,
 incubation of the ligated ligator-detectors and detector probes with one or more nucleic acid cleaving reagents, and
 detection of one or both strands of the ligated ligator-detector by mass spectroscopy.

113. The method of claim 8 further comprising, following step (b),
 incubating the index samples with one or more second nucleic acid cleaving reagents, and
 mixing a second adaptor with each index sample and ligating the second adaptors to the nucleic acid fragments, wherein each second adaptor has an end compatible with the end generated by one of the second nucleic acid cleaving reagents,
 wherein at least one of the second nucleic acid cleaving reagents is sensitive to modification of its recognition site.

114. The method of claim 113 wherein the first and second nucleic acid cleaving reagents are restriction enzymes.

115. The method of claim 114 wherein the modification to the recognition site is methylation, alkylation, dimerization, derivatization, depurination, or ADP-ribosylation.

116. The method of claim 114 wherein the modification is present in the nucleic acid fragments when isolated or is introduced to the nucleic acid fragments after isolation.

117. The method of claim 114 further comprising, prior to step (c),
 dividing each index sample into one or more restricted index samples and a non-restricted index sample,
 digesting each restricted index sample with a different third restriction enzyme,
 wherein steps (c), (d), and (e) are performed with both the restricted and non-restricted index samples.

118. The method of claim 114 further comprising, following ligation of the second adaptors to the nucleic acid fragments,
 amplifying the nucleic acid fragments in the index samples to which adaptor-indexers and second adaptors have been ligated.

119. The method of claim 118 further comprising determining the sequence of a portion of at least one of the nucleic acid fragments in the nucleic acid sample.

120. The method of claim 114 further comprising, following ligation of the second adaptors to the nucleic acid fragments,
 separating nucleic acid fragments ligated to second adaptors from nucleic acid fragments not ligated to second adaptors, wherein only nucleic acid fragments ligated to second adaptors are used in step (c).

121. The method of claim 114 wherein at least one of the second restriction enzymes (1) is insensitive to modification of its recognition site and (2) has the same recognition site as the second restriction enzyme that is sensitive to modification of its recognition site,
 the method further comprising, prior to digestion with the second restriction enzymes,
 dividing each index sample into a set of two or more of secondary index samples,
 wherein each secondary index sample in each set of secondary index samples is digested with a different second restriction enzyme,
 wherein steps (c) through (e) are performed with each of the secondary index samples.

122. The method of claim 121 further comprising,
 comparing the pattern of the presence or absence of ligator-detectors ligated to different detector probes involving the second restriction enzyme that is sensitive to modification of its recognition site with the pattern of the presence or absence of ligator-detectors ligated to different detector probes involving the second restriction enzyme that is insensitive to modification of its recognition site and that has the same recognition site as the second restriction enzyme that is sensitive to modification of its recognition site,
 wherein differences in the patterns indicate modification of nucleic acids in the nucleic acid sample.

123. The method of claim 114 wherein the pattern of the presence, amount, presence and amount, or absence of ligator-detectors ligated to different detector probes constitutes a catalog of nucleic acid fragments in the nucleic acid sample.

124. The method of claim 123 further comprising preparing a second catalog of nucleic acid fragments in a second nucleic acid sample and comparing the first catalog and second catalog, wherein differences in the first and second catalogs indicate differences in modification of the first and second nucleic acid samples.

125. The method of claim 123 wherein the second nucleic acid sample is a sample from the same type of cells as the first nucleic acid sample except that the cells from which the first nucleic acid sample is derived are modification-deficient relative to the cells from which the second nucleic acid sample is derived.

126. The method of claim 123 wherein the second nucleic acid sample is a sample from a different type of cells than the first nucleic acid sample, and wherein the cells from which the first nucleic acid sample is derived are modification-deficient relative to the cells from which the second nucleic acid sample is derived.

127. The method of claim 6 wherein the nucleic acid cleaving reagents are restriction enzymes, wherein the restriction enzymes are type II-S restriction enzymes that cleave at sites different from their recognition sequences, the method further comprising, prior to step (a), introducing a recognition site for the restriction enzyme adjacent to a region of interest in one or more nucleic acid molecules in the nucleic acid sample, wherein the ligator-detector comprises sequence matching or complementary to all or part of the sequence of, and adjacent to, the recognition site for the restriction enzyme.

128. The method of claim 127 wherein the recognition site is introduced by amplifying the nucleic acid molecules using a primer containing the recognition sequence.

129. The method of claim 128 wherein the nucleic acid molecules are amplified using PCR.

130. The method of claim 127 wherein the detector probes include sequence matching or complementary to known or potential sequence in the region of interest.

131. The method of claim 130 wherein there are a plurality of known or potential sequences in the region of interest, wherein the set of detector probes includes probes that include sequence matching or complementary to each known or potential sequence.

132. The method of claim 131 the nucleic acid molecules in the nucleic acid sample are immunoglobulin or T cell receptor nucleic acid molecules, wherein the nucleic acid molecules have a variable region, an N region, and a joining region, wherein the recognition site for the restriction enzyme is introduced into the variable region of the nucleic acid molecules adjacent to the N region of the nucleic acid molecules, wherein the ligator-detector comprises sequence matching or complementary to all or part of the sequence of the recognition site for the restriction enzyme and all or a part of the sequence of the variable region sequence adjacent to the recognition site for the restriction enzyme, up to, but not including, the N region, wherein the plurality of known or potential sequences are sequences matching or complementary to all or a part of the sequence of the joining region of the nucleic acid molecules adjacent to the N region of the nucleic acid molecules.

133. A kit comprising a set of adaptor-indexers wherein each adaptor-indexer has a different sticky end, wherein each sticky end of the adaptor-indexes is compatible with a sticky end generated by one or more nucleic acid cleaving reagents that collectively generate sticky ends having a plurality of different sequences, a set of ligator-detectors wherein each ligator-detector comprises sequence matching or complementary to all or part of the sticky end of a different adaptor-indexer and to all or part of the adjacent sequence of the adaptor-indexer, and a plurality of detector probes, wherein each detector probe has a different sequence.

134. The kit of claim 133 wherein each sticky end of the adaptor-indexes is compatible with a sticky end generated by a restriction enzyme.

135. The kit of claim 133 wherein the kit includes at least one ligator-detector corresponding to each adaptor-indexer.

136. The kit of claim 135 wherein at least one adaptor-indexer, at least one ligator-detector, at least one detector probe, or a combination, contains a label.

137. The kit of claim 136 wherein the labels are fluorescent, phosphorescent, or chemiluminescent labels.

138. The kit of claim 137 wherein at least two of the labels are distinguished temporally via different fluorescent, phosphorescent, or chemiluminescent emission lifetimes.

139. The kit of claim 136 wherein the labels are detectable by nuclear magnetic resonance, electron paramagnetic resonance, surface enhanced raman scattering, surface plasmon resonance, fluorescence, phosphorescence, chemiluminescence, resonance raman, microwave, or a combination.

140. The kit of claim 136 wherein the labels are beads comprising a label.

141. The method of claim 140 wherein the label is a molecular barcode.

142. The kit of claim 136 wherein the labels are mass labels.

143. The kit of claim 133 wherein the nucleic acid cleaving reagent generates sticky ends having N different sequences, and wherein the kit includes N different adaptor-indexers.

144. The kit of claim 133 wherein the detector probes are six, seven, or eight nucleotides long.

145. The kit of claim 133 wherein each ligator-detector contains a label.

146. The kit of claim 145 wherein the label is a fluorescent label.

147. The kit of claim 145 wherein the kit includes at least two ligator-detectors corresponding to each adaptor-indexer, wherein each ligator-detector corresponding to a given adaptor-indexer contains a different label.

148. The kit of claim 133 wherein the detector probes are all of the same length.

149. The kit of claim 133 wherein the detector probes all have similar hybrid stability.

150. The kit of claim 133 wherein each adaptor-indexer, ligator-detector, or detector probe is immobilized on a substrate.

151. The kit of claim 150 wherein the detector probes are immobilized on a substrate.

152. The kit of claim 133 wherein each adaptor-indexer, ligator-detector, or detector probe is associated with a capture tag, sorting tag, or both.

153. The kit of claim 152 wherein the ligator-detectors are associated with capture tags or sorting tags.

154. The kit of claim 133 wherein the detector probes are nucleic acid fragments prepared by (a) incubating a nucleic acid sample with one or more nucleic acid cleaving reagents that collectively generate sticky ends having a plurality of different sequences to produce nucleic acid fragments with sticky ends, (b) mixing a plurality of adaptor-indexers with the nucleic acid sample and covalently coupling the adaptor-indexers to the nucleic acid fragments, wherein each adaptor-indexer has a different sticky end, wherein each sticky end of the adaptor-indexers is compatible with a sticky end generated by the nucleic acid cleaving reagents, (c) hybridizing a plurality of ligator-detectors with the nucleic acid sample, wherein each ligator-detector comprises sequence matching or complementary to all or part of sequence including, and adjacent to, the sticky end of at least one of the adaptor-indexers, (d) hybridizing the nucleic acid sample with a plurality of detector probes and covalently coupling the ligator-detectors to the detector probes, wherein each detector probe has a different sequence, and (e) detecting, directly or indirectly, coupling of ligator-detectors to the detector probes, wherein the pattern of ligator-detectors coupled to different detector probes constitutes a catalog of nucleic acid fragments in the nucleic acid sample, (f) preparing a second catalog of nucleic acid fragments in a second nucleic acid sample and comparing the first catalog and second catalog, and (g) preparing nucleic acid fragments corresponding the nucleic acid fragments present in the first nucleic acid sample but not present in the second nucleic acid sample.

* * * * *